US007723501B2

(12) United States Patent
Reed et al.

(10) Patent No.: US 7,723,501 B2
(45) Date of Patent: May 25, 2010

(54) BAG PROTEINS AND NUCLEIC ACID MOLECULES ENCODING THEM

(75) Inventors: John C. Reed, Rancho Santa Fe, CA (US); Shinichi Takayama, San Diego, CA (US)

(73) Assignee: Burham Institute for Medical Research, La Jolla, CA (US)

( * ) Notice: Subject to any disclaimer, the term of this patent is extended or adjusted under 35 U.S.C. 154(b) by 251 days.

(21) Appl. No.: 11/879,274

(22) Filed: Jul. 16, 2007

(65) Prior Publication Data
US 2009/0131646 A1    May 21, 2009

Related U.S. Application Data

(60) Division of application No. 10/782,627, filed on Feb. 18, 2004, which is a continuation of application No. 09/394,142, filed on Sep. 9, 1999, now Pat. No. 6,696, 558.

(60) Provisional application No. 60/155,212, filed on Sep. 9, 1998.

(51) Int. Cl.
*C07H 21/02* (2006.01)
(52) U.S. Cl. ............ 536/23.1; 536/23.5; 530/350
(58) Field of Classification Search ............ 536/23.1, 536/23.5; 530/350
See application file for complete search history.

(56) References Cited

U.S. PATENT DOCUMENTS

| 5,539,094 | A | | 7/1996 | Reed et al. |
| 5,650,491 | A | | 7/1997 | Reed et al. |
| 5,652,223 | A | | 7/1997 | Kohn et al. |
| 6,110,690 | A | * | 8/2000 | Goeddel et al. ............ 435/7.1 |
| 2001/0053519 | A1 | * | 12/2001 | Fodor et al. ............ 435/6 |

FOREIGN PATENT DOCUMENTS

WO    WO 95/13292    5/1995

OTHER PUBLICATIONS

Boehringer Mannheim Biochemicals, 1994 Catalog (No. 1034 731/1006 924), p. 93.*
Skolnick et al. (Trends Biotech. 2000; 18: 34-39).*
Bowie et al. (Science. 1990; 257: 1306-1310).*
Burgess et al. (J. Cell Biol. 1990; 111:2129-2138).*
Lazar et al. (Mol. Cell. Biol. 1988; 8:1247-1252).*
Ausubel et al., *Current Protocols in Molecular Biology*, John Wiley and Sons, New York (1994).
Database, Genbank-EST, National Center for Biotech. Info., Accession No. AA693697, Hillier et al., "WashU-NCI human EST project," Dec. 16, 1997.
Database, Genbank-EST, National Center for Biotech. Info., Accession No. AA456862, NCI_CGAP, "National Cancer Institute, Cancer Genome Anatomy Project (CGAP), Tumor Gene Index," Aug. 15, 1997.
Database, Genbank-EST, National Center for Biotech. Info., Accession No. G29287, Myers, Oct. 4, 1996.
Database, Genbank-EST, National Center for Biotech. Info., Accession No. G06974, Hudson, "Whitehead Institute.MIT Center for Genome Research," Oct. 19, 1995.
Database, Genbank-EST, National Center for Biotech. Info., Accession No. V81267, Otsuka Pharm Co. Ltd., "New Bcl-2 interaction protein gene (Bis)-useful for elucidation of the molecular mechanism of apoptosis, and in diagnosis, prevention and treatment of diseases," Dec. 15, 1998.
Database, Genbank-EST, National Center for Biotech. Info., Accession No. T19051, Matsubara et al., "Identifying gene signatures in 3'-directed human cDNA library," Jun. 1, 1995.
Database, Genbank-EST, National Center for Biotech. Info., Accession No. Q90296, La Jolla Cancer Research Foundation, "Human Bcl-2 associated protein BAG-1 cDNA," May 18, 1995.
Ellis, "Molecular chaperones: Avoiding the crowd," *Curr. Biol.* 7:R531-R533 (1997).
Grunert and Jackson, "The immediate downstream codon strongly influences the efficiency of utilization of eukaryotic translation initiation codons," *EMBO J.* 13:3618-3630 (1994).
Hillier, L., et al., Unpublished, 1997, Database GenBank EST Accession No. AI815738, au43g01.y1 "Schneider fetal brain 00004 *Homo sapiens* cDNA clone Image:2517552, 5'similar to TR:075315".
Höhfeld et al., "Hip, a novel cochaperone involved in the eukaryotic Hsc70/Hsp40 reaction cycle," *Cell* 83:589-598 (1995).
Höhfeld et al., "GrpE-like regulation of the Hsc70 chaperone by the anti-apoptotic protein BAG-1," *EMBO J.* 16:6209-6216 (1997).
Huse et al., "Generation of a large combinatorial library of the immunoglobulin repertoire in phage lambda," *Science* 246:1275-1281 (1989).
Innis et al., PCR Protocols—*A guide to methods and applications*, Academic Press, Inc., pp. 40-41 (1990).
Kozak, "Recognition of AUG and alternative initiator codons is augmented by G in position +4 but is not generally affected by the nucleotides in positions +5 and +6," *EMBO J.* 16:2482-2492 (1997).
Matsuzawa et al., "p53-inducible human homologue of *Drosophila* seven in absentia (Siah) inhibits cell growth: suppression by BAG-1," *EMBO J.* 17:2736-2747 (1998).
Minami et al., "Regulation of the heat-shock protein 70 reaction cycle by the mammalian DnaJ homolog, Hsp40," *J. Biol. Chem.* 271:19617-19624 (1996).
Nielsen, P.E. et al., "Peptide nucleic acids (PNAs): Potential antisense and anti-gene agents," *Anticancer Drug Des.* 8:53-63 (1993).
Prapapanich et al., "Mutation of Hip's carboxy-terminal region inhibits a transitional stage of progesterone receptor assembly," *Mol. & Cell Biol.* 18:944-952 (1998).

(Continued)

*Primary Examiner*—Stephen L Rawlings
(74) *Attorney, Agent, or Firm*—McDermott Will & Emery LLP

(57) ABSTRACT

The present invention provides a family of BAG-1 related proteins from humans (BAG-1L, BAG-1, BAG-2, BAG-3, BAG-4 and BAG-5), the invertebrate *C. elegans* (BAG-1, BAG-2) and the fission yeast *S. pombe* (BAG-1A, BAG-1B) and the nucleic acid molecules that encode them.

8 Claims, 39 Drawing Sheets

OTHER PUBLICATIONS

Sambrook et al., *Molecular cloning: A laboratory manual*, 2nd Edition, Cold Spring Harbor Laboratory Press, (1989).

Search Report "us-09-394-142b-2.rge," pp. 3 and 4; see result 3.

Sudol, "The WW module competes with the SH3 domain?," *TIBS* 21:161-163 (1996).

Takayama, S, Direct Submission, Sep. 3, 1997, Database GenBank Accession No. AF022224, "*Homo sapiens* Bc1-2-binding protein (BAG-1) mRNA, complete cds".

Takayama et al., "Cloning of cDNAs Encoding the Human BAG1 Protein and Localization of the Human BAG1 Gene to Chromosome 9p12," *Genomics*, 35:494-498 (1996).

Takayama et al., "BAG-1 modulates the chaperone activity of Hsp70/Hsc70," *EMBO J.* 16:4887-4896 (1997).

Takayama et al., "Expression and Location of Hsp70/Hsc-Binding Anti-Apoptotic Protein Bag-1 and Its Variants in Normal Tissues and Tumor Cell Lines," *Canc. Res.*, 58:3116-3131(1998).

Takayama et al., "An Evolutionarily Conserved Family of Hsp70/Hsc70 Molecular Chaperone Regulators," *J. Biol. Chem.*, 274(2):781-786 (1999).

Terada et al., "The human DnaJ homologue dj2 facilitates mitochondrial protein import and luciferase refolding," *J. Cell Biol.* 139:1089-1095 (1997).

Xie et al., "Acidic pH promotes dimerization of Bcl-2 family proteins," *Biochem.* 37:6410-6418 (1998).

Zeiner, M, Direct Submission, Jul. 28, 1994, Database GenBank Accession No. Z35491, "*H. sapiens* mRNA for novel glucocorticoid receptor-associated protein".

Zeiner et al., "Mammalian protein RAP46: an interaction partner and modulator of 70 kDa heat shock proteins," *EMBO J.* 16:5483-5490 (1997).

Zeiner and Gehring, "A protein that interacts with members of the nuclear hormone receptor family: Identification and cDNA cloning," *Proc. Natl. Acad. Sci. USA* 92:11465-11469 (1995).

* cited by examiner

FIG. 1

```
GCAGCCGCGG TGTCGCGAAG TCCTCCCGGG TTGCCCCCGC GGCGTCAGAG GGAGGGCGGG CGCCGCGTTG GTGACGGGCA CCCTGCAGCC     90
CAGGAGGCGC TCCACTCGCT GCCGCCGGAG GGCGGGTGAC CTCTTGGCTA CCCCGCGTCG GAGGCTTAGA TGGCTCAGGC GAAGATCAAC    180
                                                                         M  A  Q  A  K  I  N

GCTAAGCCA ACGAGGGGCG CTTTGCCGC TCCTCCTCCA TGGCTGACCG CTCCAGCCGC CTGCTGGAGA GCCTGGACCA GCTGGAGCTC      270
A  K  A  N  E  G  R   F  C  R   S  S  S  M   A  D  R   S  S  R   L  L  E   S  L  D  Q   L  E  L

AGGGTTGAAG CTTTGAGAGA AGCAGCAACT GCTGTTGAGC AAGAGAAGGA AATCCTTCTG GAAATGATCC ACAGTATCCA AAATAGCCAG    360
R  V  E  A  L  R  E    A  A  T   A  V  E  Q   E  K  E   I  L  L   E  M  I   H  S  I  Q   N  S  Q

GACATGAGGC AGATCAGTGA CGGAGAAGA GAAGAATTAA ATCTGACTGC AAACCGTTTG ATGGGAAGA CTCTCACCGT TGAAGTGTCA      450
D  M  R  Q  I  S  D   G  E  R    E  E  L  N   L  T  A   N  R  L   M  G  R  T   L  T  V   E  V  S

GTAGAAACAA TTAGAAACCC CCAGCAGCAA GAATCCCTAA AGCATGCCAC AGGATTATT GATGAGGTGG TCAATAAGTT TCTGGATGAT     540
V  E  T  I  R  N  P   Q  Q  Q   E  S  L  K   H  A  T   R  I  I   D  E  V  V   N  K  F   L  D  D

TTGGGAATG CCAAGAGTCA TTTAATGTCG CTCTACAGTG CATGTTCATC TGAGGTGCCA CATGGGCCAG GTTTCATCC GTTTCAATCC      630
L  G  N  A  K  S  H   L  M  S    L  Y  S  A   C  S  S   E  V  P   H  G  P  V   D  Q  K   F  Q  S

ATAGTAATTG GCTGTGCTCT TGAAGATCAG AAGAAATTA AGAGAAGATT AGAGACTCTG CTTAGAAATA TTGAAAACTC TGACAAGGCC     720
I  V  I  G   C  A  L   E  D  Q   K  K  I  K   R  R  L   E  T  L   L  R  N  I   E  N  S   D  K  A

ATCAAGCTAT TAGAGCATTC TAAAGGAGCT GGTTCCAAAA CTCTGCAACA AAATGCTGAA AGCAGATTCA ATTAGTCTTC AAACCTAAGA    810
I  K  L  L  E  H  S   K  G  A   G  S  K  T   L  Q  Q   N  A  E    S  R  F  N
```

FIG. 2A

```
GCATTTACAC AATACACAAG GTGTAAAAAT GATAAATAC TATTTAATT GATAACTAGT TCTTTGTTAG GTATAACCAC TTAGTTGACA    900
CTGATAGTTG TTTCAGATGA GGAAATATT CCATCAAGTA TCTTCAGTTT TGTGAATAAC AAAACTAGCA ATATTTAAT TATCTATCTA    990
GAGATTTTTT AGATTGAATT CTTGTCTTGT ACTAGGATCT AGCATATTTC ACTATTCTGT GGATGAATAC ATAGTTTGTG GGGAAACAA   1080
ACGTTCAGCT AGGGGCAAAA AGCATGACTG CTTTTTCCTG TCTGGCATGG AATCACGCAG TCACCTTGGG CATTTAGTTT ACTAGAAATT  1170
CTTTACTGG                                                                                          1179
```

FIG. 2B

```
GCGGAGCTCC GCATCCAACC CCGGGCCGCG GCCAACTTCT CTGGACTGGA CCAGAAGTTT CTAGCCGGCC AGTTGCTACC TCCCTTTATC    90
 A  E  L  R   I  Q  P   R  A  A   A  N  F  S   G  L  D   Q  K  F   L  A  G   Q  L  L  P   P  F  I

TCCTCCTTCC CCTCTGGCAG CGAGGAGGCT ATTTCCAGAC ACTTCCACCC CTCTCTGGCC ACGTCACCCC CGCCTTTAAT TCATAAAGGT   180
 S  S  F  P   S  G  S   E  E  A   I  S  R  H   F  H  P   S  L  A   T  S  P  P   P  L  I   H  K  G

GCCCGGCGCC GGCTTCCCGG ACACGTCGGC GGCGGAGAGG GGCCCACGGC GGCGGCCCGG CCAGAGACTC GGCGCCCGGA GCCAGCGCCC   270
 A  R  R  R   L  P  G   H  V  G   G  G  E  G   P  T  A   A  A  R   P  E  T  R   A  P  E   P  A  P

CGCACCCGCG CCCCAGCGGG CAGACCCCAA CCCAGCATGA GCGCCGCCAC CCACTCGCCC ATGATGCAGG TGGCGTCCGG CAACGGTGAC   360
 R  T  A  A   P  A  G   R  P  Q   P  S  M  S   A  A  T   H  S  P   M  M  Q  V   A  S  G   N  G  D

CGCGACCCTT TGCCCCCCGG ATGGGAGATC AAGATCGACC CGCAGACCGG CTGGCCCTTC TTCGTGGACC ACAACAGCCG CACCACTACG   450
 R  D  P  L   P  P  G   H  E  I   K  I  D  P   Q  T  G   W  P  F   F  V  D  H   N  S  R   T  T  T

TGGAACGACC CGCGCGTGCC CTCTGAGGGC CCCAAGGAGA CTCCATCCTC TGCCAATGGC CCTTCCCGGG AGGGCTCTAG GCTGCCGCCT   540
 W  N  D  P   R  V  P   S  E  G   P  K  E  T   P  S  S   A  N  G   P  S  R  E   G  S  R   L  P  P

GCTAGGGAAG GCCACCCTGT GTACCCCCAG CTCCGACCAG GCTACATTCC CATTCCTGTG CTCCATGAAG GCGCTGAGAA CCGGCAGGTG   630
 A  R  E  G   H  P  V   Y  P  Q   L  R  P  G   Y  I  P   I  P  V   L  H  E  G   A  E  N   R  Q  V

CACCCTTTCC ATGTCTATCC CCAGCCTGGG ATGCAGCGAT TCCGAACTGA GGCGGCAGCA GCGGCTCCTC AGAGGTCCCA GTCACCTCTG   720
 H  P  F  H   V  Y  P   Q  P  G   M  Q  R  F   R  T  E   A  A  A   A  P  Q  R   S  Q  S   P  L

CGGGGCATGC CAGAAACCAC TCAGCCAGAT AAACAGTGTG GACAGGTGGC AGCGGCGGCG GCAGCCCAGC CCCAGCCTC  CCACGGACCT   810
 R  G  M  P   E  T  T   Q  P  D   K  Q  C  G   Q  V  A   A  A  A   A  A  Q  P   P  A  S   H  G  P

GAGCGGTCCC AGTCTCCAGC TGCCTCTGAC TGCTCATCCT CATCCTCCTC GGCCAGCCTG CCTTCCTCCG GCAGGAGCAG CCTGGGCAGT   900
 E  R  S  Q   S  P  A   A  S  D   C  S  S  S   S  S  S   A  S  L   P  S  S  G   R  S  S   L  G  S

CACCAGCTCC CGCGGGGGTA CATCTCCATT CCGGTGATAC ACGAGCAGAA CGTTACCCGG CCAGCAGCCC AGCCCTCCTT CCACAAAGCC   990
 H  Q  L  P   R  G  V   I  S  I   P  V  I  H   E  Q  N   V  T  R   P  A  A  Q   P  S  F   H  K  A

CAGAAGACGC ACTACCCAGC GCAGAGGGGT GAGTACCAGA CCCACCAGCC TGTGTACCAC AAGATCCAGG GGGATGACTG GGAGCCCCGG   1080
 Q  K  T  H   Y  P  A   Q  R  G   E  Y  Q  T   H  Q  P   V  Y  H   K  I  Q  G   D  D  W   E  P  R

CCCCTGCGGG CGGCATCCCC GTTCAGGTCA TCTGTCCAGG GTGCATCAGG CCGGGAGGGC TCACCAGCCA GGAGCAGCAC GCCACTCCAC   1170
 P  L  R  A   A  S  P   F  R  S   S  V  Q  G   A  S  R   E  G   S  P  A  A   S  S  T   P  L  H

TCCCCCTCGC CCATCCGTGT GCACACCGTG GTCGACAGGC CTCAGCAGCC CATGACCCAT CGAGAAACTG CACCTGTTTC CCAGCCTGAA   1260
 S  P  S  P   I  R  V   H  T  V   V  D  R  P   Q  Q  P   M  T  H   R  E  T  A   P  V  S   Q  P  E

AACAAACCAG AAAGTAAGCC AGGCCCAGTT GGACCAGAAC TCCCTCCTGG ACACATCCCA ATTCAAGTGA TCCGCAAAGA GGTGGATTCT   1350
 N  K  P  E   S  K  P   G  P  V   G  P  E  L   P  P  G   H  I  P   I  Q  V  I   R  K  E   V  D  S

AAACCTGTTT CCCAGAAGCC CCCACCTCCC TCTGAGAAGG TAGAGGTGAA AGTTCCCCCT GCTCCAGTTC CTTGTCCTCC TCCCAGCCCT   1440
 K  P  V  S   Q  K  P   P  P  P   S  E  K  V   E  V  K   V  P  P   A  P  V  P   C  P  P   P  S  P

GGCCCTTCTG CTGTCCCCTC TTCCCCCAAG AGTGTGGCTA CAGAAGAGAG GGCAGCCCCC AGCACTGCCC CTGCAGAAGC TACACCTCCA   1530
 G  P  S  A   V  P  S   S  P  K   S  V  A  T   E  E  R   A  A  P   S  T  A  P   A  E  A   T  P  P

AAACCAGGAG AAGCCGAGGC TCCCCCAAAA CATCCAGGAG TGCTGAAAGT GGAAGCCATC CTGGAGAAGG TGCAGGGGCT GGAGCAGGCT   1620
 K  P  G  E   A  E  A   P  P  K   H  P  G  V   L  K  V   E  A  I   L  E  K  V   Q  G  L   E  Q  A

GTAGACAACT TTGAAGGCAA GAAGACTGAC AAAAAGTACC TGATGATCGA AGAGTATTTG ACCAAAGAGC TGCTGGCCCT GGATTCAGTG   1710
 V  D  N  F   E  G  K   K  T  D   K  K  Y  L   M  I  E   E  Y  L   T  K  E  L   L  A  L   D  S  V

GACCCCGAGG GACGAGCCGA TGTGCGTCAG GCCAGGAGAG ACGGTGTCAG GAAGGTTCAG ACCATCTTGG AAAAACTTGA ACAGAAAGCC   1800
 D  P  E  G   R  A  D   V  R  Q   A  R  R  D   G  V  R   K  V  Q   T  I  L  E   K  L  E   Q  K  A

ATTGATGTCC CAGGTCAAGT CCAGGTCTAT GAACTCCAGC CCAGCAACCT TGAAGCAGAT CAGCCACTGC AGGCAATCAT GGAGATGGGT   1890
 I  D  V  P   G  Q  V   Q  V  Y   E  L  Q  P   S  N  L   E  A  D   Q  P  L  Q   A  I  M   E  M  G

GCCGTGGCAG CAGACAAGGG CAAGAAAAAT GCTGGAAATG CAGAAGATCC CCACACAGAA ACCCAGCAGC CAGAAGCCAC AGCAGCAGCG   1980
 A  V  A  A   D  K  G   K  K  N   A  G  N  A   E  D  P   H  T  E   T  Q  Q  P   E  A  T   A  A  A

ACTTCAAACC CCAGCAGCAT GACAGACACC CCTGGTAACC CAGCAGCACC GTAGCCTCTG CCCTGTAAAA GTCAGACTCG GAACCGATGT   2070
 T  S  N  P   S  S  M   T  D  T   P  G  N  P   A  A  P

GTGCTTTAGG GATTTTAGTT GCATGCATTT CAGAGACTTT AGGTCAGTTG GTTTTGATTA GCTGCTTGGT ATGCAGTACT TGGGTGAGGC   2160
AAACACTATA AAGGGCTAAA AGGGAAAATG ATGCTTTTCT TCAATATTCT TACTCTTGTA CAATTAAAGA AGTTGCTTGT TGTTTGAGAA   2250
GTTTAACCCC GTTGCTTGTT CTGCAGCCCT GTCAACTTGG GCACCCCCAC CACCTGTTAG CTGTGGTTGT GCACTGTCTT TTGTAGCTCT   2340
GGACTGGAGG GGTAGATGGG GAGTCAATTA CCCATCACAT AAATATGAAA CATTTATCAG AAATGTTGCC ATTTTAATGA GATGATTTTC   2430
TTCATCTCAT AATTAAAATA CCTGACTTTA GAGAGAGTAA AATGTGCCAG GAGCCATAGG AATATCTGTA TGTTGGATGA CTTTAATGCT   2520
ACATTTTH                                                                                          2528
```

FIG.3

```
ACGATATCCT GTAAGACCAA GAATTGCAAG GCCAGAGTTT GAATTCTTAT ACAATGGAAG CGTATGGTCC AACATACCCC CCAGGCCCTG     90
GGCAATAC TGCCTCATAC TCAGGGCTT ATTATGCACC TGGTTATACT CAGACCAGTT ACTCCACAGA AGTTCCAAGT ACTTACCGTT    180
CATCTGGCAA CAGCCAACT CCAGTCTCTC GTTGGATCTA TCCCCAGCAG GACTGTCAAG ACTGAAGCAC CCCCTCTTAA GGGGCAGGTT    270
CCAGGATATC CGCCTTCACA GAACCCTGGA ATGACCCTGC CCCATTATCC TTATGGAGAT GGTATCGTA GTGTTCCACA ATCACGGCCG    360
                                                                    M E  M  V  I  V  V F H N  H G R
ACTGTACGAC CACAAGAAAG ATGCGTGGGC TTCTCCTGGT GCTTATGGAA TGGGTGGCCG TTATCCCTGG CCTTCATCAG CGCCCTCAGC    450
 L Y D  H K K D  A W A  S P G  A Y G M  G G R  Y P W  P S S A  P S A
ACCACCCGGC AATCTCTACA TGACTGAAAG TACTTCACCA TGGCCTAGCA GTCCCTAGCA GTGGCTCTCC CCAGTCACCC CCTTCACCC CAGTCCAGCA    540
 P P G  N L Y M  T E S  T S P  W P S S  S G S P  Q S P  P S P P  V Q Q
GCCAAGGAT TCTTCATACC CCTATAGCCA ATCAGATCAA AGCATGAACC GGCACACTT TCCTTGCAGT GTCATCAGT ACGATCCTC    630
 P K D  S S Y P  Y S Q  S D Q  S M N R  H N F  P C S  V H Q Y  E S S
GGGACAGTG AACATGATG ATTCAGATCT TTTGGATTCC CAGTCCAGT ATAGTGCTGA GCCTCAGCTG TATGGTAATG CCACCAGTGA    720
 G T V  N D D  S D L  L D S  Q V Q Y  S A E  P Q L  Y G N A  T S D
CCATCCCAAC AATCAGGATC AAAGTAGCAG TCTTCCTGAA GAATGTGTAC CTTCAGATGA AGTACTCCT CCGAGTATTA AAAAAATCAT    810
 H P N  N Q D Q  S S S  L P E  E C V P  S D E  S T P  P S I K  K I I
ACATGTGCTG GAGAGGTCC AGTATCTTGA ACAGAGAGTA GAAGAATTTG TAGGAAAAAA GACAGACAAA GCATACTGGC TTCTGGAAGA    900
 H V L  E K V Q  Y L E  Q E V  E E F V  G K K T D K  A Y W L  L E E
AATGCTAACC AGGACTACC TGGACTTGAA TTCAGTTGAA ACTGGGGGCC AGGACTCTGT AGGAAAGAGG CTGTTTGTAA    990
 M L T  K E L L  E L D  S V E  T G G Q  D S V  R Q A  R K E A  V C K
GATTCAGGCC ATATTGGAAA                                                                              1010
 I Q A  I L E
```

FIG. 4

```
GAGAATAAA AAATGAACTT CTCCAAGCAC AAACCCTTC TGAATTGTAC CTGAGCTCCA AAACAGAATT GCAGGGTTTA ATTGGACAGT      90
 E  I  K   N  E  L   L  Q  A  Q   N  P  S   E  L  Y   L  S  S  K   T  E  L   Q  G  L   I  G  Q  L

TGGATGAGGT AAGTNTTGAA AAAACCCCT GCATCCGGGA AGCCAGGAGA AGAGCAGTGA TCGAGGTGCA AACTCTGATC ACATATATTG   180
 D  E  V   S  X  E   K  N  P  C   I  R  E   A  R  R   R  A  V  I   E  V  Q   T  L  I   T  Y  I  D

ACTTGAAGGA GGCCCTTGAG AAAGAAAGC TGTTTGCTTG TGAGGAGCAC CCATCCCATA AAGCCGTCTG GAACGTCCTT GGAACTTGT   270
 L  K  E   A  L  E   K  R  K  L   F  A  C   E  E  H   P  S  H  K   A  V  W   N  V  L   G  N  L  S

CTGAGATCCA GGGAGAAGTT CTTTCATTTG ATGGAAATCG AACCATACCC GGCTGGAAGA ACTACATCC GGCTGGAAGA GCTGCTAACC GGCTGCTCACC AAGCAGCTGC   350
 E  I  Q   G  E  V   L  S  F  D   G  N  R   T  D  K   N  Y  I  R   L  E  E   L  L  T   K  Q  L  L

TAGCCCTGGA TGCTGTTGAT CCGCAGGGAG AAGAGAAGTG TAAGGCTGCC AGGAAACAAG CTGTGAGGCT TGCGCAGAAT ATTCTCAGCT   450
 A  L  D   A  V  D   P  Q  G  E   E  K  C   K  A  A   R  K  Q  A   V  R  L   A  Q  N   I  L  S  Y

ATCTCGACCT GAATCTGAT GAATGGGAGT ACTGAAATAC CAGAGATCTC ACTTTTGATA CTTCATATGT GCTTCTATGT   540
 L  D  L   K  S  D   E  W  E  Y

ATAGAGAGGT TTCAGTTCAT TGATTTATAC ACGTTAACTT TTCCATTCGG ATCAAAAAA   630

TTGATGTTGC AAGACAAATA TCATTACAGC ACGTTAACTT TTCCATTCGG ATCAAAAAA   689
```

FIG. 5

ATGTCTTTCCGCCTCTTCGTTGAAATATTTCACTTTCTTTTCCAGCTTTTTCCCCATCTCGAC
CT
GCTTTGGTTTTT
CGAGAAAACCACGTTCCAAATCAGCGACATCTCTCAAATTGAGATCATAGGCTTTTTGAAGA
TTGCTCAAATTATG
CTTCTCATATTGCATGAGCATTTTGAAGCCCGCGTCATCAACCAAAGCATTTTTTCCACCCAT
CACAATGATTTTAT CATTTTCTTTAAAATT

FIG. 6A

| | | | | | |
|---|---|---|---|---|---|
| MKVNVSCSSV | QTTIDILEEN | QGEDESILTL | GQLRDRIATD | NDVDVETMKL | 50 |
| LHRGKFLQGA | DDVSLSTLNF | KENDKIIVMG | GKNALVDDAG | FKMLMQYEKH | 100 |
| NLSNLQKAYD | LNLRDVADLE | RGFLEKPKQV | EMGKKLEKKV | KYFNEEAERH | 150 |
| LETLDGMNII | TETTPENQAK | RNREKRKTLV | NGIQTLLNQN | DALLRRLQEY | 200 |
| QSVLNGDIPE | | | | | 210 |

FIG.6B

| | | | | | |
|---|---|---|---|---|---|
| ATGCCAGTCG | TGAACATACC | AATCAAAATA | CTTGGTCAGA | ATCAATCACA | 50 |
| TAGTCGAAGT | AACTCCTCGT | CTTCTGTTGA | CAACGATCGA | AATCAACCAC | 100 |
| CACAGCAGCC | ACCTCAACCG | CAACCACAAC | AGCAATCTCA | GCAACAATAC | 150 |
| CAGCAGGCTC | CAAACGTGAA | TACCAATATG | CATCATTCCA | ACGGATTCTC | 200 |
| ACCTAACTTC | CCATCTCGTA | GTCCTATTCC | GGACTTTCCC | AGTTTTTCAT | 250 |
| CTGGGTTCCC | AAACGATTCT | GAATGGTCTT | CGAATTTCCC | GTCGTTTCCA | 300 |
| AATTTCCCAA | GTGGATTCTC | AAATGGAAGT | TCTAATTTCC | CTGATTTTCC | 350 |
| AAGATTCGGA | AGAGATGGAG | GACTATCGCC | AAACCCACCG | ATGCAAGGAT | 400 |
| ACAGGAGAAG | TCCAACACCA | ACATCAACTC | AATCTCCAAC | TTCTACATTA | 450 |
| AGACGCAACT | CTCAGCAGAA | TCAAGCTCCT | CCACAATATT | CTCAGCAACA | 500 |
| ACCACAACAA | GCTCAACAAC | GTCAGACAAC | TCCTCCGTCA | ACAAAAGCTT | 550 |
| CATCTCGACC | ACCATCTCGT | ACTCGTGAAC | CAAAGGAACC | TGAGGTACCC | 600 |
| GAGAGACCAG | CAGTTATTCC | ATTGCCATAT | GAGAAGAAGG | AGAAACCACT | 650 |
| GGAGAAGAAA | GGTAGTCGTG | ATTCTGGAAA | GGGTGATGAG | AACCTTGAAG | 700 |
| AGAACATTGC | CAAGATCACG | ATCGGAAAGA | ATAATTGCGA | GTTATGTCCG | 750 |
| GAACAAGAAA | CGGACGGCGA | CCCATCTCCA | CTAACCTCCC | CAATCACCGA | 800 |
| AGGAAAGCCA | AAGAGAGGAA | AGAAACTTCA | ACGTAATCAA | AGTGTTGTTG | 850 |
| ATTTCAATGC | CAAGACAATT | GTTACTTTGG | ATAAAATTGA | ATTACAAGTT | 900 |
| GAGCAGTTGA | GAAAAAAAGC | TGCTGAACTC | GAAATGGAAA | AAGAGCAAAT | 950 |
| TCTTCGTTCT | CTAGGAGAAA | TCAGTGTTCA | TAACTGCATG | TTCAAACTGG | 1000 |
| AAGAATGTGA | TCGTGAAGAG | ATTGAAGCAA | TCACTGACCG | ATTGACAAAA | 1050 |
| AGAACAAAGA | CAGTTCAAGT | TGTTGTCGAA | ACTCCACGAA | ATGAAGAACA | 1100 |
| GAAAAAAGCA | CTGGAAGATG | CAACTTTGAT | GATCGATGAA | GTCGGAGAAA | 1150 |
| TGATGCATTC | GAATATTGAA | AAGGCTAAGC | TGTGCCTACA | AACCTACATG | 1200 |
| AACGCCTGTT | CGTACGAAGA | AACTGCTGGA | GCCACCTGCC | AAAACTTCTT | 1250 |
| GAAGATCATA | ATTCAGTGCG | CTGCTGATGA | TCAGAAACGC | ATCAAGCGTC | 1300 |
| GTCTGGAAAA | TCTGATGTCT | CAAATTGAGA | ATGCTGAGAG | AACGAAAGCA | 1350 |
| GATTTGATGG | ATGATCAAAG | CGAATAG | | | 1377 |

FIG.7A

| | | | | | |
|---|---|---|---|---|---|
| MPVVNIPIKI | LGQNQSHSRS | NSSSSVDNDR | NQPPQQPPQP | QPQQQSQQQY | 50 |
| QQAPNVNTNM | HHSNGFSPNF | PSRSPIPDFP | SFSSGFPNDS | EWSSNFPSFP | 100 |
| NFPSGFSNGS | SNFPDFPRFG | RDGGLSPNPP | MQGYRRSPTP | TSTQSPTSTL | 150 |
| RRNSQQNQAP | PQYSQQQPQQ | AQQRQTTPPS | TKASSRPPSR | TREPKEPEVP | 200 |
| ERPAVIPLPY | EKKEKPLEKK | GSRDSGKGDE | NLEENIAKIT | IGKNNCELCP | 250 |
| EQETDGDPSP | LTSPITEGKP | KRGKKLQRNQ | SVVDFNAKTI | VTLDKIELQV | 300 |
| EQLRKKAAEL | EMEKEQILRS | LGEISVHNCM | FKLEECDREE | IEAITDRLTK | 350 |
| RTKTVQVVVE | TPRNEEQKKA | LEDATLMIDE | VGEMMHSNIE | KAKLCLQTYM | 400 |
| NACSYEETAG | ATCQNFLKII | IQCAADDQKR | IKRRLENLMS | QIENAERTKA | 450 |
| DLMDDQSE | | | | | 458 |

FIG. 7B

| | | | | | |
|---|---|---|---|---|---|
| ATGTCAGAAA | AGACTAGCAC | AGTTACAATA | CACTATGGAA | ATCAGCGATT | 50 |
| TCCGGTAGCA | GTCAATCTAA | ATGAGACGTT | AAGTGAACTG | ATTGATGATT | 100 |
| TACTTGAAAC | GACTGAGATT | TCTGAGAAGA | AAGTCAAGCT | TTTTTACGCT | 150 |
| GGCAAGCGTT | TAAAAGACAA | AAAAGCCTCG | TTATCAAAAT | TGGGTTTAAA | 200 |
| AAATCATAGT | AAAATTCTAT | GTATAAGACC | ACATAAGCAA | CAACGAGGTT | 250 |
| CCAAGGAAAA | AGACACGGTT | GAGCCCGCTC | CGAAAGCGGA | AGCGGAGAAT | 300 |
| CCTGTATTTT | CGCGTATTTC | TGGAGAAATA | AAAGCCATCG | ATCAGTATGT | 350 |
| TGACAAAGAA | CTTTCCCCCA | TGTACGACAA | TTACGTAAAT | AAACCGTCGA | 400 |
| ACGATCCAAA | GCAGAAAAAC | AAACAGAAAC | TAATGATAAG | TGAACTACTT | 450 |
| TTACAACAGC | TTTTAAAATT | GGATGGAGTT | GACGTACTGG | GCAGCGAGAA | 500 |
| ATTGCGTTTT | GAACGGAAGC | AACTTGTTTC | TAAGATCCAA | AAAATGTTGG | 550 |
| ATCACGTTGA | CCAAACAAGC | CAAGAAGTGG | CCGCATAG | | 588 |

FIG. 8A

| | | | | | |
|---|---|---|---|---|---|
| MSEKTSTVTI | HYGNQRFPVA | VNLNETLSEL | IDDLLETTEI | SEKKVKLFYA | 50 |
| GKRLKDKKAS | LSKLGLKNHS | KILCIRPHKQ | QRGSKEKDTV | EPAPKAEAEN | 100 |
| PVFSRISGEI | KAIDQYVDKE | LSPMYDNYVN | KPSNDPKQKN | KQKLMISELL | 150 |
| LQQLLKLDGV | DVLGSEKLRF | ERKQLVSKIQ | KMLDHVDQTS | QEVAA | 195 |

FIG. 8B

```
ATGTCTTTTT  TTACCCAGTT  GTGTTCTATG  GATAAAAAAT  ATTGGATCTC   50
TCTAGCTGTA  TTGTCAGTTA  CTGTTTTGAT  TAGCGCATTA  TTGAAAAAGA  100
GAGCTACTGA  AACCGAAGAT  ATTGTCGTTG  TTCATTACGA  TGGCGAAAAG  150
TTGAATTTTG  TGTTGCGACA  ACCAAGGCTG  AATATGGTTT  CTTACACTAG  200
TTTTCTTCGT  CGCGTGTGCA  ACGCATTTTC  AGTAATGCCC  GACAAAGCGT  250
CTCTCAAGTT  AAACGGGGTG  ACCCTCAAGG  ATGGTTCACT  TTCCGACCAA  300
AATGTGCAAA  ATGGAAGTGA  ATTAGAGCTC  GAATTACCCA  AACTGAGCCC  350
GGCAATGCAA  CAAATTGAAG  CATATATAGA  TGAGCTTCAA  CAGGATCTCG  400
TCCCTAAAAT  TGAAGCCTTC  TGCCAATCGT  CTCCCGCTTC  GGCACAAGAT  450
GTTCAAGATT  TGCATACACG  CCTTAGTGAA  ACATTGTTGG  CTAGGATGAT  500
AAAATTAGAT  GCTGTTAATG  TTGAAGACGA  CCCAGAAGCT  CGTCTTAAAA  550
GAAAAGAAGC  TATTCGTTTA  TCTCAACAAT  ATTTGAGTAA  ACTAGATTCC  600
ACCAAGAATC  AAAACAAATG  A                                   621
```

FIG. 9A

| | | | | | |
|---|---|---|---|---|---|
| MSFFTQLCSM | DKKYWISLAV | LSVTVLISAL | LKKRATETED | IVVVHYDGEK | 50 |
| LNFVLRQPRL | NMVSYTSFLR | RVCNAFSVMP | DKASLKLNGV | TLKDGSLSDQ | 100 |
| NVQNGSELEL | ELPKLSPAMQ | QIEAYIDELQ | QDLVPKIEAF | CQSSPASAQD | 150 |
| VQDLHTRLSE | TLLARMIKLD | AVNVEDDPEA | RLKRKEAIRL | SQQYLSKLDS | 200 |
| TKNQNK | | | | | 206 |

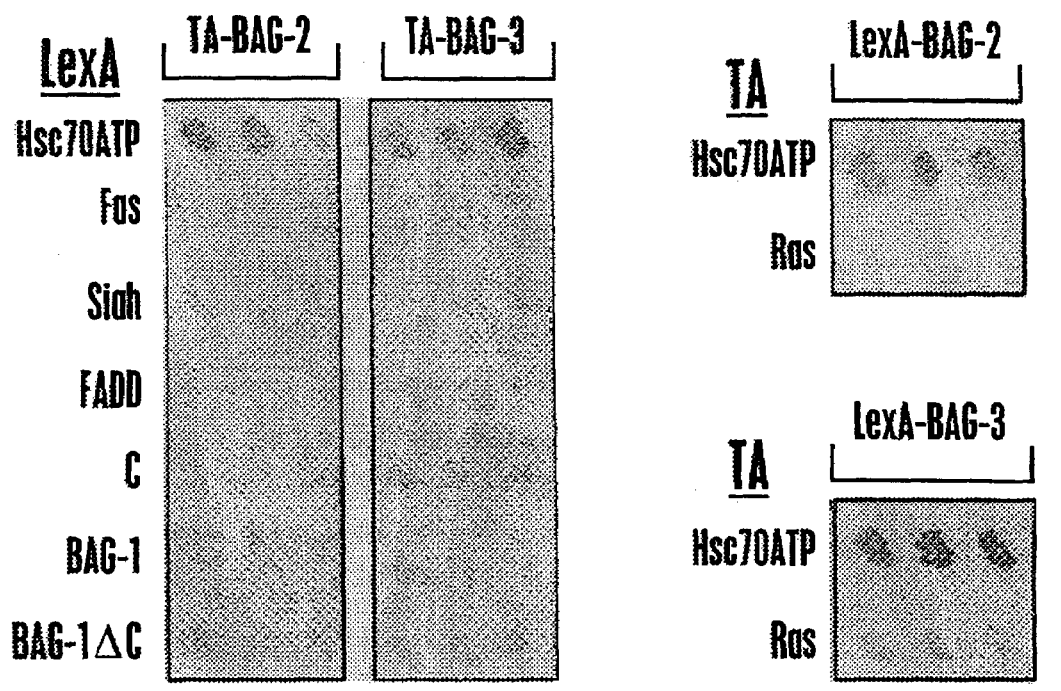
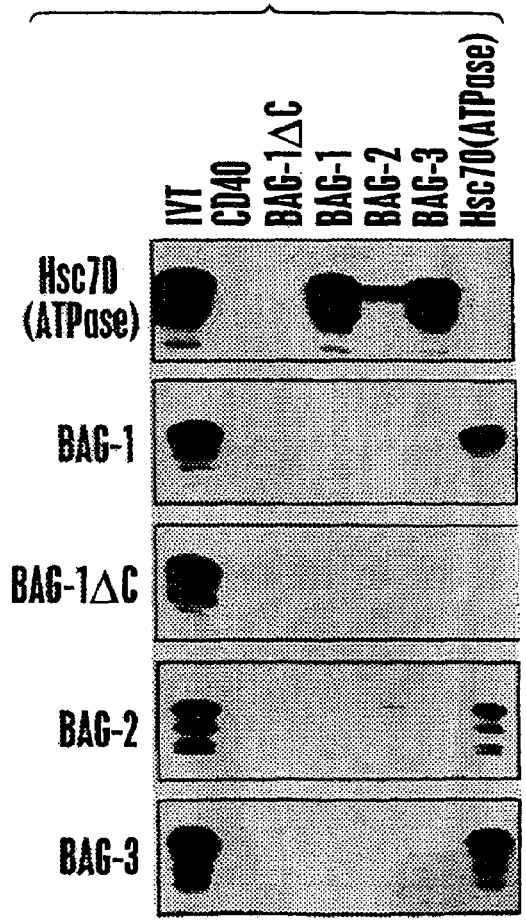
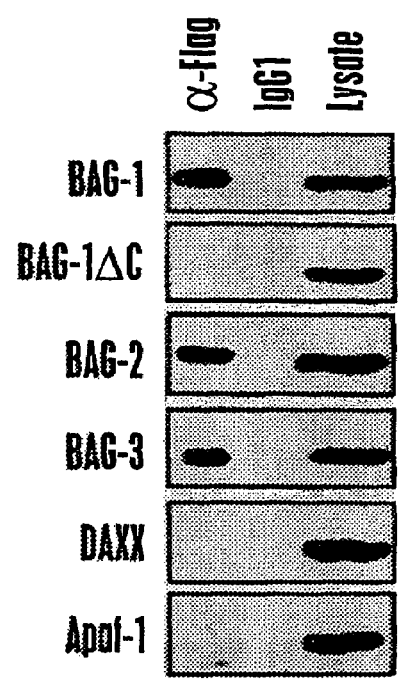
Fig. 11B
Fig. 11A
Fig. 11C

| | |
|---|---|
| GCGGAGCTCC GCATCCAACC CCGGGGCCGCG GCCAACTTCT CTGGACTGGA | 50 |
| CCAGAAGTTT CTAGCCGGCC AGTTGCTACC TCCCTTTATC TCCTCCTTCC | 100 |
| CCTCTGGCAG CGAGGAGGCT ATTTCCAGAC ACTTCCACCC CTCTCTGGCC | 150 |
| AGTCACCCCC CGCCTTTAAT TCATAAAGGT GCCCGGGGCC GGCTTCCCGG | 200 |
| ACACGTCGGC GGGGAGAGG GCCCACGGC GGCCACGGG CCAGAGACTC | 250 |
| GGCGCCCGGA GCGCGGCCGC CGCACGGGG CCCAGCGCG CAGACCCCAA | 300 |
| CCCAGCATGA GCGCGGCCAC CCACTCGCCC ATGATGCAGG TGGCGTCCGG | 350 |
| CAACGGTGAC CGCGACCCTT TGCCCCCCGG ATGGGAGATC AAGATCGAAC | 400 |
| CGCAGACCGG CTGGCCCTTC TTCGTGACC ACAACAGCCG CACCACTACG | 450 |
| TGGAACGACC CGCGGCGTGCC CTCGAGGGC CCCAAGGAGA CTCCATCCTC | 500 |
| TGCCAATGGC CCTTCCCGGG AGGGCTCTAG GCTGCCGCCT GCTAGGGAAG | 550 |
| GCCACCCTGT GTACCCCCAG CTCGACCAG GCTACATTCC CATTCCTGTG | 600 |
| CTCCATGAAG GCGCTGAGAA CCGGCAGGTG CACCCTTTCC ATGTCTATCC | 650 |
| CCAGCCTGGG ATGCAGCGAT TCCGAACTGA GGCGGCAGCA GCGGCTCCTC | 700 |
| AGAGGTCCCA GTCACCTCTG CGGGGCATGC CAGAAACCAC TCAGCCAGAT | 750 |
| AAACAGTGTG GACAGGTGGC AGCGGCGGCG GCAGCCCAGC CCCAGCCCTC | 800 |
| CCACGGACCT GAGCGGTCCC AGTCTCCAGC TGCCTCTGAC TGCTCATCCT | 850 |
| CATCCTCCTC GGCCAGCTCC CGGGGGGGTA CATCTCCATT CCGAGGAGCAG CCTGGCAGT | 900 |
| CACCAGCTCC CGCGGGGGTA CATCTCCATT CGGTGATAC ACGAGCAGAA | 950 |
| CGTTACCCGG CCAGAGCC AGCCCCTCCTT CCACAAAGCC CAGAAGACGC | 1000 |
| ACTACCCAGC GCAGAGGGGT GAGTACCAGA CCCACCACGCC TGTGTACCAC | 1050 |
| AAGATCCAGG GGGATGACTG GGAGCCCCGG CCCCTGCGGG CGGCATCCCC | 1100 |
| GTTCAGGTCA TCTGTCCAGG GTGCATGGG TCACCCGTGT GCACACGGCA | 1150 |
| GGAGCAGCAC GCCACTCCAC TCCCCCTCGC COATCCGTGT GCACACCGTG | 1200 |
| GTCGACAGGC CTCAGCAGCC CATGACCCAT CGAGAAACTG CACCTGTTTC | 1250 |
| CCAGCCTGAA AACAAACCAG AAAGTAAGCC AGGCCCAGTT GGACCAGAAC | 1300 |
| TCCCTCCTGG ACACATCCCA ATTCAAGTGA TCCGCAAAGA GGTGGATTCT | 1350 |

FIG. 15A

```
AAACCTGTTT CCCAGAAGCC CCCACCTCCC TCTGAGAAGG TAGAGGTGAA    1400
AGTTCCCCCT GCTCCAGTTC CTTGTCCTCC TCCCAGCCCT GGCCCTTCTG    1450
CTGTCCCCTC TTCCCCCAAG AGTGTGGCTA CAGAAGAGAG GGCAGCCCCC    1500
AGCACTGCCC CTGCAGAAGC TACACCTCCA AAACCAGGAG AAGCCGAGGC    1550
TCCCCAAAA CATCCAGGAG TGCTGAAAGT GGAAGCCATC CTGGAGAAGG     1600
TGCAGGGGCT GGAGCAGGCT GTAGACAACT TTGAAGGCAA GAAGACTGAC    1650
AAAAGTACC TGATGATCGA AGAGTATTTG ACCAAAGAGC TGCTGGCCCT     1700
GGATTCAGTG GACCCGAGG GACGAGCCGA TGTGCGTCAG GCCAGGAGAG     1750
ACGGTGTCAG GAAGGTTCAG ACCATCTTGG AAAAACTTGA ACAGAAAGCC    1800
ATTGATGTCC CAGGTCAAGT CCAGGTCTAT GAACTCCAGC CCAGCAACCT    1850
TGAAGCAGAT CAGCCACTGC AGCCAATCAT GGAGATGGGT GCCGTGGGCAG   1900
CAGACAAGGG CAAGAAAAAT GCTGGAAATG CAGAAGATCC CCACACAGAA    1950
ACCCAGCAGC CAGAAGCCAC AGCAGCAGCG ACTTCAAACC CCAGCAGCAT    2000
GACAGACACC CCTGGTAACC CAGCAGCACC GTAGCCTCTG CCCTGTAAAA    2050
ATCAGACTCG GAACCGATGT GTGCTTAGG GAATTTTAAG TTGCATGCAT     2100
TTCAGAGACT TTAAGTCAGT TGGTTTTTAT TAGCTGCTTG GTATGCAGTA    2150
ACTTGGGTGG AGGCAAAACA CTAATAAAAG GGCTAAAAAG GAAAATGATG    2200
CTTTCTTCT ATATTCTTAC TCTGTACAAA TAAAGAAGTT GCTTGTTGTT     2250
TGAGAAGTT AACCCGTTG CTTGTTCTGC AGCCCTGTCT ACTTGGGCAC      2300
CCCACCACC TGTTAGCTGT GGTTGTGCAC TGTCTTTTGT AGCTCTGGAC     2350
TGGAGGGGTA GATGGGGAGT CAATTACCCA TCACATAAAT ATGAAACATT    2400
TATCAGAAAT GTTGCCATTT TAATGAGATG ATTTTCTTCA TCTCATAATT    2450
AAAATACCTG ACTTAGAGA GAGTAAAATG TGCCAGGAGC CATAGGAATA     2500
TCTGTATGTT GGATGACTTT AATGCTACAT TTTC                     2534
```

FIG. 15B

```
MSAATHSPMM QVASGNGDRD PLPPGWEIKI DPQTGWPFFV DHNSRTTTWN     50
DPRVPSEGPK ETPSSANGPS REGSRLPPAR EGHPVYPQLR PGYIPIPVLH    100
EGAENRQVHP FHVYPQPGMQ RFRTEAAAAA PQRSQSPLRG MPETTQPDKQ   150
CGQVAAAAAA QPPASHGPER SQSPAASDCS SSSSSASLPS SGRSSLGSHQ    200
LPRGYISIPV IHEQNVTRPA AQPSFHKAQK THYPAQRGEY QTHQPVYHKI    250
QGDDWEPRPL RAASPFRSSV QGASSREGSP ARSSTPLHSP SPIRVHTVVD    300
RPQQPMTHRE TAPVSQPENK PESKPGPVGP ELPPGHIPIQ VIRKEVDSKP    350
VSQKPPPPSE KVEVKVPPAP VPCPPPSPGP SAVPSSPKSV ATEERAAPST    400
APAEATPPKP GEAEAPPKHP GVLKVEAILE KVQGLEQAVD NFEGKKTDKK    450
YLMIEEYLTK ELLALDSVDP EGRADVRQAR RDGVRKVQTI LEKLEQKAID    500
VPGQVQVYEL QPSNLEADQP LQAIMEMGAV AADKGKKNAG NAEDPHTETQ    550
QPEATAAATS NPSSMTDTPG NPAAP
                 575
```

```
GGGAGCTCC GCATCCAACC CCGGGCCGGG GCCAACTTCT CTGGACTGGA CCAGAAGTTT CTAGCCGGCC AGTTGCTACC TCCCTTTATC    90
TCTCCTTCC CCTCTGGCAG CGAGGAGGCT ATTTCCAGAC ACTTCCACCC CTCTCTGGCC AGTCACCCC CGCCTTTAAT TCATAAAGGT    180
GCCGGCCGCC GGCTTCCCGG ACACGTCGGC GGCGGAGAGG GGCCCCACCC GGCCCACGGC CCAGAGACTC GGCCCCGGA GCCAGCGCCC    270
CGGCACCCCG CCCCAGCGGG CAGACCCCCA GCCAGCCATGA GCGCCGCCAC CCACTCGCCC ATGATGCAGG TGGCGTCCGG CAACGGTGAC    360
                                          M  S  A  A  T  H  S  P  M  M  Q  V  A  S  G  N  G  D

CGGCACCCTT TGCCCCCCGG ATGGAGATC AAGATCGACC CGCAGACCGG CTGGCCCTTC TTCGTGGACC ACAACAGCCG CACCACTACG    450
R  D  P  L  P  P  G  W  E  I  K  I  D  P  Q  T  G  W  P  F  F  V  D  H  N  S  R  T  T  T

TGGAACGACC CGCGCGTGCC CCTGAGGGC CCCAAGGAGA TCCCATCCTC TGGCAATGGC AGGGCTCTAG CCTTCCCGGG AGTGCCCGCT    540
W  N  D  P  R  V  P  L  S  E  G  P  K  E  T  P  S  S  A  N  G  S  R  E  G  S  R  L  P  P

GCTAGGGAAG GCCACCCTGT GTACCCCCAG ATGCAGCGAT TCCGAACTGA GCTACTGTG CATTCTGTG GGCGGCAGCA CTCACCCTG    630
A  R  E  G  H  P  V  Y  P  Q  M  Q  R  F  R  T  E  L  H  E  G  I  P  V  L  H  E  G  A  E  N  R  Q  V

CACCCTTTC ATGTCTATCC CCAGCCTGGG ATGCAGCCAG TCCGAACTGA AACAGTGTG GACAGCCAGA GCCGGCAGCA GCGGGACCCT AGAGGTCCCA CTCACCCTG    720
H  P  F  H  V  Y  P  Q  P  G  M  Q  R  F  R  T  E  A  A  P  R  S  Q  S  P  L

CGGGGCATGC CAGAAACCAC TCAGCAGCAGAT AACAGTGTG GACAGCCAGA AGCGGCGGG AGCGCCCAGC CCCAGCCTC CCACGGACCT    810
R  G  M  P  E  T  T  Q  P  D  K  Q  C  G  Q  A  A  A  A  A  Q  P  A  S  H  G  P

GAGCGGTCCC AGTCTTCCAGC GCAGAGGGGT GAGTACCAGA CCCACCAGCC TGTGTACCAC GGGAGGGC AAGATCCAGG CCTGGGCAGT    900
E  R  S  A  S  P  A  A  S  Q  L  P  S  S  G  R  S  S  L  G  S

CACCAGCTCC CGGCATCCCC CATCTCCATT CCGGTGATAC ACGAGCAGA CGTTACCCGG CCCACCAGCC AGCCCTCCTT CCACAAAGCC    990
H  Q  L  P  R  G  Y  I  S  I  P  V  I  H  E  Q  N  V  T  R  P  A  A  Q  P  S  F  H  K  A

CAGAGAGAGC ACTACCCAGC GCAGAGGGGT GAGTACCAGA TGTGTACCAC CCGGAGGGC CATGACCAT CGAGAACTG GGATGACTGG    1080
Q  K  T  H  Y  P  A  Q  R  G  E  Y  Q  T  H  Q  P  V  Y  H  R  E  G  M  T  H  R  E  T  A  P  V  S  Q  P  E

GAGCGGTCCC AGTCTTCCAGC CATCTCCATT TGCCTCTGAC TGCTCATCCT GAGTACCAGA CGGTGATAC CTCAGGAGCC CATGACCAT CGAGAACTG GGATGACTGG    1170
E  R  S  A  S  P  A  R  S  S  T  P  L  H

CCCTGCGGG CGGCATCCCC GTTCAGGTCA GTGACAGGTG CTCAGGAGCC CGGGAGGGC AGAGCAGCA CCTGTTTC CCAGCCTGAA    1260
P  L  R  A  S  P  I  R  V  D  R  P  Q  Q  P  M  T  H  R  E  T  A  P  V  S  Q  P  E

TCCCCCTGC CCATCCGTGT GCACACCGTG GTGACAGGTG CTCAGGAGCC CATGACCAT CGAGAACTG CACCTGTTTC CCAGCCTGAA    1260
S  P  S  P  I  R  V  D  R  P  Q  Q  P  M  T  H  R  E  T  A  P  V  S  Q  P  E

AACAAACCAG AAAGTAAGCC AGGCCCAGTT GGACCAGAAC TCCCTCCTGG ACACATCCCA ATTCAAGTGA TCCGCAAAGA GGTGGATTCT    1350
N  K  P  E  S  K  P  G  P  V  G  P  E  L  P  P  G  H  I  P  I  Q  V  I  R  K  E  V  D  S
```

```
AAACCTGTTT CCCAGAAGCC CCCACCTCCC TCTGAGAAGG TAGAGGTGAA AGTTCCCCCT GTTCCAGTTC CTTGTCCTCC TCCCAGCCCT   1440
 K  P  V  S   Q  K  P   P  P  P   S  E  K  V   E  V  K   V  P  P   A  P  V   P  (  P  P   S  P
GGCCCTTCTG CTGTCCCCTC TTCCCCCAAG AGTGTGGCTA CAGAGAGAG GGCCAGCCCCC AGCACTGCCC CTGCAGAAGC TACACCTCCA   1530
 G  P  S  A   V  P  S   S  P  K   S  V  A   T  E  E  R   A  A  P   S  T  A   P  A  E  A   T  P  P
AAACCAGGAG AAGCCGAGGC TCCCCCCAAA CATCCAGGAG TGCTGAAAGT GGAAGCCATC CTGGAGAAGG TGCAGGGGCT GGAGCAGGCT   1620
 K  P  G  E   A  E  A   P  P  K   H  P  G  V   L  K  V   E  A  I   L  E  K  V   Q  G  L   E  Q  A
GTAGACAACT TTGAAGGCAA GAAGACTGAC AAAAAGTACC TGATGATCGA AGAGTATTTG ACCAAAGAGC TGCTGGCCCT GGATTCAGTG   1710
 V  D  N  F   E  G  K   K  T  D   K  K  Y  L   M  I  E   E  Y  L   T  K  E  L   L  A  L   D  S  V
GACCCCGAGG GACGAGCCGA TGTGCGGTCAG GCCGAGAGAG ACGGTGTCAG GAAGGTTCAG GAAGGTTCAG ACCATCTTGG AAAAACTTGA ACAGAAAGCC   1800
 D  P  E  G   R  A  D   V  R  Q   A  R  R  D   G  V  R   K  V  Q   T  I  L  E   K  L  E   Q  K  A
ATTGATGTCC CAGGTCAAGT CCAGGTCTAT GAACTCCAGC CCAGCAACCT TGAAGCAGAT CAGCCACTGC AGGCAATCAT GGAGATGGGT   1890
 I  D  V  P   Q  V  Q   V  Y  E   L  Q  P   S  N  L   E  A  D   Q  P  L  Q   A  I  M   E  M  G
GCCGTGGCAG CAGACAAGGG CAAGAAAAAT GCTGGAAATG CAGAAGATCC CCACACAGAA CAGCAGCACC AGCAGCAGCG AGCAGCAGCG   1980
 A  V  A  A   D  K  G   K  K  N   A  G  N  A   E  D  P   H  T  E   T  Q  Q  P   E  A  T   A  A  A
ACTTCAAACC CCAGCAGCAT GACAGACACC CCTGGTAACC CAGCAGCACC CTAGCCTCTG CCCTGTAAAA ATCAGACTCG GAACCGATGT   2070
 T  S  N  P   S  S  M   T  D  T   P  G  N  P   A  A  P
GTGCTTTAGG GAATTTTAAG TTGCATGCAT TTCAGAGACT TTAAGTCAGT TGGTTTTTAT TAGCTGCTTG GTATGCAGTA ACTTGGGTGG   2160
AGGCAAAACA CTAATAAAAG GGCTAAAAAG GAAAATGATG CTTTTCTTCT ATATTCTTAC TCTGTACAAA TAAAGAAGTT GCTTGTTGTT   2250
TGAGAAGTTT AACCCCGTTG CTTGTTCTGC AGCCCTGTCT ACTTGGGCAC CCCCACCACC TGTTAGCTGT GGTTGTGCAC TGTCTTTGT   2340
AGCTCTGGAC TGGAGGGGTA GATGGGGAGT CAATTACCCA TCACATAAAT ATGAAACATT TATCAGAAAT GTTGCCATTT TAATGAGATG   2430
ATTTCTTCA TCTCATAATT AAAATACCTG ACTTTAGAGA GAGTAAAAATG TGCCAGGAGC CATAGGAATA TCTGTATGTT GGATGACTTT   2520
AATGCTACAT TTTC
```

Fig.15E

```
CGGTGGGAGC GGGGGGGGAA GCGGCTTCAGG GCAGCGGGATC CCATGTCGGC      50
CCTGAGGCGC TCGGGCTACG GCCCCAGTGA CGGTCCGTCC TACGGCCGCT       100
ACTACGGCCT CTGGGGGTGGA GATGTGCCGG TACACCCACC TCCACCCTTA      150
TATCCTCTTC GCCCTGAACC TCCCCAGCCT CCCATTTCCT GGCGGGGTGCG      200
CGGGGCGGC CCGGCGGGAGA CCAACTGGCT GGGAGAAGGC GGAGGAGGCG       250
ATGGGCTACTA TCCCTCGGGA GGGCGCCTGGC CAGAGCCTGG TCGAGCCGGA     300
GGAAGCCACC AGGAGCAGCC ACCATATCCT AGTACAACAATT CTAACTATTG     350
GAATTCTACT GCGAGATCTA GGGCTCCTTA CCCAAGTACA TATCCTGTAA       400
GACCAGAATT GCAAGGCCAG AGTTTGAATT CTTATACAAA TGGAGCGTAT       450
GGTCCAACAT ACCCCCAGG CCCTGGGGCA AATACTGCCT CATACTCAGG        500
GGCTTATTAT GCACCTGGTT ATACTCAGAC CAGTTACTCC ACAGAAGTTC       550
CAAGTACTTA CCGTTCATCT GGCAACAGCC CAACTCCAGT CTCTCGTTGG      600
ATCTATCCCC AGCAGGACTG TCAGACTGAA GCACCCCTC TTAGGGGGCA        650
GGTTCCAGGA TATCCGCCT CACAGAACCC TGGAATGACC CTGCCCATT         700
ATCCTTATGG AGATGGTAAT CGTAGTGTTC CACAATCAGG ACCGACTGTA      750
CGACCACAAG AAGATGCGTG GGCTTCTCCT GGTGCTTATG GAATGGGTGG      800
CCGTTATCCC TGGCCTTCAT CAGCGCCCCTC AGCACCACCC GGCAATCTCT      850
ACATGACTGA AAGTACTTCA CCATGGCCTA GCAGTGGCTC TCCCCAGTCA       900
CCCCCTTCAC CCCCAGTCCA GCAGCCCAAG GATTCTTCAT ACCCCTATAG      950
CCAATCAGAT CAAAGCATGA ACGGGCACAA CTTTCCTTGC AGTGTCCATC     1000
AGTAGCAATC CTCGGGGACA GTGATCAATG AAGATTCAGA TCTTTTGGAT     1050
TCCCAAGTCC AGTATAGTGC TGAGCCTCAG CTGTATGGTA ATGCCACCAG     1100
TGACCATCCC AACAATCAAG ATCAAAGTAG CAGTCTTCCT GAAGAATGTG     1150
TACCTTCAGA TGAAAGTACT CCTCCGAGTA TTAAAAAAT CATACATGTG      1200
CTGGAGAAGG TCCAGTATCT TGAACAAGAA GTAGAAGAAT TTGTAGGAAAA    1250
AAAGACAGAC AAAGCATACT GGCTTCTGGA AGAAATGCTA ACCAAGGAAC     1300
```

FIG. 16A

```
TTTTGGAACT GGATTCAGTT GAAACTGGGG GCCAGGACTC TGTACGGCAG     1350
GCCAGAAAAG AGGCTGTTTG TAAGATTCAG GCCATACTGG AAAAATTAGA     1400
AAAAAAGGA TTATGAAAGG ATTTAGAACA AAGTGGAAGC CTGTTACTAA     1450
CTTGACCAAA GAACACTTGA TTAGGTAAT TACCCTCTTT TTGAAATGCC     1500
TGTTGATGAC AAGAAGCAAT ACATTCCAGC TTTTCCTTTG ATTTTATACT     1550
TGAAAACTG GCAAAGGAAT GGAAGAATAT TTTAGTCATG AAGTTGTTTT     1600
CAGTTTTCAGA CGAATGAATG TAATAGGAAA CTATGGAGTT ACCAATATTG    1650
CCAAGTAGAC TCACTCCTTA AAAAATTTAT GGATATCTAC AAGCTGCTTA     1700
TTACCAGCAG GAGGGAAACA CACTTCACAC AACAGGCTTA TCAGAAACCT     1750
ACCAGATGAA ACTGGATATA ATTGAGACA AACAGGATGT GTTTTTTAA       1800
ACATCTGGAT ATCTTGTCAC ATTTTGTAC ATTGTGACTG CTTTCAACAT      1850
ATACTTCATG TGTAATTATA GCTAGACTT TAGCCTTCTT GGACTTCTGT      1900
TTGTTTTGT TATTTGCAGT TTACAAATAT AGTATTATTC TCTAAAAAA       1950
AAAAAAAAA AAAAAA                                            1966
```

FIG. 16B

MSALRRSGYGPSDGPSYGRYYGPGGGDVPVHPPPPLYPLRPEPPQPPISWRVRGGGPAETTWLGEGGGDGYYPSGGAWP
EPGRAGGSHQEQPPYPSYNSNYWNSTARSRAPYPSTYPVRPELQGQSLNSYTNGAYGPTYPPGPGANTASYSGAYYAPGY
TQTSYSTEVPSTYRSSGNSPTPVSRMYPQQDCQTEAPPLRGQVPGYPPSQNPGMTLPHYPYGDGNRSVPQSGPTVRPQE
DAWASPGAYGMGGRYPWPSSAPSAPPGNLYMTESTSPWPSSGSPQSPPVQQPKDSSYPYSQSDQSMNRHNFPCSVHQ
YESSGTVINEDSDLLDSQVQYSAEPQLYGNATSDHPNNQDQSSSLPEECVPSDESTPPSIKKIIHVLEKVQYLEQEVEEF
VGKKTDKAYWLLEEMLTKELLELDSVETGGQDSVRQARKEAVCKIQAILEKLEKKGL

FIG. 16C

```
CGGTGGGAGC GGGGCGGGAA GCGCTTCAGG GCAGCGGATC CCATGTCGGC CCTGAGGCGC TCGGGCTACG GCCCCAGTGA CGGTCCGTCC    90
                                        M   S   A   L   R   R   S   G   Y   G   P   S   D   G   P   S
TACGGGCCGCT ACTACGGGGCC TGGGGGTGGA GATGTGCCGG TACACCCCACC TCCACCCTTA TATCCTCTTC GCCCTGAACC TCCCCAGCCT  180
 Y   G   R   Y   Y   G   P   G   G   G   D   V   P   V   H   P   P   P   L   Y   P   L   R   P   E   P   P   Q   P
CCCATTTCCT GGCGGGTGCG CGGGGGCGGC CCGGCGGAGA CCACCTGGCT GGGAGAAGGC GGAGGAGGCG ATGGCTACTA TCCCTCGGGA  270
 P   I   S   W   R   V   R   G   G   G   P   A   E   T   T   W   L   G   E   G   G   G   D   G   Y   Y   P   S   G
GGCGCCTGGC CAGAGCCTGG TCGAGCCCGGA GGAAGCCACC AGGAGCCAGCC ACCATATCCT AGCTACAATT CTAACTATTG GAATTCTACT  360
 G   A   W   P   E   P   G   R   A   G   G   S   H   Q   E   Q   P   Y   P   S   Y   N   S   N   Y   W   N   S   T
GCGAGATCTA GGGCTCCTTA CCCAAGTACA TATCCTGTAA GACCAGAATT GCAAGGCCAG AGTTTGAATT CTTATACAAA TGGAGCGTAT    450
 A   R   S   R   A   P   Y   P   S   T   Y   P   V   R   P   E   L   Q   G   Q   S   L   N   S   Y   T   N   G   A   Y
GGTCCAACAT ACCCCCCAGG CCCTGGGGCA AATACTGCCT CATACTCAGG GGCTTATTAT GCACCTGGTT ATCCTCAGAC CAGTTACTCC    540
 G   P   T   Y   P   P   G   P   G   A   N   T   A   S   Y   S   G   A   Y   Y   A   P   G   Y   P   Q   T   S   Y   S
ACAGAAGTTC CAAGTACTTA CCGTTCATCT GGCAACAGCC CAACTCCAGT CCCTCGTTGG ATCCTATCCCC AGCAGGACTG TCAGACTGAA    630
 T   E   V   P   S   T   Y   R   S   S   G   N   S   P   T   P   V   S   R   W   I   Y   P   Q   D   C   Q   T   E
GCACCCCCTC TTAGGGGCA GGTTCCAGGA TATCCGCCTT CACAGAACCC TGGAATGACC CTGCCCCATT ATCCTTATGG AGATGGTAAT   720
 A   P   P   L   R   G   Q   V   P   G   Y   P   P   S   Q   N   P   G   M   T   L   P   H   Y   P   Y   G   D   G   N
CGTAGTGTTC CACAATCAGG ACCGACTGTA CGACCACAAG AAGATGCCGTG GCCTTCTCCT GGTGCTTATG GAATGGGTGG CCGTTATCCC   810
 R   S   V   P   Q   S   G   P   T   V   R   P   Q   E   D   A   W   A   S   P   G   A   Y   G   M   G   G   R   Y   P
```

Fig. 16D

```
TGGCCTTCAT CAGGGCCCTC AGCACCACCC GGCAATCTCT ACATGACTGA AAGTACTTCA CCATGGCCTA GCAGTGGCTC TCCCCAGTCA    900
 W  P  S  S   Q  G  P   A  P  S    A  P  P    G  N  L  Y   M  T  E    S  T  S    P  W  P   S  G  S   P  Q  S
CCCCCTTCAC CCCAGTCCA GCAGCCCAAG GATTCTTCAT ACCCCTATAG CCAATCAGAT CAAAGCATGA ACCGGCACAA CTTTCCTTGC    990
 P  P  S  P   P  V  Q   Q  P  K    D  S  S  Y  P  Y  S    Q  S  D    Q  S  M  N   R  H  N    F  P  C
AGTGTCCATC AGTACGAATC CTCGGGGACA GTGATCAATG AAGATTCAGA TCTTTTGGAT TCCCAAGTCC AGTATAGTGC TGAGCCCTCAG  1080
 S  V  H  Q   Y  E  S   S  G  T    V  I  N  E   D  S  D    L  L  D    S  Q  V  Q   Y  S  A    E  P  Q
CTGTATGGTA ATGCCACCAG TGACCATCCC AACAATCAAG ATCAAAGTAG CAGTCTTCCT GAAGAATGTG TACCTTCAGA TGAAAGTACT  1170
 L  Y  G  N   A  T  S   D  H  P    N  N  Q  D   Q  S  S    S  L  P    E  E  C  V   P  S  D    E  S  T
CCCTCGAGTA TTAAAAAAAT CATACACATGTG CTGGAGAAGG TCCAGTATCT TGAACAAGAA GTAGAAGAAT TTGTAGGAAA AAAGACAGAC  1260
 P  P  S  I   K  K  I   H  V  L  E  K  V  Q  Y  L    E  Q  E    V  E  E  F   V  G  K    K  T  D
AAAGCATACT GGCTTCTGGA AGAAATGCTA ACCAAGGAAC TTAAGGAACT GGATTCAGTT GAAACTGGGG GCCAGGACTC TGTACGGCAG   1350
 K  A  Y  W   L  L  E   E  M  L    T  K  E  L   L  E  L    D  S  V    E  T  G  G   Q  D  S    V  R  Q
GCCAGAAAAG AGGCTGTTTG TAAGATTCAG GCCATACTGG AAAAATTAGA AAAAAAAGGA TTATGAAAGG ATTTAGAACA AAGTGGAAGC   1440
 A  R  K  E   A  V  C   K  I  Q    A  I  L    E  K  L    E  K  K  G   L
CTGTTACTAA CTTGACCAAA GAACACTTGA TTAGGTTAAT TACCCTCTTT TTGAAATGCC TGTTGATGAC AAGAAGCAAT ACATTCCAGC   1530
TTTTCCTTTG ATTTTATACT TGAAAACTG GCAAAGGAAT GGAAGAATAT TTTAGTCATG AAGTTGTTT CAGTTTTCAG ACGAATGAATG   1620
TAATAGGAAA CTATGGAGTT ACCAATATTG CCAGTAGAC TCACTCCTTA AAAAATTTAT GGATATCTAC AAGCTGCTTA TTACCAGCAG    1710
GAGGGAAACA CACTTCACAC AACAGGCTTA TCAGAAACCT TCAGAATGAA ACTGGATATA ATTTGAGACA AACAGGATGT GTTTTTTAA    1800
ACATCTGGAT ATCTTGTCAC ATTTTGTAC ATTGTGACTG CTTTCAACAT ATACTTCATG TGTAATTATA GCTTAGACTT TAGCCCTCTT    1890
GGACTTCTGT TTTGTTTGT TATTTGCAGT TTACAAATAT AGTATTATTC TCTAAAAAAA AAAAAAAAA AAAAA                     1980
```

```
CCCCCCCCCC CCCCCCCCC CCNGAAGACG CCCGGAGCGG CTGCTGCAGC         50
CAGTAGCGGC CCCTTCACCG GCTGCCCCGC TCAGACCTAG TCGGGAGGGG        100
TGCGAGGCAT GCAGGTGGGG GCCCAGCTCC GGTGCGCGAC CCCGTAAAGG        150
GCTGATCTTC CACCTCGCCA CCTCAGCCAC GGGACGCCAA GACCGCATCC        200
AATTCAGACT TCTTTGGTG CTTGTGAAAC TGAACACAAC AAAGTATGG          250
ATATGGGAAA CCAACATCCT TCTATTAGTA GGCTTCAGGA AATCCAAAAG        300
GAAGTAAAAA GTGTAGAACA GCAAGTTATC GGCTTCAGTG GTCTGTCAGA        350
TGACAAGAAT TACAAGAAAC TGGAGAGGAT TCTAACAAAA CAGCTTTTTG        400
AAATAGACTC TGTAGATACT GAAGGAAAAG GAGATATTCA GCAAGCTAGG        450
AAGCGGGCAG CACAGGAGAC AGAACGTCTT CTCAAGAGT TGGAGCAGAA         500
TGCAAACCAC CCACACCGGA TTGAAATACA GAACATTTTT GAGGAAGCCC        550
AGTCCCTCGT GAGAGAGAAA ATTGTGCCAT TTTATAATGG AGGCAACTGC        600
GTAACTGATG AGTTTGAAGA AGGCATCCAA GATATCATTC TGAGGCTGAC        650
ACATGTTAAA ACTGGAGGAA AAATCTCCTT GCGGAAAGCA AGGTATCACA        700
CTTTAACCAA AATCTGTGCG GTGCAAGAGA TAATCGAAGA CTGCATGAAA        750
AAGCAGCCTT CCCTGCCGCT TTCCGAGGAT GCACATCCTT CCGTTGCCAA        800
AATCAACTTC GTGATGTGTG AGGTGAACAA GGCCCGAGGG GTCCTGATTG        850
CACTTCTGAT GGGTGTGAAC AACAATGAGA CCTGCAGGCA CTTATCCTGT        900
GTGCTCTCGG GGCTGATCGC TGACCTGGAT GCTCTAGATG TGTGCGGCCG        950
GACAGAAATC AGAAATTATC GGAGGGAGGT AGTAGAAGAT ATCAACAAAT       1000
TATTGAAATA TCTGGATTTG GAAGAGGAAG CAGACACAAC TAAAGCATTT       1050
GACCTGAGAC AGAATCATTC CATTTTAAAA ATAGAAAAGG TCCTCAAGAG       1100
AATGAGAGAA ATAAAAAATG AACTTCTCCA AGCACAAAAC CCTTCTGAAT       1150
TGTACCTGAG CTCCAAAACA GAATTGCAGG GTTTAATTGG ACAGTTGGAT       1200
GAGGTAAGTC TTGAAAAAAA CCCCTGCATC CGGGAAGCCA GGAGAAGAGC       1250
AGTGATCGAG GTGCAAACTC TGATCACATA TATTGACTTG AAGGAGGCCC       1300
```

FIG. 17B

```
TTGAGAAAAG AAAGCTGTTT GCTTGTGAGG AGCACCCATC CCATAAAGCC        1350
GTCTGGAACG TCCTTGGAAA CTTGTCTGAG ATCCAGGGAG AAGTTCTTTC        1400
ATTTGATGGA AATCGAACCG ATAAGAACTA CATCCGGCTG GAAGAGCTGC        1450
TCACCAAGCA GCTGCTAGCC CTGGATGCTG TTGATCCGCA GGGAGAAGAG        1500
AAGTGTAAGG CTGCCAGGAA ACAAGCTGTG AGGCTTGCGC AGAATATTCT        1550
CAGCTATCTC GACCTGAAAT CTGATGAATG GGAGTACTGA AATACCAGAG        1600
ATCTCACTTT TGATACTGTT TTGCACTTCA TATGTGCTTC TATGTATAGA        1650
GAGCTTTCAG TTCATTGATT TATACGTGCA TATTTCAGTC TCAGTATTTA        1700
TGATTGAAGC AAATTCTATT CAGTATCTGC TGCTTTTGAT GTTGCAAGAC        1750
AAATATCATT ACAGCACGTT AACTTTTCCA TTCGGATCAT TATCTGTATG        1800
ATGTGGTGTG GTTGTTGG TTTGTCCTT TTTTGCGT TTAATCAGA              1850
AAACAAAATA GAGGCAGCTT TTGTAGATTT TAAATGGGTT GTGCAAGCAT        1900
TAAAATGCAG GTCTTTCAGA ATCTAGAACT AGGCATAACC TTACATAATA        1950
CTAGGAAAAT TATGAGAAAG GGGAAATTTT TGGTTAAATA AGAGTAAGGT        2000
TCAAACACAA GCAGTACATG TTCTGTTTCA TTATGCTCGA TAGAAGGCTT        2050
TTTTTCACT TATAAGGCCT GATTGGTCCT ACCAGCTTA ACGGGGTGGG          2100
GTTTTTTGT TTGTTCAGAC AGTCTGTTCT TTTGTAAACA TTTTAGTTG          2150
GAAAAACAGC ATCTGCATTT TCCCCATCCT CTACGTTTTA GAGAGGAATC        2200
TGTTTTTGT GTGCAACATA AGAAAATTAT GAAAACTAAT AGCCAAAAAA         2250
CCTTTGAGAT TGCATTAAAG AGAAGGGATA AAGGACCAGC AATAATACCT        2300
TGTAAGTTGC TTTTGTTTGT AAATCTGAG CTTATAGTTT TCCTTAGTGA         2350
GTAAATTCAT AAGGATGGA ACATTTAAAT TAAGTTAATG GGCCTTTAAA         2400
AAAAAAAAG GAAACACTCA TACCTGTAGT TGGAGGATGA ATACTGGAGA         2450
CGGGTACCA ATGTCAGGTT ATACTAAAAC TAAATCAGAA AGTCTGAATG         2500
TAGCACATAA TGGTTCTCTT CTGTGTCCA AGGCTGTAAA ATGGACAGCC         2550
TTGTCACACC TCCCGGTGC TGTTTTACAA CGTGAGGGTA GACGCTGTCA         2600
```

FIG. 17C

```
GTAACCCAGA GGGACCAGGC CTTCCTAGGT TTTCTAGGCA GTCAGCTGTT    2650
AACCACTCAC TTAGTAAATG TCATAACTAC ACCTGCTCCA GGACCAATCA    2700
GTGAAACCTG CTCGGAATTA AAGGCTTCCT CTGGGTGCCT GCTGAACAAC    2750
TGAGCTCATG TCATGGGCAT GTGGTGGTTT CTCTGTTGCC TGAAAGAGCC    2800
ATTAAAGTCA GTCGTGCGTG AAGCATCTCT CTTCTAAAGG ATGTGTATTT    2850
CCATAAATGC TTTCTGAGGA TCCGGTACAA AATGATTTCC CAAAGTTCTG    2900
AAGTGCCTTG AGAACATGTG GGTCCGAGTG TTATAACAGA CTCCTCCCCC    2950
GGGTCACCTT TGCCTGGTC ATCCTGTTAG AGTACATCTT TGGAAATCCA    3000
GGGTAATATT CTCTTTCAGA GATGCTCATT GTGTAACTCT GTGTAGGGAG    3050
ATAGTCACTT TAAACAGCTC AAAGTAGCTA GCTAAAGGAG TAGCCTTAAA    3100
TACCTAAAAG ATGACAGAAG CATAGCCCTT AACAAATCTT CAGCTTGTCT    3150
CTCAGTATTT CCCAATCATG AAAATCCCTT GCTATGTCTT TCCTACTAGA    3200
AATGTTCTAG AATCGCTGGA CGGTGGGGTC AGAGGGCAGT CGGTATTTAG    3250
GCCGTGAGCT TCCCATACTA CTGCAGGTCC AACTCCTGGC AACCGCGGGC    3300
TCAAGGCAGG TCATTGGAAT CCACGTTTTG GCCACAGTAG TTGTAGGATT    3350
GCTTTCTGT ATCATAATTT TAGAATGCTC TTAAAATCTT GAGGAAGAGT    3400
TTTTATTTT TATTTATTTT TGAGATGGAG TCTCTGTTGC CCAGGCTGCA    3450
GTGCAGTGGT GCCATCTCAG CTCACTGCAA CCTCCACCTC CCAGGTTCAA    3500
GCGATTCTCC TGCCTCAGCC ACCTGAGTAG CTGGGAGTAC AGGCATGTGG    3550
CACCATGCCT GGCTAATTTT TGTATTTTTA ATAGAGTTGA GATTTCACCA    3600
TGATGGTCAG GCTGGTCTCG AACTCCTGAC CTCGTGATCC GCCCGCCTCG    3650
GCCCCCAAA GTGCTGGGAT TAACGGGTGT GAGCCACGGC GCCCAGCCCA    3700
GGAAGAGTTT TTAAATTAGA GCTCTGTTTA ATTATACCAC TGGGAAATCA    3750
TGGTTACGCT TCAGGCATAT TCTTCCCCAG AGTACTACTT ACATTTTAAA    3800
TTTCATTTTG TAAAGTTAAA TGTCAGCATT CCCTTTAAAA GTGTCCATTG    3850
TTCTTTGAAA GTAGACGTTT CAGTCATTCT TTTCAAACAA GTGTTTGTGT    3900
```

```
ACCTTTTGCC AAGCTGTGGG CATCGTGTGT GAGTACAGGG TGCTCAGCTC    3950
TTCCACCGTC ATTTGAATT GTTCACATGG GTAATTGGTC ATGGAAATGA     4000
TCAGATTGAC CTTGATTGAC TGTCAGGCAT GGCTTTGTTT CTAGTTTCAA    4050
TCTGTTCTCG TTCCTTGTAC CGGATTATTC TACTCCTGCA ATGAACCCTG    4100
TTGACACGG ATTAGCTCT TGTCGGCCTT CGTGGGGAGC TGTTTGTGTT      4150
AATATGAGCT ACTGCATGTA ATTCTTAAAC TGGGCTTGTC ACATTGTATT    4200
GTATTTTGT GATCTGTAAT GAAAAGAATC TGTACTGCAA GTAAAACCTA     4250
CTCCCCAAAA ATGTGTGGCT TTGGGTCTGC ATTAAACGCT GTAGTCCATG    4300
TTCATGCC                                                  4308
```

FIG. 17D

```
MDMGNQHPSI SRLQEIQKEV KSVEQQVIGF SGLSDDKNYK KLERILTKQL      50
FEIDSVDTEG KGDIQQARKR AAQETERLLK ELEQNANHPH RIEIQNIFEE     100
AQSLVREKIV PFYNGGNCVT DEFEEGIQDI ILRLTHVKTG GKISLRKARY    150
HTLTKICAVQ EIIEDCMKKQ PSLPLSEDAH PSVAKINFVM CEVNKARGVL    200
IALLMGVNNN ETCRHLSCVL SGLIADLDAL DVCGRTEIRN YRREVVEDIN    250
KLLKYLDLEE EADTTKAFDL RQNHSILKIE KVLKRMREIK NELLQAQNPS    300
ELYLSSKTEL QGLIGQLDEV SLEKNPCIRE ARRRAVIEVQ TLITYIDLKE    350
ALEKRKLFAC EEHPSHKAVW NVLGNLSEIQ GEVLSFDGNR TDKNYIRLEE    400
LLTKQLLALD AVDPQGEEKC KAARKQAVRL AQNILSYLDL KSDEWEY       447
```

```
CCCCCCCCC CCCCCCCCC CCNGAGACG CCCGGAGCGG CTGCTGCAGC CTGCTGCAGC CAGTAGCGGC CCCTTCACCG GCTGCCCCGC TCAGACCTAG      90
TCGGAGGGG TGGGAGGCAT GCAGCTGGGG GCCCAGCTCC GGTGCCGCAC CCCGTAAAGG GCTGATCTTC CACCTGGCCA CCTCAGCCAC              180
GGGACGCCAA GACCGCATCC AATTCAGATC TCTTTTGGTG CTTGTGAAAC TGAACACAAC AAAAGTATGG ATATGGGAAA CCAACATCCT              270
                                                                    M  D  M  G  N   Q  H  P

TCTATTAGTA GGCTTCAGGA AATCCAAAAG GAAGTAAAAA GCAAGTTATC GGCTTCAGTG GTCTGTCAGA TGACAAGAAT                        360
 S  I  S  R  L  Q  E   I  Q  K  E  V  K  S   V  E  Q  Q  V  I   G  F  S  G  L  S  D   D  K  N

TACAAGAAAC TGGAGAGGAT TCTAACAAAA CAGCTTTTTG AAATAGACTC TGTAGATACT GAAGGAAAAG GAGATATTCA GCAAGCTAGG              450
 Y  K  K  L  L  E  R  I  L  T  K   Q  L  F  E  I  D  S   V  D  T   E  G  K  G  D  I  Q  Q  A  R

AAGGGGCAG CACAGAGAC AGAACGTCTT CTCAAGAGT TGGAGCAGAA TGCACACCAC CCACACCGGA TTGAAATACA GAACATTTTT                 540
 K  R  A  A  Q  E  T  R  L  L  K  E  L  E   Q  N  A  N  H   P  H  R  I  E  I  Q   N  I  F

GAGGAGCCC AGTCCCTCGT GAGAGAGAAA ATTGTGCCAT TTTATAATGG AGGCAACTGC GTAACTGATG AGTTGAAGA AGGCATCCAA                630
 E  E  A  Q   S  L  V  R  E  K   I  V  P  F  Y  N  G   G  N  C   V  T  D  E  F  E  E   G  I  Q

GATATCATTC TGAGGCTGAC ACATGTTAAA ACTGGGAAGA AAATCTCCTT GCGGAAAGCA AGGTATCACA CTTAACCAA AATCTGTGCG               720
 D  I  I  L  R  L  T   H  V  K   T  G  G  K   I  S  L   R  K  A  R  Y  H  T   L  T  K  I  C  A

GTGCAAGAGA TAATCGAAGA CTGCATGAAA AAGCAGCCTT CCCTGCCGCT TTCCGAGGAT GCACATCCTT CGGTTGCCAA AATCAACTTC              810
 V  Q  E  I  E  D   C  M  K   K  Q  P  S  L  P  L   S  E  D   A  H  P  S   V  A  K  I  N  F

GTGATGTGTG AGGTGAACAA GGCCCGAGGG GTCCTGATTG CACTTTCTGAT GGGTGTGAAC AACAATGAGA CCTGCAGGCA CTTATCCTGT             900
 V  M  C  E  V  N  K   A  R  G   V  L  I  A  L  L  M   G  V  N   N  N  E  T   C  R  H  L  S  C

GTGCTCTCGG GGCTGATCGC TGACCTGGAT GCTCTAGATG TGTGGCGCCG GACAGAAATC AGAAATTATC GGAGGGAGGT AGTAGAAGAT              990
 V  L  S  G  L  I  A   D  L  D   A  L  D  V   C  G  R   T  E  I   R  N  Y  R   R  E  V  E  D

ATCAACAAAT TATTGAAATA TCTGGATTTG GAAGAGGAAG CAGACACAAC TAAAGCATTT GACCTGAGAC AGAATCATTC CATTTTAAAA             1080
 I  N  K  L  L  K  Y   L  D  L   E  E  E  A   D  T  T   K  A  F   D  L  R  Q   N  H  S  I  L  K
```

Fig. 17G

```
ATAGAAAAGG TCCTCAAGAG AATGAGAGAA ATAAAAAATG AACTTCTCCA AGCACAAAAC CCTTCTGAAT TGTACCTGAG CTCCAAAACA   1170
 I  E  K  V  L  K  R     M  R  E     I  K  N  E     L  L  Q     A  Q  N     P  S  E  L     Y  L  S     S  K  T
GAATTGCAGG GTTTAATTGG ACAGTTGGAT GAGGTAAGTC TTGAAAAAAA CCCCTGCATC CGGAAGCCA GGAGAAGAGC AGTGATCGAG   1260
 E  L  Q  G  L  I  G  Q  L  D  E  V  S  L  E  K  N  P  C  I  R  E  A  R  R  R  A  V  I  E
GTGCAAACTC TGATCACATA TATTGACTTG AAGGAGGCCC TTGAGAAAAG AAAGCTGTTT GCTTGTGAGG AGCACCCATC CCATAAAGCC   1350
 V  Q  T  L  I  T  Y  I  D  L  K  E  A  L  E  K  R  K  L  F  A  C  E  E  H  P  S  H  K  A
GTCTGGAACG TCCTTGGAAA CTTGTCTGAG ATCCAGGGAG AAGTTCTTTC ATTTGATGGA AATCGAACCG ATAAGAACTA CATCCGGCTG   1440
 V  W  N  V  L  G  N  L  S  E  I  Q  G  E  V  L  S  F  D  G  N  R  T  D  K  N  Y  I  R  L
GAATTGCAGG GTTTAATTGG ACAGTTGGAT GAGGTAAGTC TTGAAAAAAA CCCCTGCATC CGGGAAGCCA GGAGAAGAGC AGTGATCGAG   1260
 E  L  Q  G  L  I  G  Q  L  D  E  V  S  L  E  K  N  P  C  I  R  E  A  R  R  R  A  V  I  E
GTGCAAACTC TGATCACATA TATTGACTTG AAGGAGGCCC TTGAGAAAAG AAAGCTGTTT GCTTGTGAGG AGCACCCATC CCATAAAGCC   1350
 V  Q  T  L  I  T  Y  I  D  L  K  E  A  L  E  K  R  K  L  F  A  C  E  E  H  P  S  H  K  A
GTCTGGAACG TCCTTGGAAA CTTGTCTGAG ATCCAGGGAG AAGTTCTTTC ATTTGATGGA AATCGAACCG ATAAGAACTA CATCCGGCTG   1440
 V  W  N  V  L  G  N  L  S  E  I  Q  G  E  V  L  S  F  D  G  N  R  T  D  K  N  Y  I  R  L
GAAGAGCTGC TCACCAAGCA GCTGCTAGCC CTGGATGCTG TGATCCGGA GGGAGAAGAG AAGTGTAAGG CTGCCAGGAA ACAAGCTGTG   1530
 E  E  L  L  T  K  Q  L  L  A  L  D  A  V  D  P  Q  G  E  E  K  C  K  A  A  R  K  Q  A  V
AGGCTTGCGC AGAATATTCT CAGCTATCTC GACCTGAAAT CTGATGAATG GGAGTACTGA AATACCAGAG ATCTCACTTT TGATACTGTT   1620
 R  L  A  Q  N  I  L  S  Y  L  D  L  K  S  D  E  W  E  Y  *
TTGCACTTCA TATGTGCTTC TATGTATAGA GAGCTTTCAG TTCATTGATT TATACGTGCA TATTTCAGTC TTCGGATCAT TATCTGTATG   1710
AAATTCTATT CAGTATCTGC TGCTTTTGAT GTTGCAAGAC AAATATCATT ACAGCACGTT AACTTTTCCA GAGGCAGCTT TGTAGATTT TAAATGGGTT   1800
ATGTGGTGTG GTTTGTTTGG TTTGTCCTTT TTTTTGCGTT TTTAATCAGA AACAAAATA TTACATAATA CTAGGAACT TAGAAAATTT   1890
GTGCAAGCAT TAAAATGCAG GTCTTTCAGA ATCTAGAACT AGGCATAACC TTACATAATA TTATGCTCGA TAGAAGGCTT TTTTTCACT TATGAGAAAG   1980
TGGTTAAATA AGAGTAAGGT TCAAACACAA GCAGTACATG TTCTGTTTCA TTATGCTCGA TTATGCTCGA TAGAAGGCTT TTTTTCACT TATAAGGCCT   2070
```

Fig. 17H

```
GATTGGTCCT ACCCAGCTTA ACGGGGTGGG GTTTTTTTGT TTGTTCAGAC AGTCTGTTCT TTTTTAGTTG GAAAAACAGC  2160
ATCTGCATTT TCCCCATCCT CTACGTTTTA GAGAGGAATC TTGTTTTTGT GTGCAACATA AGAAAATTAT AGCCAAAAAA  2250
CCTTTGAGAT TGCATTAAAG AGAAGGGATA AGGACCAGC AATATACCT TGTAAGTTGC TTTTGTTTGT AAAATCTGAG CTTATAGTTT  2340
TCCTAGTGA GTAATTCAT AAGGATGGGA ACATTTAAAT TAAGTTAATG GGCCTTTAAA AAAAAAAAG GAAACACTCA TACCTGTAGT  2430
TGGAGGATGA ATACTGGAGA CGGGTTACCA ATGTCAGGTT ATACTAAAAC TAAATCAGAA AGTCTGAATG TAGCACATAA TGGTTCTCTT  2520
CTGTGTCCA AGGCTGTAAA ATGGACAGCC TTGTCACACC TCCCCGGTGC TGTTTTACAA CGTGAGGGTA GACGCTGTCA GTAACCCAGA  2610
GGGACCAGGC CTTCCTAGGT TTTCTAGGCA CTCAGCTGTT AACCACTCAC TTAGTAAATG TCATAACTAC ACCTGCTCCA GGACCAATCA  2700
GTGAAACCTG CTCGGAATTA AAGGCTTCCT CTGGGTGCCT GCTGAACAAC TGAGCTCATG TCATGGGCAT GTGGTGGTTT CTCTGTTGCC  2790
TGAAAGAGCC ATTAAAGTCA GTCGTGCGTG AAGCATCTCT CTTCTAAAGG ATGTGTATTT CCATAAATGC TTTCTGAGGA TCCGGTACAA  2880
AATGATTTCC CAAAGTTCTG AAGTGCCTTG AGAACATGTG GGTCCGAGTG TTATAACAGA CTCCTCCCCC GGGTCACCTT TTGCCCTGTC  2970
ATCCTGTTAG AGTACATCTT TGGAAATCCA GGGTAATATT CTCTTTCAGA GATGCTCATT GTGTAACTCT GTGTAGGGAG ATAGTCACTT  3060
TAAACAGCTC AAAGTAGCTA AAGTAGGAG TAGCCTTAAA TACCTAAAAG ATGACAGAAG CATAGCCCTT AACAAATCTT CAGCTTGTCT  3150
CTCAGTATTT CCCAATCATG AAAATCCCTT GCTATGTCTT TCCTACTAGA AATGTTCTAG AATCGCTGGA CGGTGGGGTC AGAGGGCAGT  3240
CGGTATTAG GCCGTGAGCT TCCCATACTA CTGCAGGTCC AACCTCCTGGC AACCGCGGGC TCAAGGCAGG TCATTGGAAT CCACGTTTTG  3330
GCCACAGTAG TTGTAGGATT GCTTTTCTGT ATCATAATTT TAGAATGCTC TTAAATCTT GAGGAAGAGT TTTTATTTT TATTTATTTT  3420
TGAGATGGAG TCTCGTTGC CCAGGCTGCA GTGCAGTGGT GCCATCTCAG GCCATTCAG CCTCACTGCAA CCTCCACCTC CCAGGTTCAA GCGATTCTC  3510
TGCCTCAGCC ACCTGAGTAG CTGGGAGTAC CTGGAGTGTGT ACCTTTTGCC CACCATGTGG GCCCCCCAAA GTGCTGGGAT TGTATTTTTA ATAGAGTTGA GATTTCACCA  3600
TGATGGTCAG GCTGGTCTCG AACTCCTGAC CTCGTGATCC GCCCGCCTCG GCCCGCCTCG TAACGGGTGT GAGCCACGGC  3690
GCCCAGCCCA GCTGCTCCTG TTAAATTAGA GCTCTGTTTA ATTATACCAC TGGGAAATCA CCCTTTAAAA GTGTCCATTG TCTTCCCCAG  3780
AGTACTACTT ACATTTTAAA TTTCATTTTG TAAGTTAAA TGTCAGCATT CCCTTTAAA GTGTCCATTG TTCTTTGAAA GTAGACGTTT  3870
CAGTCATTCT TTTCAAACAA GTGTTTGTGT ACCTTTTGCC ATGGAAATGA TCAGATTGAC CATCGTGTGT GAGTACAGGG TGCTCAGCTC TTCCACCGTC  3960
ATTTGAATT GTTCACATGG GTAATTGGTC ATGGAAATGA TCAGATTGAC CTTGATTGAC TGTCAGGCAT GGCTTTGTT CTAGTTTCAA  4050
TCTGTTCTCG TTCCTTGTAC CGGATTATTC TACTCCTGCA TGAACCCTG TTGACACCGG ATTAGCTCT TGTCGCCCTT CGTGGGGAGC  4140
TGTTTGTGTT AATATGAGCT ACTGCATGTA ATTCTAAAAC TGGCTTGTC ACATTGTATT GTATTTTTGT GATCTGTAAT GAAAAGAATC  4230
TGTACTGCAA GTAAAACCTA CTCCCCAAAA ATGTGTGGGCT TTGGGTCTGC ATTAAACGCT GTAGTCCATG TTCATGCC  4320
```

BAG PROTEINS AND NUCLEIC ACID MOLECULES ENCODING THEM

This application is a divisional of U.S. Ser. No. 10/782,627, filed Feb. 18, 2004, which is a continuation of U.S. Ser. No. 09/394,142, filed Sep. 9, 1999, now U.S. Pat. No. 6,696,558, which claims the benefit of U.S. Provisional Application No. 60/155,212, filed Sep. 9, 1998, which was converted from U.S. Ser. No. 09/150,489, each of which is incorporated herein by reference in its entirety.

STATEMENT AS TO RIGHTS TO INVENTIONS MADE UNDER FEDERALLY-SPONSORED RESEARCH AND DEVELOPMENT

This invention was made with government support under grant number CA-67329 awarded by the National Institutes of Health. The United States Government has certain rights in this invention.

BACKGROUND OF THE INVENTION

1. Field of the Invention

This invention relates generally to the fields of molecular biology and molecular medicine and more specifically to a novel family of proteins that can regulate protein folding. The functions of these proteins are potentially diverse, including promoting tumor cell growth and metastasis.

2. Background Information

The Hsc70/Hsp70-family of molecular chaperones participate in protein folding reactions, controlling protein bioactivity, degradation, complex assembly/disassembly, and translocation across membranes. These proteins interact with hydrophobic regions within target proteins via a carboxyl (C)-terminal peptide binding domain, with substrate binding and release being controlled by the N-terminal ATP-binding domain of Hsc70/Hsp70.

Hsc70/Hsp70-assisted folding reactions are accomplished by repeated cycles of peptide binding, refolding, and release, which are coupled to ATP hydrolysis by the ATP-binding domain (ATPase) of Hsc70/Hsp70 and by subsequent nucleotide exchange. The chaperone activity of mammalian Hsc70/Hsp70 is regulated by partner proteins that either modulate the peptide binding cycle or that target the actions of these chaperones to specific proteins and subcellular compartments. DnaJ-family proteins (Hdj-1/Hsp40; Hdj-2; Hdj-3) stimulate the ATPase activity of Hsc70/Hsp70, resulting in the ADP-bound state which binds tightly to peptide substrates. The Hip protein collaborates with Hsc70/Hsp70 and DnaJ homologues in stimulating ATP hydrolysis, and thus also stabilize Hsc70/Hsp70 complexes with substrate polypeptides, whereas the Hop protein may provide co-chaperone functions through interactions with the C-terminal peptide binding domain.

The Bcl-2 associated athanogene-1 (bag-1) is named from the Greek word athanos, which refers to anti-cell death. BAG-1 was previously referred to as Bcl-2-associated protein-1 (BAP-1) in U.S. Pat. No. 5,539,094 issued Jul. 23, 1996, which is incorporated herein by reference. In this earlier patent, BAG-1 is described as a portion of the human BAG-1 protein, absent the N-terminal amino acids 1 to 85. In addition, a human protein essentially identical to human BAG-1 was described by Zeiner and Gehring, (Proc. Natl. Acad. Sci., USA 92:11465-11469 (1995)). Subsequent to the issuance of U.S. Pat. No. 5,539,094 the N-terminal amino acid sequence from 1 to 85 of human BAG-1 was reported.

BAG-1 and its longer isoforms BAG-1M (Rap46) and BAG-1L are recently described Hsc70/Hsp70-regulating proteins. BAG-1 competes with Hip for binding to the Hsc70/Hsp70 ATPase domain and promotes substrate release. BAG-1 also reportedly stimulates Hsc70-mediated ATP hydrolysis by accelerating ADP/ATP exchange, analogous to the prokaryotic GrpE nucleotide exchange protein of the bacterial Hsc70 homologue, DnaK. Gene transfection studies indicate that BAG-1 proteins can influence a wide variety of cellular phenotypes through their interactions with Hsc70/Hsp70, including increasing resistance to apoptosis, promoting cell proliferation, enhancing tumor cell migration and metastasis, and altering transcriptional activity of steroid hormone receptors.

Despite the notable progress in the art, there remains an unmet need for the further identification and isolation of additional homologous BAG protein species, and the nucleic acid molecules and/or nucleotide sequences that encode them. Such species would provide additional means by which the identity and composition of the BAG domain, that is, the portion of the protein that is influencing or modulating protein folding, could be identified. In addition, such species would be useful for identifying agents that modulate apoptosis as candidates for therapeutic agents, in particular, anticancer agents. The present invention satisfies these need, as well as providing substantial related advantages.

SUMMARY OF THE INVENTION

The present invention provides a family of BAG-1 related proteins from humans [BAG-1L (SEQ ID NO:2), BAG-1 (beginning at residue 116 of SEQ ID NO:2), BAG-2 (SEQ ID NO: 4), BAG-3 (SEQ ID NO:6) and (SEQ ID NO:20), BAG-4 (SEQ ID NO:8) and (SEQ ID NO:22) and BAG-5 (SEQ ID NO:10) and (SEQ ID NO:24)], the invertebrate C. elegans [BAG-1 (SEQ ID NO:12), BAG-2 (SEQ ID NO: 14)] and the fission yeast S. pombe [BAG-1A (SEQ ID NO:16), BAG-1B (SEQ ID NO:18)] and the nucleic acid molecules that encode them.

Another aspect of the present invention provides an amino acid sequence present in the family of BAG-1 related proteins, that modulates Hsc70/Hsp70 chaperone activity, that is, the BAG domain.

Another aspect of the present invention provides novel polypeptide and nucleic acid compositions and methods useful in modulating Hsc70/Hsp70 chaperone activity.

Another aspect of the present invention is directed to methods for detecting agents that modulate the binding of the BAG family of proteins, such as BAG-1 (beginning at residue 116 of SEQ ID NO:2), and related proteins with the Hsc70/Hsp70 Family of proteins or with other proteins that may interact with the BAG-Family proteins.

Still another aspect of the present invention is directed to methods for detecting agents that induce the dissociation of a bound complex formed by the association of BAG-Family proteins with Hsc70/Hsp70 Family molecule chaperones or other proteins.

BRIEF DESCRIPTION OF THE DRAWINGS

Figure 1:
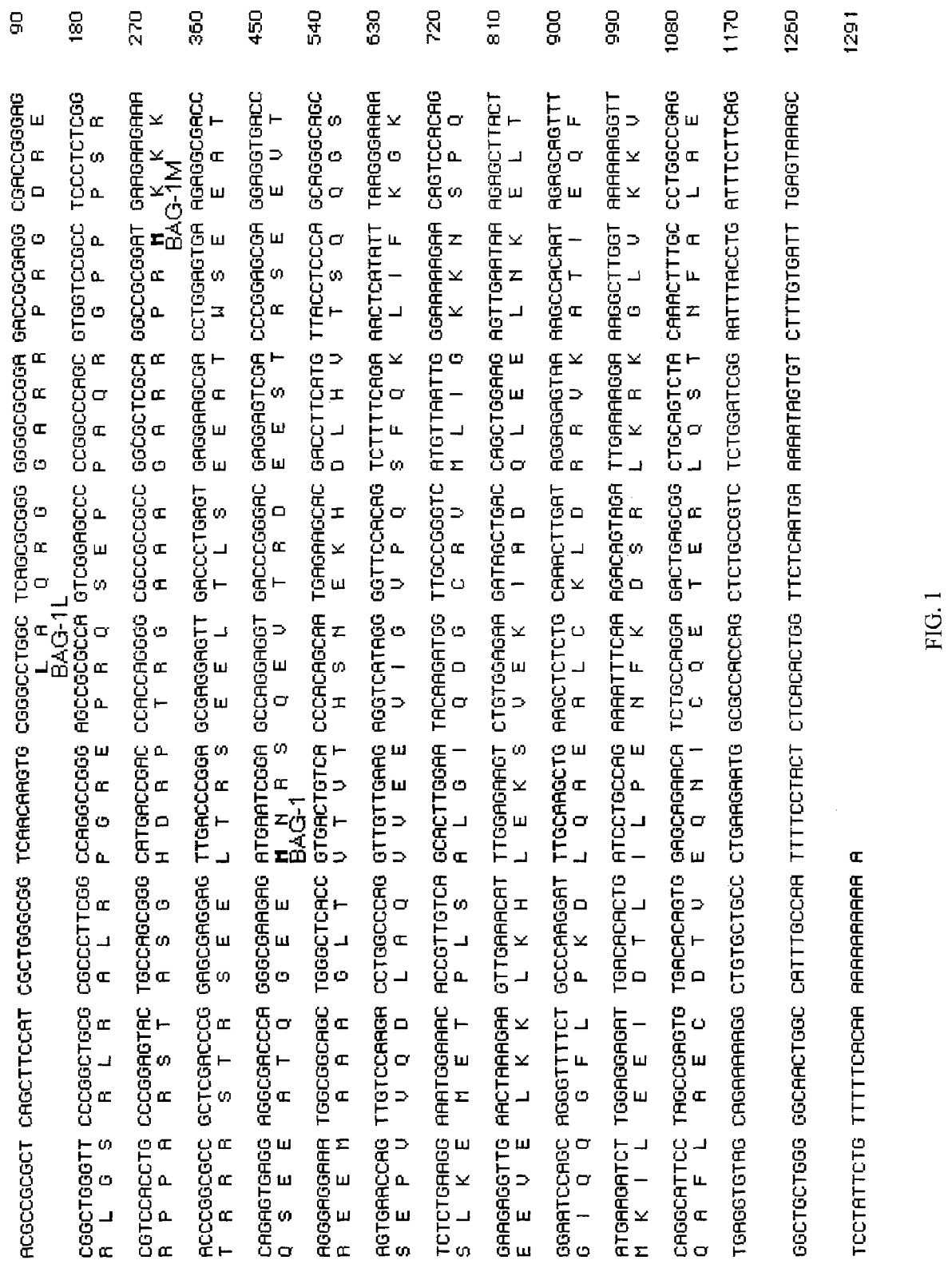

FIG. 1 shows the full length cDNA sequence for human BAG-1 (SEQ ID NO:1) protein with the corresponding amino acid sequence (SEQ ID NO:2). Within the full length sequence are included the overlapping sub-sequences of BAG-1 (beginning at nucleotide 391), BAG-1M [beginning at nucleotide 260 of (SEQ ID NO:2)], and BAG-1L [beginning at nucleotide 46 of (SEQ ID NO:2)].

FIGS. 2A and 2B combined shows the full length cDNA sequence (SEQ ID NO:3) aligned with the corresponding amino acid residues for human BAG-2 protein (SEQ ID NO:4).

FIG. 3 shows a cDNA sequence (SEQ ID NO:5) aligned with the corresponding amino acid residues for human BAG-3 protein (SEQ ID NO:6).

FIG. 4 shows the a cDNA sequence (SEQ ID NO:7) aligned with the corresponding amino acid residues for human BAG-4 protein (SEQ ID NO:8).

FIG. 5 shows a cDNA sequence (SEQ ID NO:9) aligned with the corresponding amino acid residues for human BAG-5 protein (SEQ ID NO: 10).

FIG. 6A shows the full length cDNA sequence for *C. elegans* BAG-1 protein (SEQ ID NO:11).

FIG. 6B shows the 210 amino acid sequence for *C. elegans* BAG-1 protein (SEQ ID NO:12).

FIG. 7A shows the full length cDNA sequence for *C. elegans* BAG-2 protein (SEQ ID NO:13).

FIG. 7B shows the 458 amino acid sequence for *C. elegans* BAG-2 protein (SEQ ID NO:14).

FIG. 8A shows the full length cDNA sequence for *S. pombe* BAG-1A protein (SEQ ID NO:15).

FIG. 8B shows the 195 amino acid sequence for *S. pombe* BAG-1A protein (SEQ ID NO:16).

FIG. 9A shows the full length cDNA sequence for *S. pombe* BAG-1B protein (SEQ ID NO:17).

FIG. 9B shows the 206 amino acid sequence for *S. pombe* BAG-1B protein (SEQ ID NO:18).

FIG. 11 shows assays demonstrating the interaction of BAG-family proteins with Hsc70/ATPase. (A) Two-hybrid assays using yeast expressing the indicated fusion proteins. Blue color indicates a positive interaction, resulting in activation of the lacZ reporter gene. (B) In vitro protein assays using GST-fusion proteins and $^{35}$S-labeled in vitro translated proteins. (C) Co-immunoprecipitation assays using anti-FLAG™ or IgG1 control antibodies and lysates from 293T cells expressing FLAG™-tagged BAG-1 (beginning at residue 116 of SEQ ID NO:2), BAG-2 (SEQ ID NO:4), BAG-3 (SEQ ID NO:6), Daxx, or Apaf-1.

FIGS. 15A and 15B show an expanded cDNA sequence for human BAG-3 protein (SEQ ID NO:19).

FIG. 15C shows the corresponding amino acid residues for the human BAG-3 protein (SEQ ID NO:20) of FIGS. 15A and 15B.

FIGS. 15D and 15E show the expanded cDNA sequence (SEQ ID NO: 19) aligned with the corresponding amino acid residues for human BAG-3 protein of FIGS. 15A and 15B (SEQ ID NO:20).

FIGS. 16A and 16B show an expanded cDNA sequence for human BAG-4 protein (SEQ ID NO:21).

FIG. 16C shows the corresponding amino acid residues for the human BAG-4 protein of FIGS. 16A and 16B (SEQ ID NO:22).

FIGS. 16D and 16E show the expanded cDNA sequence (SEQ ID NO:21) aligned with the corresponding amino acid residues for human BAG-4 protein of FIGS. 16A and 16B (SEQ ID NO:22).

FIGS. 17A, 17B, 17C, and 17D show an expanded cDNA sequence for human BAG-5 protein (SEQ ID NO:23).

FIG. 17E shows the corresponding amino acid residues for the human BAG-5 protein of FIG. 17A-17D (SEQ ID NO:24).

FIGS. 17F, 17G and 17H show the expanded cDNA sequence (SEQ ID NO:23) aligned with the corresponding amino acid residues for human BAG-5 protein of FIG. 17A-17D (SEQ ID NO:24).

DEFINITIONS

Figure 10A:
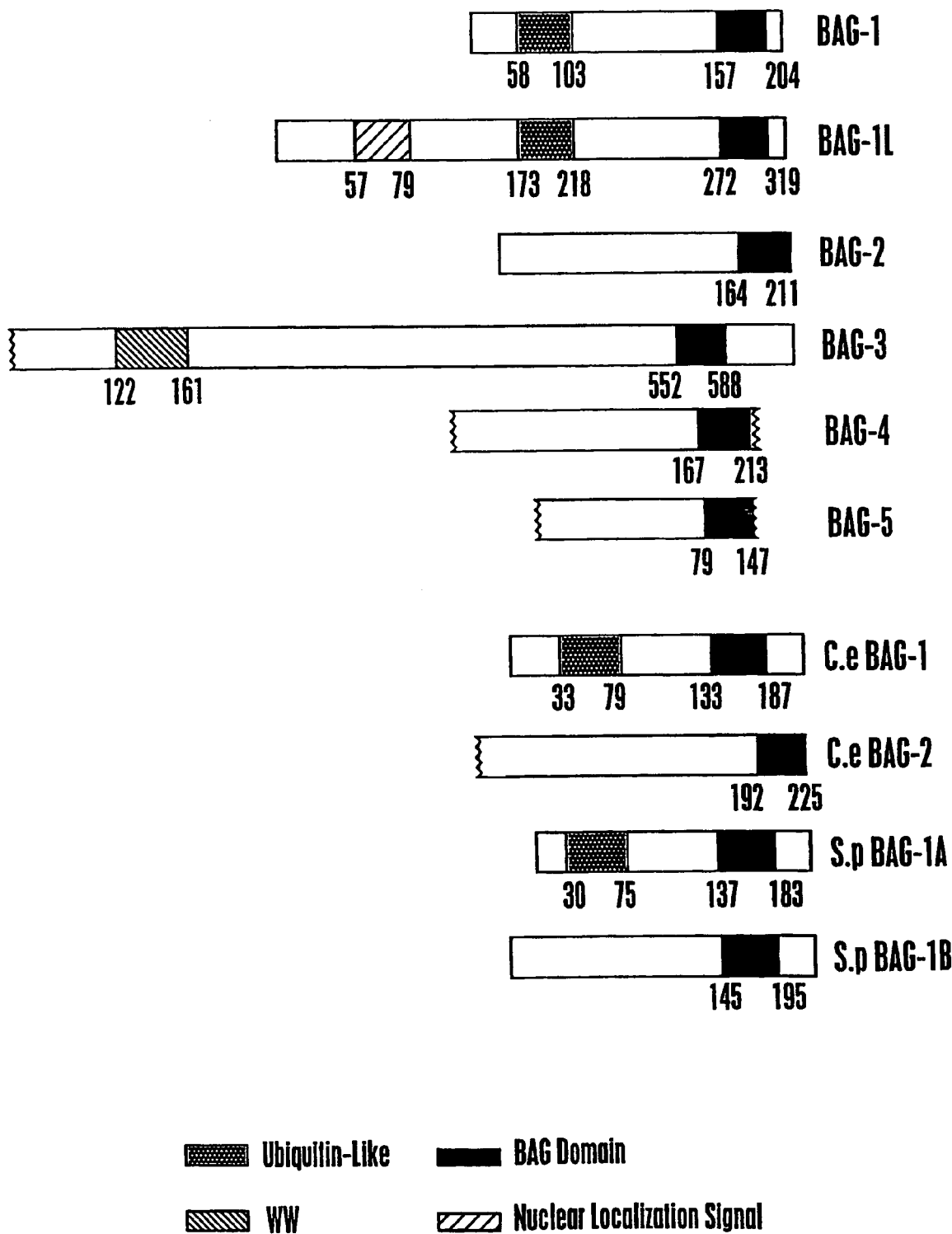
FIG. 10 shows the topologies of the BAG-family proteins; human BAG proteins, BAG-1 (SEQ ID NO:2), BAG-2 (SEQ ID NO:4), BAG-3 (SEQ ID NO:6), BAG-4 (SEQ ID NO:8), BAG-5 (SEQ ID NO:10); *S. pombe* BAG-1A (SEQ ID NO:16) and BAG-1B (SEQ ID NO:18); and *C. elegans* BAG-1 (SEQ ID NO:12) and BAG-2 (SEQ ID NO:14). (A) The relative positions of the BAG domains are shown in black, ubiquitin-like regions are represented in gray, WW domain are represented in strips. Nucleoplasmin-like nuclear localization sequence are also shown. (B) The amino acid sequences of the BAG domain for human BAG-1 (SEQ ID NO:2), BAG-2 (SEQ ID NO:4), BAG-3 (SEQ ID NO:6), BAG-4 (SEQ ID NO:8), BAG-5 (SEQ ID NO:10), *S. pombe* BAG-1A (SEQ ID NO:16) and BAG-1B (SEQ ID NO:18), and *C. elegans* BAG-1 (SEQ ID NO:12) and BAG-2 (SEQ ID NO:14) are aligned demonstrating their homology. Black and gray shading represent identical and similar amino acids, respectively.

The term "apoptosis", as used herein, refers to the process of programmed cell death, although not all programmed cell deaths occur through apoptosis, as used herein, "apoptosis" and "programmed cell death" are used interchangeably.

The term "tumor cell proliferation", as used herein refers to the ability of tumor cells to grow and thus expand a tumor mass.

The term "cell migration", as used herein refers to the role cell motility plays in the invasion and potentially metastasis by tumor cells.

The term "metastasis", as used herein refers to the spread of a disease process from one part of the body to another, as in the appearance of neoplasms in parts of the body remote from the site of the primary tumor; results in dissemination of tumor cells by the lymphatics or blood vessels or by direct extension through serious cavities or subarachnoid or other spaces.

The term "steroid hormone receptor function", as used herein refers to physiological, cellular and molecular functioning of receptors sites that bind with steroid hormones.

The term "substantially purified", as used herein, refers to nucleic acid or amino acid sequence that are removed from their natural environment, isolated or separated, and are at least 60% free, preferably 75% free, and most preferably 90% free from other components with which they are naturally associated.

"Nucleic acid molecule" as used herein refers to an oligonucleotide, nucleotide, or polynucleotide, and fragments or portions thereof, and to DNA or RNA of genomic or synthetic origin which may be single or double stranded, and represent the sense or antisense strand.

"Hybridization", as used herein, refers to any process by which a strand of nucleic acid binds with a complementary strand through base pairing.

The terms "complementary" or "complementarity", as used herein, refer to the natural binding of polynucleotides under permissive salt and temperature conditions by basepairing. For example, the sequence "A-G-T binds to the complementary sequence "T-C-A".

The term "homology", as used herein, refers to a degree of complementarity. There may be partial homology or complete homology (i.e., identity). A partially complementary sequence is one that at least partially inhibits an identical sequence from hybridizing to a target nucleic acid and is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense, and "positive" is sometimes used in reference to the sense strand.

"Amino acid sequence" as used herein refers to an oligopeptide, peptide, polypeptide, or protein sequence, and fragments or portions thereof, and to naturally occurring or synthetic molecules. Where "amino acid sequence" is recited herein this term excludes an amino acid sequence of a naturally occurring protein. "Amino acid sequence", "polypeptide" or "protein" are not meant to limit the amino acid sequence to the complete, native amino acid sequence associated with the recited protein molecule.

The term "functional fragments" or "fragments", as used herein, with regard to a protein refers to portions of that protein that are capable of exhibiting or carrying out the activity exhibited by the protein as a whole. The portions may range in size from three amino acid residues to the entire amino acid sequence minus one amino acid. For example, a protein "comprising at least a functional fragment of the amino acid sequence of SEQ ID NO:1", encompasses the full-length of the protein of SEQ ID NO:1 and portions thereof.

A "derivative" of a BAG protein, as used herein, refers to an amino acid sequence that is altered by one or more amino acids. The derivative may have "conservative" changes, wherein a substituted amino acid has similar structural or chemical properties, e.g., substitution of an apolar amino acid with another apolar amino acid (such as replacement of leucine with isoleucine). The derivative may also have "nonconservative" changes, wherein a substituted amino acid has different but sufficiently similar structural or chemical properties that permits such a substitution without adversely effecting the desired biological activity, e.g., replacement of an amino acid with an uncharged polar R group with an amino acid with an apolar R group (such as replacement of glycine with tryptophan), or alternatively replacement of an amino acid with a charged R group with an amino acid with an uncharged Polar R group (such as replacement of lysine with asparagine).

| Amino Acids - Apolar R Groups | | | |
|---|---|---|---|
| | | Abbreviations | |
| Amino Acid | Radical | 3-Letter | 1-Letter |
| alanine | methyl | ala | A |
| valine | 2-propyl | aal | V |
| leucine | 2-methylpropyl | leu | L |
| isoleucine | 2-butyl | ile | I |
| proline | propyl* - cyclized | pro | P |
| phenylalanine | benzyl | phe | F |
| trytophan | 3-indolylmethl | tyr | W |
| methionine | methylthioethyl | met | M |

| Amino Acids - Uncharged Polar R Groups | | | |
|---|---|---|---|
| | | Abbreviations | |
| Amino Acid | Radical | 3-Letter | 1-Letter |
| glycine | H | gly | G |
| serine | hydroxymethyl | ser | S |
| threonine | 1-hydroxyethyl | thr | T |
| cysteine | thiolmethyl | cys | C |
| tyrosine | 4-hydroxyphenylmethyl | tyr | Y |
| asparagine | aminocarbonylmethyl | asn | N |
| glutamine | aminocarbonylethyl | gln | Q |

| Amino Acids - Charged R Groups | | | |
|---|---|---|---|
| | | Abbreviations | |
| Amino Acid | Radical | 3-Letter | 1-Letter |
| aspartic acid | carboxymethyl | asp | D |
| glutamic acid | carboxyethyl | glu | E |
| lysine | 4-aminobutyl | lys | K |
| arginine | 3-guanylpropyl | arg | R |
| histidine | 4-imidazoylmethyl | his | H |

Similar minor modifications may also include amino acids deletions or insertions or both. Guidance in determining which amino acid residues may be modified as indicated above without abolishing the desired biological functionality may be determined using computer programs well known in the art, for example, DNASTAR software. In addition, the derivative may also result from chemical modifications to the encoded polypeptide, including but not limited to the following, replacement of hydrogen by an alkyl, acyl, or amino group; esterification of a carboxyl group with a suitable alkyl or aryl moiety; alkylation of a hydroxyl group to form an ether derivative. Further a derivative may also result from the substitution of a L-configuration amino acid with its corresponding D-configuration counterpart.

The term "mimetic", as used herein, refers to a molecule, the structure of which is developed from knowledge of the structure of a protein/polypeptide or portions thereof (such as BAG-1) and, as such, is able to effect some or all of the actions of BAG-1 protein.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al., *Anticancer Drug Des.* 8:53-63 (1993)).

DETAILED DESCRIPTION OF THE INVENTION

The present invention provides a family of BAG-1 related proteins from humans [BAG-1L (SEQ ID NO:2), BAG-1S beginning at residue 116 of SEQ ID NO:2, BAG-2 (SEQ ID NO:4), BAG-3 (SEQ ID NO:6) and (SEQ ID NO:20), BAG-4 (SEQ ID NO: 8) and (SEQ ID NO:22) and BAG-5 (SEQ ID NO:10) and (SEQ ID NO:24)], the invertebrate *C. elegans* [BAG-1 (SEQ ID NO:12), BAG-2 (SEQ ID NO: 14)] and the fission yeast *S. pombe* [BAG-1A (SEQ ID NO:16), BAG-1B (SEQ ID NO:18)], specifically the full length amino acid sequences comprising human BAG-1L (SEQ ID NO:2), BAG-1 (beginning at residue 116 of SEQ ID NO:2), and BAG-2 (SEQ ID NO:4) *C. elegans* BAG-1 (SEQ ID NO:12), and BAG-2 (SEQ ID NO:14), and *S. pombe* BAG-1A (SEQ ID NO:16) and BAG-1B (SEQ ID NO:18); and partial sequences comprising human BAG-3 (SEQ ID NO: 6) and (SEQ ID NO:20), BAG-4 (SEQ ID NO:8) and (SEQ ID NO:22), and BAG-5 (SEQ ID NO:10) and (SEQ ID NO:24) and functional fragments thereof. In particular, the invention provides the amino acid sequences comprising human BAG-2 (SEQ ID NO:4), BAG-3 (SEQ ID NO:6) and (SEQ ID NO:20), BAG-4 (SEQ ID NO:8) and (SEQ ID NO:22), and BAG-5 (SEQ ID NO:10) and (SEQ ID NO:24) proteins.

Another aspect of the present invention provides the nucleic molecule and nucleotide sequences that encode the family of BAG-1 related proteins from humans [BAG-1 (SEQ ID NO:1), BAG-2 (SEQ ID NO:3), BAG-3 (SEQ ID NO:5) and (SEQ ID NO:19), BAG-4 (SEQ ID NO:7) and (SEQ ID NO:21) and BAG-5 (SEQ ID NO:9) and (SEQ ID NO:23)], the invertebrate *C. elegans* [BAG-1 (SEQ ID NO:11), BAG-2 (SEQ ID NO:13)] and the fission yeast *S. pombe* [BAG-1A (SEQ ID NO:15), BAG-1B (SEQ ID NO:17)].

BAG-1L (SEQ ID NO:2) is a multifunctional protein that blocks apoptosis, promotes tumor cell metastasis, and contributes to factor-independent and p53-resistant cell growth. BAG-1L (SEQ ID NO:2) interacts with several types of proteins, including Bcl-2, some tyrosine kinase growth factor receptors, steroid hormone receptors, and the p53-induced cell cycle regulator Siah-1A.

BAG-1 is a regulator of Hsc70/Hsp70 family molecular chaperones. A carboxyl-terminal domain in this protein binds tightly to the ATPase domains of Hsc70 and Hsp70 ($K_D=1$ nM) (Zeiner, M., Gebauer, M., and Gehring, U., *EMBO J.* 16: 5483-5490, (1997)). BAG-1 modulates the activity of these molecular chaperones, acting as an apparent functional antagonist of the Hsp70/Hsc70-associated protein Hip (3-5) (Höhfeld, J. and Jentsch, S., *EMBO J.* 16: 6209-6216, (1997); Takayama, S., Bimston, D. N., Matsuzawa, S., Freeman, B. C., Aime-Sempe, C., Xie, Z., Morimoto, R. J., and Reed, J. C., *EMBO J.* 16: 4887-96, (1997); Zeiner, M., Gebauer, M., and Gehring, U., *EMBO J.* 16: 5483-5490, (1997)). In general, protein refolding is accomplished by Hsp70/Hsc70 through repeated cycles of target peptide binding and release, coupled to ATP hydrolysis (Ellis, R., *Curr Biol.* 7: R531-R533, (1997)). BAG-1 appears to promote substrate release, whereas Hip stabilizes Hsp70/Hsc70 complex formation with target peptides (Höhfeld, J., Minami, Y, and Hartl, F.-U., *Cell.* 83:589-598, (1995)). Since each substrate interaction with Hsc70/Hsp70 is unique in terms of the optimal length of time the protein target should remain complexed with Hsc70/Hsp70 for achieving new conformations, the net effect of BAG-1 can be either enhancement or inhibition of the refolding reaction.

The 70 kd heat shock family proteins (Hsp70/Hsc70) are essential to a variety of cellular processes and have been implicated in cancer, yet it is unclear how these proteins are regulated in vivo. A variety of co-chaperones have been identified which may target Hsp70/Hsc70 to different subcellular compartments or promote their interactions with specific protein or protein complexes. BAG-1 appears to represent a novel Hsp70/Hsc70 regulator which differs functionally from all other mammalian co-chaperones identified to date, such as members of the DnaJ-, Hip-, Hop-, and cyclophilin-families of proteins.

Another aspect of the present invention provides the amino acid sequence of a binding domain of about 40 to 55 amino acids that bind the a Hsc70/Hsp70 ATPase domain. The BAG domain is situated near the C-terminus, and the ubiquitin-like domains are situated near the N-terminus.

The BAG family of proteins of the present invention contain a common conserved C-terminal domain (the "BAG" domain) that facilitates binding to the ATPase domain of Hsp70/Hsc70. The carboxyl-terminal domain of BAG-1 binds to the ATPase domain of Hsc70/Hsp70 and regulates its chaperone function by acting as a ADP-ATP exchange factor. Other domains of BAG-1 mediate interactions with proteins such as Bcl-2 and retinoic acid receptors (RARs), allowing BAG-1 to target Hsc70/Hsp70 to other proteins, presumably modulating their function by changing their conformations.

Human BAG-1 was previously shown to inhibit Hsc70/Hsp70 dependent refolding of denatured protein substrates in vitro (S. Takayama, et al., *EMBO J.* 16, 4887-96 (1997); M. Zeiner, M. Gebauer, U. Gehring, *EMBO J.* 16, 5483-5490

(1997); and J. Höhfeld, S. Jentsch, *EMBO J.* 16, 6209-6216 (1997)). In Example III, Part A the effects of recombinant human BAG-1, BAG-2 (SEQ ID NO:4) and BAG-3 (SEQ ID NO:6) were compared using in vitro protein refolding assays similar to those employed previously for assessing BAG-1. The study showed that addition of equimolar amounts of each of the recombinant proteins to Hsc70 resulted in significant inhibition of luciferase refolding, with BAG-2 (SEQ ID NO:4) and BAG-3 (SEQ ID NO:6) showing somewhat greater inhibitor activity than BAG-1 (FIG. 4A). In a separate luciferase folding study BAG-1, BAG-2 (SEQ ID NO:4) and BAG-3 (SEQ ID NO:6) once again displayed inhibition of luciferase refolding, however in this study varying amounts of BAG-1, BAG-2 (SEQ ID NO:4) and BAG-3 (SEQ ID NO:6) were added relative to Hsc70 which resulting in concentration-dependent inhibition of Hsc70 chaperone activity, i.e., luciferase folding (Example III Part A).

Additional follow on studies using the same experimental protocols as the previous studies, as taught in Example IIA, have shown that BAG-4 (SEQ ID NO:22) also undergoes association with Hsc70/ATPase.

Yet another aspect of the present invention provides a nucleotide sequence having at least about 15 nucleotides and, generally, about 25 nucleotides, preferably about 35 nucleotides, more preferably about 45 nucleotides, and most preferably about 55 nucleotides that can hybridize or is complementary under relatively stringent conditions to a portion of the nucleic acid sequences shown in FIGS. 1-9 and FIGS. 15-17, in particular the BAG domain as shown in FIG. 1B, e.g., nucleotides 552-593 of human BAG-3, or nucleotides 167-221 of human BAG-4.

Yet another aspect of the present invention provides a compound of the formula,

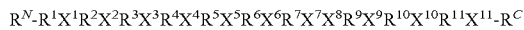

wherein, $R^N$ is a group of 1 to 552 independently selected amino acids;

$R^1$ is a group of 3 independently selected amino acids;

$X^1$ is an amino acid with a charged or uncharged R group, such as aspartic acid, glutamic acid, asparagine, or glutamine;

$R^2$ is a group of 7 independently selected amino acids;

$X^2$ is an amino acid with a charged R group, such as glutamic acid;

$R^3$ is a group of 5 independently selected amino acids;

$X^3$ is an amino acid with an apolar R group, such as leucine, methionine, or isoleucine;

$R^4$ is a group of 3 independently selected amino acids;

$X^4$ is an amino acid with charged R group, such as aspartic acid or glutamine acid;

$R^5$ is a single independently selected amino acid;

$X^5$ is an amino acid with apolar or uncharged R group, such as leucine, valine, methionine, alanine or threonine;

$R^6$ is a group of 15 independently selected amino acids;

$X^6$ is an amino acid with a charged or uncharged R group, such as arginine, lysine, glutamine or aspartic acid;

$R^7$ is a group of 2 independently selected amino acids;

$X^7$ is an amino acid with a charged R group, such as arginine;

$X^8$ is an amino acid with a charged R group, such as arginine or lysine;

$R^9$ is a group of 2 independently selected amino acids;

$X^9$ is an amino acid with an apolar R group, such as valine;

$R^{10}$ is a group of 3 independently selected amino acids;

$X^{10}$ is an amino acid with an uncharged R group, such as glutamine;

$R^{11}$ is a group of 2 independently selected amino acids;

$X^{11}$ is an amino acid with an apolar R group, such as leucine; and $R^C$ is a group of 1 to 100 independently selected amino acids.

A nucleotide sequence of at least about 15 nucleotides and, generally, about 25 nucleotides, preferably about 35 nucleotides, more preferably about 45 nucleotides, and most preferably about 55 nucleotides can be useful, for example, as a primer for the polymerase chain reaction (PCR) or other similar reaction mediated by a polymerase such as a DNA or RNA polymerase (see PCR Protocols: A guide to methods and applications, ed. Innis et al. (Academic Press, Inc., 1990), which is incorporated herein by reference; see, for example, pages 40-41). In addition, such a nucleotide sequence of the invention can be useful as a probe in a hybridization reaction such as Southern or northern blot analysis or in a binding assay such as a gel shift assay.

A nucleotide sequence of the invention can be particularly useful as an antisense molecule, which can be DNA or RNA and can be targeted to all or a portion of the 5'-untranslated region or of the 5'-translated region of a bag-1 nucleic acid sequence in a cell. For example, an antisense molecule can be directed to at least a portion of the sequence shown as the BAG domain in FIG. 1A, e.g., nucleotides 272-319 of human BAG-1L (SEQ ID NO:1), or nucleotides 79-147 of human BAG-5 (SEQ ID NO:9). Since the 5'-region of a nucleic acid contains elements involved in the control of expression of an encoded protein, an antisense molecule directed to the 5'-region of a nucleic acid molecule can affect the levels of protein expressed in a cell.

A nucleotide sequence of the invention also can be useful as a probe to identify a genetic defect due a mutation of a gene encoding a BAG protein in a cell. Such a genetic defect can lead to aberrant expression of a BAG protein in the cell or to expression of an aberrant BAG protein, which does not properly associate with a Bcl-2-related protein or Hsc70/Hsp70 protein in the cell. As a result, a genetic defect in a gene encoding, for example, human BAG-1 can result in a pathology characterized by increased or decreased levels in protein folding.

Further a nucleotide compound or composition as taught in the present invention can be synthesized using routine methods or can be purchased from a commercial source. In addition, a population of such nucleotide sequences can be prepared by restriction endonuclease or mild DNAse digestion of a nucleic acid molecule that contains nucleotides as shown in the nucleotide sequences shown in FIGS. 1-9 and FIGS. 15-17 that encodes the amino acids sequences also shown in FIGS. 1-9 and FIGS. 15-17. Methods for preparing and using such nucleotide sequences, for example, as hybridization probes to screen a library for homologous nucleic acid molecules are well known in the art (see, for example, Sambrook et al., *Molecular Cloning: A laboratory manual* (Cold Spring Harbor Laboratory Press 1989); Ausubel et al., *Current Protocols in Molecular Biology* (Green Publ., NY 1989), each of which is incorporated herein by reference).

A particular nucleotide sequence can be designed based, for example, on a comparison of the nucleic acid molecules encoding any one of the BAG family proteins, as shown in FIGS. 1-9 and FIGS. 15-17, with another in the family. Such a comparison allows, for example, the preparation of a nucleotide sequence that will hybridize to a conserved region present in both nucleic acid molecules, thus providing a means to identify homologous nucleic acid molecules present in other cell types or other organisms. In addition, such a comparison allows the preparation of a nucleotide sequence that will hybridize to a unique region of any of the BAG family nucleotide sequences, such as those corresponding to the BAG domain, thus allowing identification of other proteins sharing this motif. In this regard, it is recognized that, while the human BAG-3 proteins shown as FIGS. 3 and 20, and human BAG-5 proteins shown as FIGS. 5 and 24, are only partial sequences, a variant human BAG-3 or BAG-5 produced, for example, by alternative splicing can exist and can be identified using an appropriately designed nucleotide sequence of the invention as a probe. Such useful probes readily can be identified by inspection of the sequences shown in the disclosed Figures by a comparison of the encoding nucleotide sequences.

If desired, a nucleotide sequence of the invention can incorporate a detectable moiety such as a radiolabel, a fluorochrome, a ferromagnetic substance, a luminescent tag or a detectable binding agent such as biotin. These and other detectable moieties and methods of incorporating such moieties into a nucleotide sequence are well known in the art and are commercially available. A population of labeled nucleotide sequences can be prepared, for example, by nick translation of a nucleic acid molecule of the invention (Sambrook et al., supra, 1989; Ausubel et al., supra, 1989).

One skilled in the art would know that a method involving hybridization of a nucleotide sequence of the invention can require that hybridization be performed under relatively stringent conditions such that nonspecific background hybridization is minimized. Such hybridization conditions can be determined empirically or can be estimated based, for example, on the relative GC content of a sequence and the number of mismatches, if known, between the probe and the target sequence (see, for example, Sambrook et al., supra, 1989).

The invention further provides antibodies specific for human BAG family protein. As used herein, the term "antibody" includes polyclonal and monoclonal antibodies, as well as polypeptide fragments of antibodies that retain a specific binding activity for human BAG-1 of at least about $1 \times 10^5$ M$^{-1}$. One skilled in the art would know that anti-BAG-1 antibody fragments such as Fab, F(ab')$_2$ and Fv fragments can retain specific binding activity for human BAG-1 (beginning at residue 116 of SEQ ID NO:2) and, thus, are included within the definition of an antibody. In addition, the term "antibody" as used herein includes naturally occurring antibodies as well as non-naturally occurring antibodies and fragments that retain binding activity such as chimeric antibodies or humanized antibodies. Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science* 246:1275-1281 (1989), which is incorporated herein by reference.

One skilled in the art would know that purified BAG family protein, which can be prepared from natural sources or synthesized chemically or produced recombinantly, or portions of a BAG family protein, including a portion of human BAG family protein such as a synthetic peptide as described above, can be used as an immunogen. Such peptides useful for raising an antibody include, for example, peptide portions of the N-terminal 85 amino acids or the BAG domain of any of the human BAG proteins (see FIG. 1B). A particularly advantageous use of such a protein is for the immunostaining, wherein the methods provides a process to contrast the immunostaining of BAG-family proteins in carcinoma cells with adjacent non-neoplastic prostatic epithelial and basal cells which are generally present in the same tissue sections. These results would be correlated with a Gleason grade to determine whether any of the BAG-family proteins tend to be expressed at higher or lower levels in histologically advanced tumors. From this process a determination can be made as to degree at which the disease is progressing in a given patient, i.e., a prognosis can be made.

Non-immunogenic fragments or synthetic peptides of BAG proteins can be made immunogenic by coupling the hapten to a carrier molecule such bovine serum albumin (BSA) or keyhole limpet hemocyanin (KLH), as described in Example IV, below. In addition, various other carrier molecules and methods for coupling a hapten to a carrier molecule are well known in the art and described, for example, by Harlow and Lane, *Antibodies: A laboratory manual* (Cold Spring Harbor Laboratory Press, 1988), which is incorporated herein by reference.

EXAMPLES

The following examples are given to enable those skilled in the art to more clearly understand and to practice the present invention. They should not be considered as limiting the scope of the invention, but merely as being illustrative and representative thereof.

Example I

Isolation and Characterization of BAG-family cDNA Sequences

This example describes methods for isolating and characterizing of BAG-family cDNA sequences from human, nematode and yeast.

A. Cloning of Human BAG cDNA Sequences

Yeast two-hybrid library screening of a human Jurkat cell cDNA library was performed as described by Takayama et al., *EMBO J.*, 16:4887-96 (1997); Matsuzawa et al., *EMBO J.*, 17:2736-2747 (1998), which are incorporated herein by reference) using EGY48 strain yeast transformed with pGilda-Hsc70/ATPase (67-377 amino acids) and the lacZ reporter plasmid pSH18-34. Of the resulting ~5×10$^6$ transformants, 112 Leu$^+$ colonies were obtained after 1 week incubation at 30° C. Assay of β-galactosidase (β-gal) activity of these colonies resulted in 96 clones. Mating tests were then performed using RFY206 yeast strain transformed with pGilda, pGilda mBAG-1 (1-219), or pGilda Hsc70/ATPase. Of these, 66 displayed specific interactions with Hsc70/ATPase. The pJG4-5 cDNAs were recovered using KC8 *E. coli* strain which is auxotrophic for tryptophan (Trp). DNA sequencing revealed 3 partially overlapping human BAG-1, 4 identical and one overlapping cDNAs encoding BAG-2, and 2 partially overlapping BAG-3 clones.

Using the above described yeast two-hybrid screen with the ATPase domain of Hsc70 as "bait", several human cDNAs were cloned which encode portions of BAG-1 or of two other BAG-1-like proteins which are termed BAG-2 (SEQ ID NO:4) and BAG-3 (SEQ ID NO:6). The longest of the cDNAs for BAG-2 (SEQ ID NO:3) and BAG-3 (SEQ ID NO:5) contained open reading frames (ORFs) of 207 and 162 amino acids, respectively, followed by stop codons. All BAG-1 (SEQ ID NO:1), BAG-2 (SEQ ID NO:3) and BAG-3 (SEQ ID NO:5) cDNAs obtained by two-hybrid library screening with Hsc70/ATPase contained a conserved domain of about 40-50 amino acids which are termed the "BAG" domain and are shown in FIG. 10. These results demonstrate that a family of BAG-1-related proteins all contain a conserved ~45 amino acid region near their C-terminus that binds Hsc70/Hsp70.

B. Identification of Additional BAG-family Proteins

A search of the translated Genbank database using the bBLAST and FASTA search programs also identified human ESTs that provided sequences for further investigation of BAG-family proteins. The putative BAG-4 (SEQ ID NO:8) and BAG-5 (SEQ ID NO:10) proteins contain BAG-domains that share the greatest sequence similarity with the BAG-domain of BAG-3 (SEQ ID NO:6). These were designated BAG-4 (Accession number AA693697, N74588) and BAG-5 (Accession number AA456862, N34101). BAG-4 has 62% identity and ~81% similarity to BAG-3, and BAG-5 has 51% identity and ~75% similarity to BAG-3.

Additional BAG-family orthologues or homologues were also identified using computer-based searches and resulted in BAG-family homologue in the nematode C. elegans and the fission yeast S. pombe. The C. elegans genome encodes two apparent BAG-family proteins, which are most similar in their overall sequences to the human BAG-1 (Afo39713, gi:2773211) (SEQ ID NO:12) and BAG-2 (SEQ ID NO:14) (Afo68719, gi:3168927). The S. pombe contains two BAG-family proteins that share the greatest overall sequence similarity with human BAG-1 (Alo23S54, gi/3133105 and Alo23634, gi/3150250). The human and C. elegans BAG-1 proteins as well as S. pombe BAG-1A all have ubiquitin-like domains near their N-termini (see FIG. 10A) of unknown function.

The overall predicted amino acid sequences of the C. elegans BAG-1 (SEQ ID NO:12) and S. pombe BAG-1A (SEQ ID NO:16) proteins are ~18% identical (~61% similar) and ~17% identical (~64% similar), respectively, to human BAG-1, implying origin from a common ancestral gene. The C. elegans BAG-1 protein (SEQ ID NO:12), however, contains a 5 to 7 amino acid insert in its BAG-domain as compared to the human, murine, and yeast BAG-1 homologues (see FIG. 10B), and is more similar to BAG-2 (SEQ ID NO:4) in regard to its BAG-domain. C. elegans and human BAG-2 also may be derived from a common ancestor as the C-terminal 225 amino acid region which encompasses both the BAG domain and upstream region of both C. elegans and human BAG-2 share ~34% amino acid sequence identity and ~70% similarity. The human BAG-2 protein (SEQ ID NO:4), however, contains a 9 amino acid insert in its BAG-domain compared to it C. elegans counterpart (see FIG. 10B). Evolutionary-tree prediction algorithms suggest that human and C. elegans BAG-2 represent a distinct branch of the BAG-family that is more evolutionarily distant from the other BAG-family proteins. None of the predicted BAG-family proteins contain recognizable regions analogous to those found in other Hsc70 regulatory proteins, such as the J-domains and G/F-domains of DnaJ family proteins and the Tetratricopeptide Repeat (TR) domains of Hip/Hop family proteins.

C. Yeast Two-hybrid Assay of BAG Binding to Hsc70/ATPase

The longest of the cDNAs obtained for the BAG-2 and BAG-3 proteins were expressed with N-terminal transactivation (TA) domains in yeast and tested by yeast two-hybrid assay for interactions with fusion proteins consisting of Hsp70/ATPase or a variety of unrelated proteins (Fas, Siah, Fadd) containing N-terminal LexA DNA-binding domains. TA-BAG-2 and TA-BAG-3 demonstrated positive interactions with LexA-Hsc70/ATPase, resulting in transactivation of a lacZ reporter gene that was under the control of LexA operators (FIG. 11A). No interactions with LexA-Fas (cytosolic domain), LexA-Siah, LexA-Fadd, or LexA were detected (see FIG. 11A) demonstrating that the BAG-2 and BAG-3 proteins interact specifically with Hsc70/ATPase. Specific two-hybrid interactions between Hsc70/ATPase and either BAG-2 or BAG-3 were also observed when BAG-2 and BAG-3 were expressed as LexA DNA-binding domain fusion proteins and Hsc70/ATPase was fused with a TA domain (see FIG. 11A; right panel). These results demonstrate that similarly to BAG-1, BAG-2 and BAG-3 specifically interact with Hsc70/ATPase.

In order to determine whether the BAG proteins are capable of forming heterodimers, coexpression of BAG-2 and BAG-3 in the yeast two-hybrid assay was also performed. Coexpression of BAG-2 and BAG-3 failed to show interaction with BAG-1 or a deletion mutant of BAG-1 (ΔC) which is missing part of its C-terminal domain required for Hsp70/Hsc70 binding suggest that these proteins do not form heterodimers.

D. Isolation and Characterization of the Complete Open Reading Frame Sequences of BAG-2 and BAG-3

In order to deduce the complete ORFs of BAG-2 and BAG-3, a λ-phage cDNA library was screened as follows, using hybridization probes derived from the two-hybrid screening. A human jurkat T-cell λ-ZapII library cDNA library (Stratagene) was screened by hybridization using $^{32}$P-labeled purified insert DNA from the longest of the human BAG-2 (clone #11) and human BAG-3 (clone #28) cDNA clones. From about one million clones screened, 38 BAG-2 and 23 BAG-3 clones were identified, cloned, and their cDNA inserts recovered as pSKII plasmids using a helper phage method (Stratagene). DNA sequencing of λ-phage derived human BAG-2 cDNA clones revealed an ORF encoding a predicted 211 amino acid protein, preceded by an in-frame stop codon. The longest human BAG-3 λ-phage cDNA clone contains a continuous ORF of 682 amino acids followed by a stop codon, but without an identifiable start codon (see FIG. 10A).

Although BAG-1L (SEQ ID NO:2), BAG-1 (beginning at residue 116 of SEQ ID NO:2), BAG-2 (SEQ ID NO:4), and BAG-3 (SEQ ID NO:6) all contain a homologous BAG domain near their C-terminus, the N-terminal regions of these proteins are dissimilar. Using a combination of search tools (Prosite Search: PP search, using the Prosite pattern database, BCM Search Launcher, Baylor College of Medicine, and Blocks Search), it was determined that the BAG-2 N-terminal region contains potential kinase phosphorylation sites but otherwise shares no apparent similarity with other proteins or known functional domains.

Figure 10B:
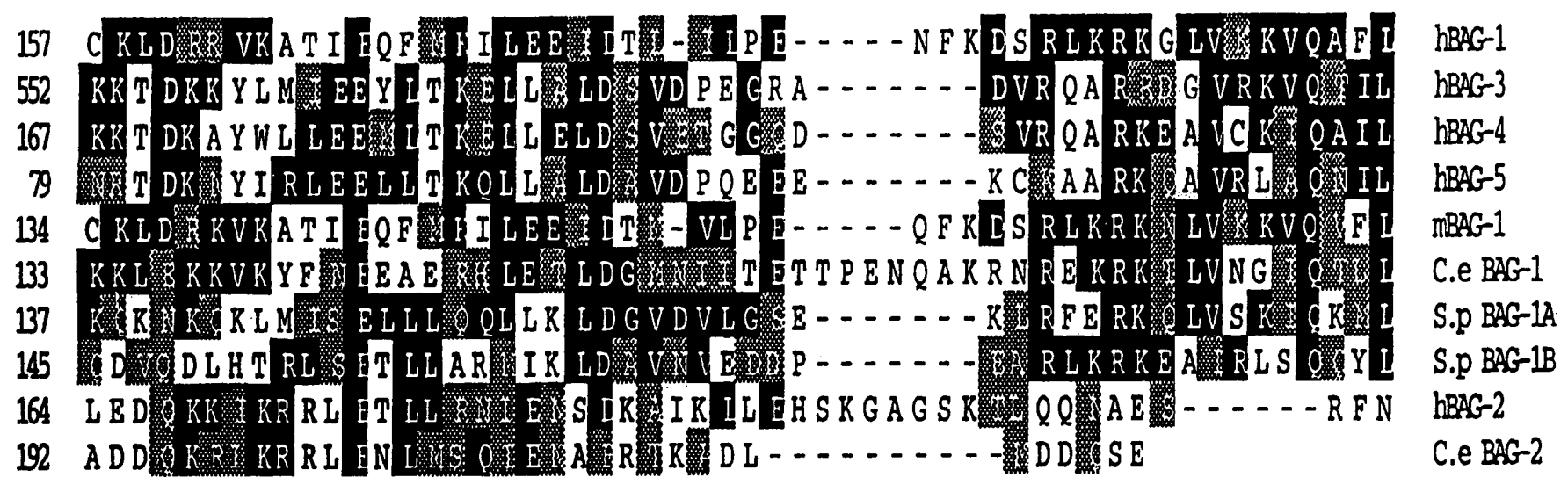

In contrast, the predicted N-terminal region BAG-3 contains a WW domain as shown in FIG. 10A. WW domains have been identified in a wide variety of signaling proteins, including a Yes kinase adaptor protein (YAP), the Na$^+$-channel regulator Nedd4, formin-binding proteins, dystrophin, and the peptidyl prolyl cis-trans-isomerase Pin-1. These roughly 40 amino acid domains mediate protein interactions and bind the preferred peptide ligand sequence xPPxY (Sudol., *TIBS*, 21: 161-163, 1996, which is incorporated herein by reference).

Example II

In Vitro Association of BAG Proteins and Hsc70/ATPase

This example demonstrates that BAG-2 (SEQ ID NO:4) and BAG-3 (SEQ ID NO:6) bind Hsc70/ATPase in various in vitro assays.

A. Solution Binding Assay of BAG-2 and BAG-3 to Hsc70/ATPase

Association of BAG-2 (SEQ ID NO:4) and BAG-3 (SEQ ID NO:6) with Hsc70/ATPase was determine by an in vitro protein binding assay where Hsc70/ATPase or BAG-family proteins were expressed in bacteria as Glutathione S-Transferase (GST) fusion proteins. Purified cDNA sequences encoding residues 5 to 211 of human BAG-2 (clone #11) and the C-terminal 135 amino acids of human BAG-3 (clone #28) (see FIG. 10A) were subcloned into the EcoRI/Xho I sites of pGEX4T-1 prokaryotic expression plasmid (Pharmacia; Piscataway, N.J.). These plasmids as well as pGEX4T-1-BAG-1, pGEX-4T-1-BAG-1 (ΔC), and pGEX-4T-1-XL which have been described previously (Takayama et al., supra (1997); Xie et al., *Biochemistry,* 37:6410-6418, (1998), which are incorporated herein by reference), were expressed in XL-1 blue strain *E. Coli* (Stratagene, Inc., La Jolla, Calif.). Briefly, a single colony was inoculated into 1 L of LB media containing 50 µg/ml ampicillin and grown at 37° C. overnight. The culture was then diluted by half with fresh LB/ampicillin and cooled to room temperature for 1 hr, before inducing with 0.4 mM IPTG for 6 h at 25° C.

Cells were recovered and incubated with 0.5 mg/ml lysozyme in 50 mM Tris (pH 8.0), 150 mM NaCl, 1% TWEEN™-20, 0.1% 2-mercaptoethanol, 5 mM EDTA, 1 mM PMSF and a mixture of other protease inhibitors obtained from Boehringer Mannheim (1697498) at room temperature for 0.5 h, followed by sonication. Cellular debris were pelleted by centrifugation at 27,500 g for 10 min and the resulting supernatants were incubated with 30 ml of glutathione-SEPHAROSE™ (Pharmacia) at 4° C. overnight. The resin was then washed with 20 mM Tris (pH 8.0), 150 mM NaCl, 0.1% TWEEN™-20, and 0.1% 2-Mercaptoethanol until the OD 280 nm reached <0.01. For removal of GST, the resin with immobilized GST-fusion protein was incubated with 10U of thrombin (Boehringer, Inc.) at 4° C. in 20 mM Tris (pH 8.0), 150 mM NaCl, 0.1% TWEEN™-20, 0.1% 2-Mercaptoethanol, and 2.5 mM $CaCl_2$ overnight. Released proteins were then purified on MONO Q™ (HR10/10, Pharmacia) by FPLC using a linear gradient of 0.5M NaCl at pH 8.0 and dialyzed into chaperone assay buffer.

The ability of BAG-2 (SEQ ID NO:4) or BAG-3 (SEQ ID NO:6) to bind Hsc70/ATPase in solution was then examined. GST control or GST-BAG proteins were immobilized on glutathione-SEPHAROSE™ and tested for binding to $^{35}S$-labeled in vitro translated (IVT) proteins. Immunoprecipitation and in vitro GST-protein binding assays were performed as described by Takayama et al., supra (1997), using pCI-Neo FLAG™ or pcDNA3-HA into which human Bag-2 (clone #11) or human BAG-3 (clone #28) had been subcloned for in vitro translation of $^{35}S$-L-methionine labeled proteins or expression in 293T cells. As shown in FIG. 11B, $^{35}S$-Hsc70/ATPase bound in vitro to GST-BAG-1, GST-BAG-2, and GST-BAG-3 but not to GST-BAG-1 (.DELTA.C) or several other control proteins. BAG-1 (beginning at residue 116 of SEQ ID NO:2), BAG-2 (SEQ ID NO:4), and BAG-3 (SEQ ID NO:6) also exhibited little or no binding to themselves or to each other, demonstrating that these proteins do not strongly homo- or hetero-dimerize or oligomerize. It should be noted, however, that BAG-2 (SEQ ID NO:4) displayed weak interactions with itself in binding assays and produced a positive result in yeast two-hybrid experiments, demonstrating that it can have the ability to self-associate.

B. Binding of BAG Proteins to Hsc70 In Vivo

The ability of BAG-2 (SEQ ID NO:4) and BAG-3 (SEQ ID NO:6) proteins to interact in cells with Hsc70 was tested by expressing these proteins with N-terminal FLAG™ epitope tags in 293T human epithelial cells using co-immunoprecipitation assays as described previously (Takayama et al., supra (1997)). cDNAs encoding the λ-phage cloned regions of BAG-2 and BAG-3 were subcloned in-frame into pcDNA3FLAG™. Anti-FLAG™ immune complexes prepared from 293T cells after transfection with plasmids encoding FLAG™-BAG-1, FLAG™-BAG-2, or FLAG™-BAG-3 were analyzed by SDS-PAGE/immunoblot assay. As shown in FIG. 10C, antiserum specific to Hsc70 detected the presence of BAG proteins associated with Hsc70, whereas control immune-complexes prepared with IgG 1 as well as anti-FLAG™ immune complexes prepared from cells transfected with FLAG™-tagged control proteins, Daxx and Apaf-1, did not contain Hsc70 associated protein. These results further demonstrate that BAG-family proteins specifically bind to Hsc70. C. BIACORE™ Assay of BAG Protein Binding to the ATPase Domain of Hsc70

BAG-1 (beginning at residue 116 of SEQ ID NO:2) is known to bind tightly to the ATPase domain of Hsc70 (Stuart et al., *J. Biol. Chem.*, In Press (1998)). BAG-2 (SEQ ID NO:4) and BAG-3 (SEQ ID NO:6) proteins were therefore, examined for their ability to bind to Hsc70/ATPase. The affinity and binding kinetics of BAG-2 (SEQ ID NO:4) and BAG-3 (SEQ ID NO:6) to Hsc70 /ATPase was also compared to that of BAG-1 (beginning at residue 116 of SEQ ID NO:2) for Hsc70 /ATPase, using a surface plasmon resonance technique (BIACORE™) which has been described previously (Stuart et al., supra, (1998) which is incorporated herein by reference).

Figure 12:
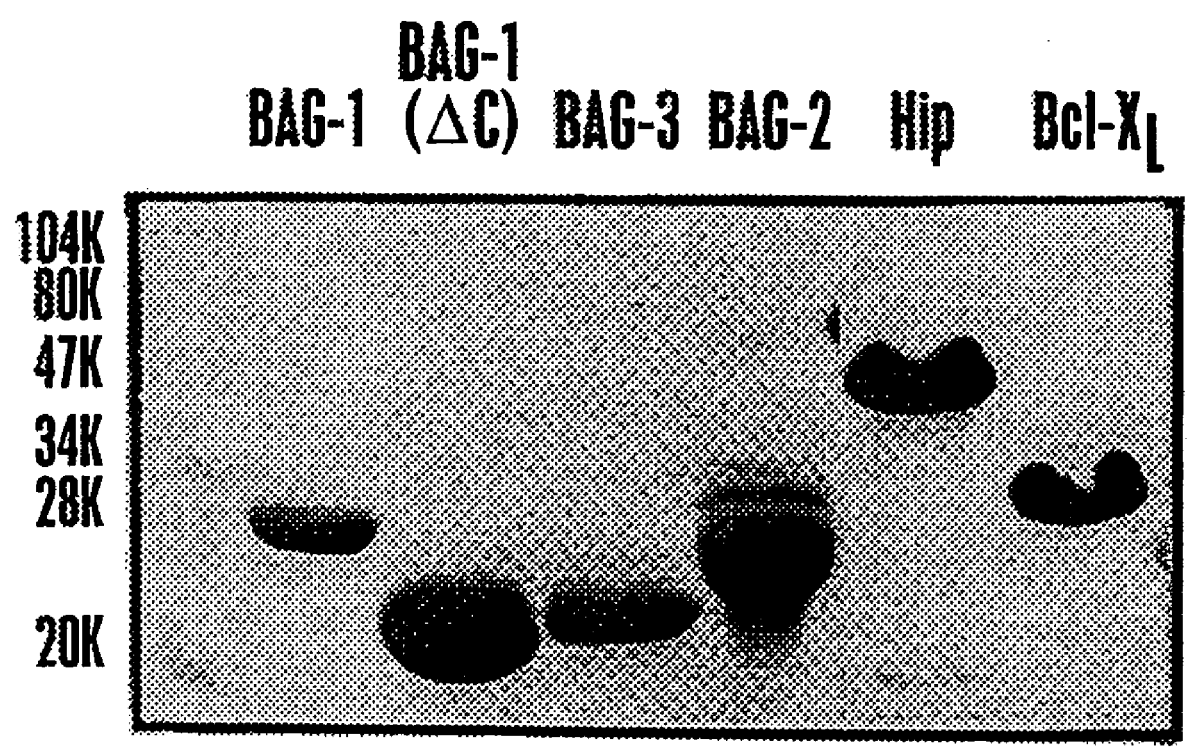
FIG. 12 shows surface plasmon resonance analysis of BAG-family protein interactions with Hsc70/ATPase. (A) SDS-PAGE analysis of purified recombinant proteins. (B) Representative SPR results of biosensor chips containing immobilized BAG proteins with and without maximally bound Hsc70/ATPase.
Figure 13A:
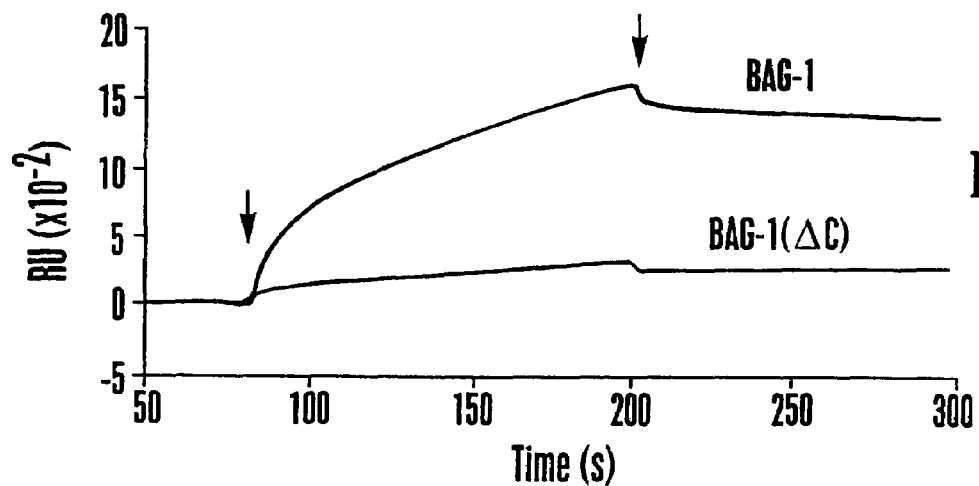
FIG. 13 shows representative SPR results for biosensor chips containing immobilized BAG-1 (beginning at residue 116 at SEQ ID NO:2), BAG-1 (ΔC), BAG-2 (SEQ ID NO:4), or BAG-3 (SEQ ID NO:6) proteins. Hsc70/ATPase was flowed over the chips (arrow/left) until maximal binding was reached (response units), then flow was continued without Hsc70/ATPase (arrow/right). For BAG-2 (SEQ ID NO:4) and BAG-3 (SEQ ID NO:6), Hsc70 was injected at 0.0175, 0.035, 0.07, 0.14, and 0.28 μM.
Figure 13B:
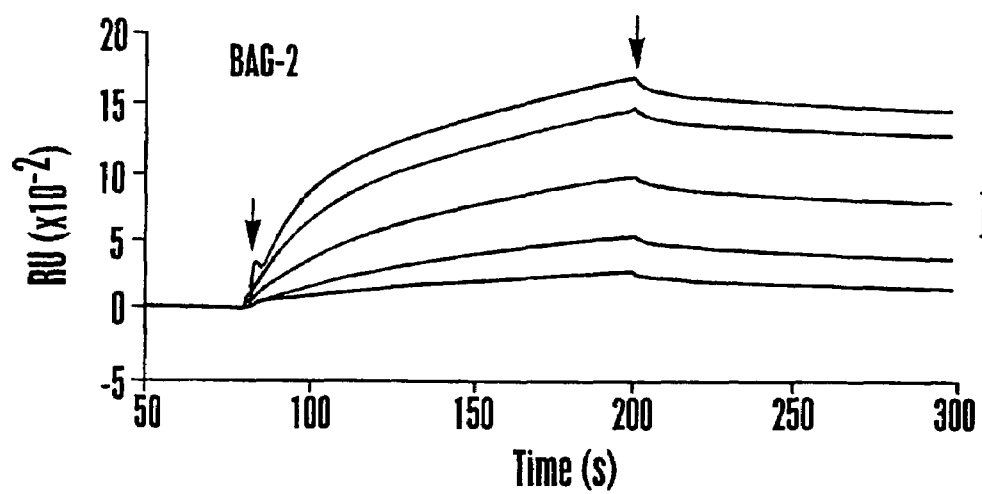
Figure 13C:
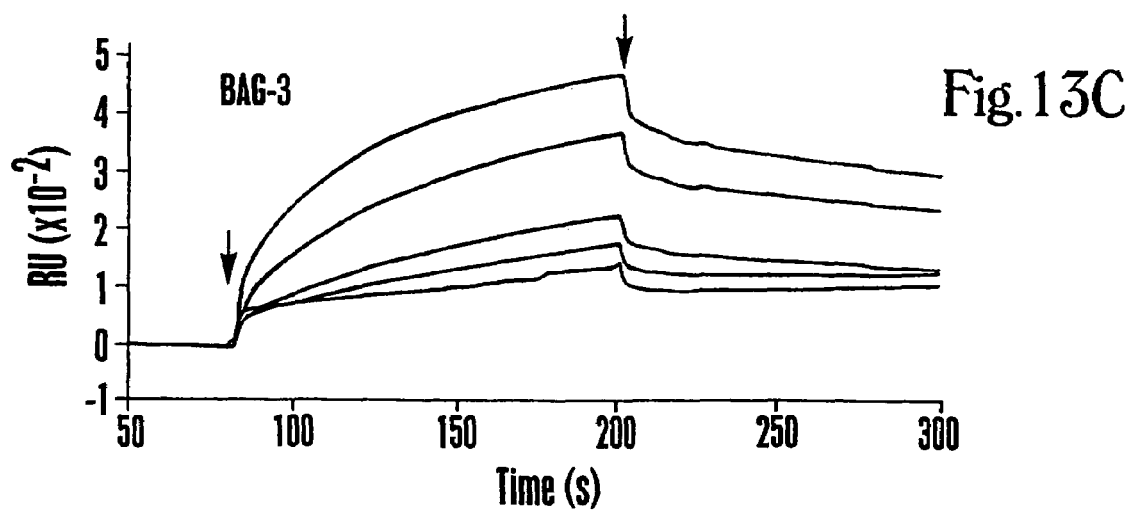
Figure 14A:
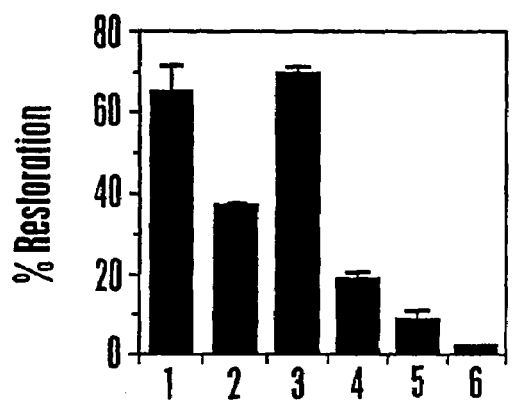
FIG. 14 shows BAG-family protein modulation of Hsc70 chaperone activity. (A) Protein refolding assay of chemically-denatured luciferase by Hsc70 plus DnaJ in the absence or presence of BAG and BAG-mutant proteins. (B) Concentration-dependent inhibition of Hsc70-mediated protein refolding by BAG-family proteins [BAG-1 (beginning at residue 116 of SEQ ID NO:2), BAG-2 (SEQ ID NO:4), BAG-3 (SEQ ID NO:6)] but not by BAG-mutant (BAG-1 (ΔC). (C) Hsc70/Hsp40-mediated refolding of heat-denatured luciferase was assayed in the presence of (black bars) or absence of (striped bars) of 1.8 μM Hip, with (lanes 3-10) or without (lanes 1,2) various BAG-family proteins (1.8 μM) as indicated (mean±SE; n=3). A control (CNTL) is shown (lane 1) in which Hsc70 was replaced with an equivalent amount of BSA.
Figure 14B:
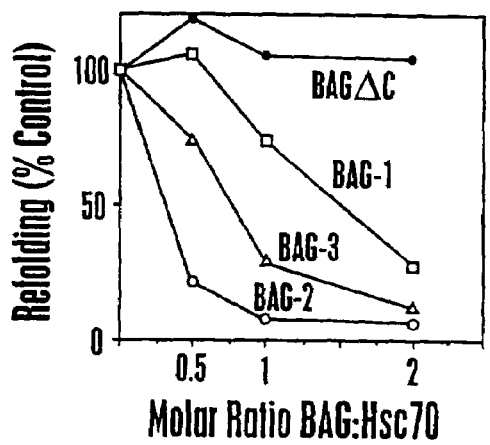
Figure 14C:
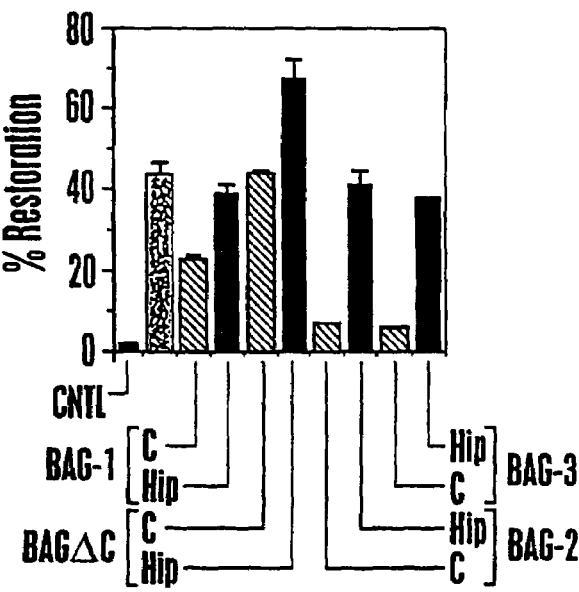
Figure 18:
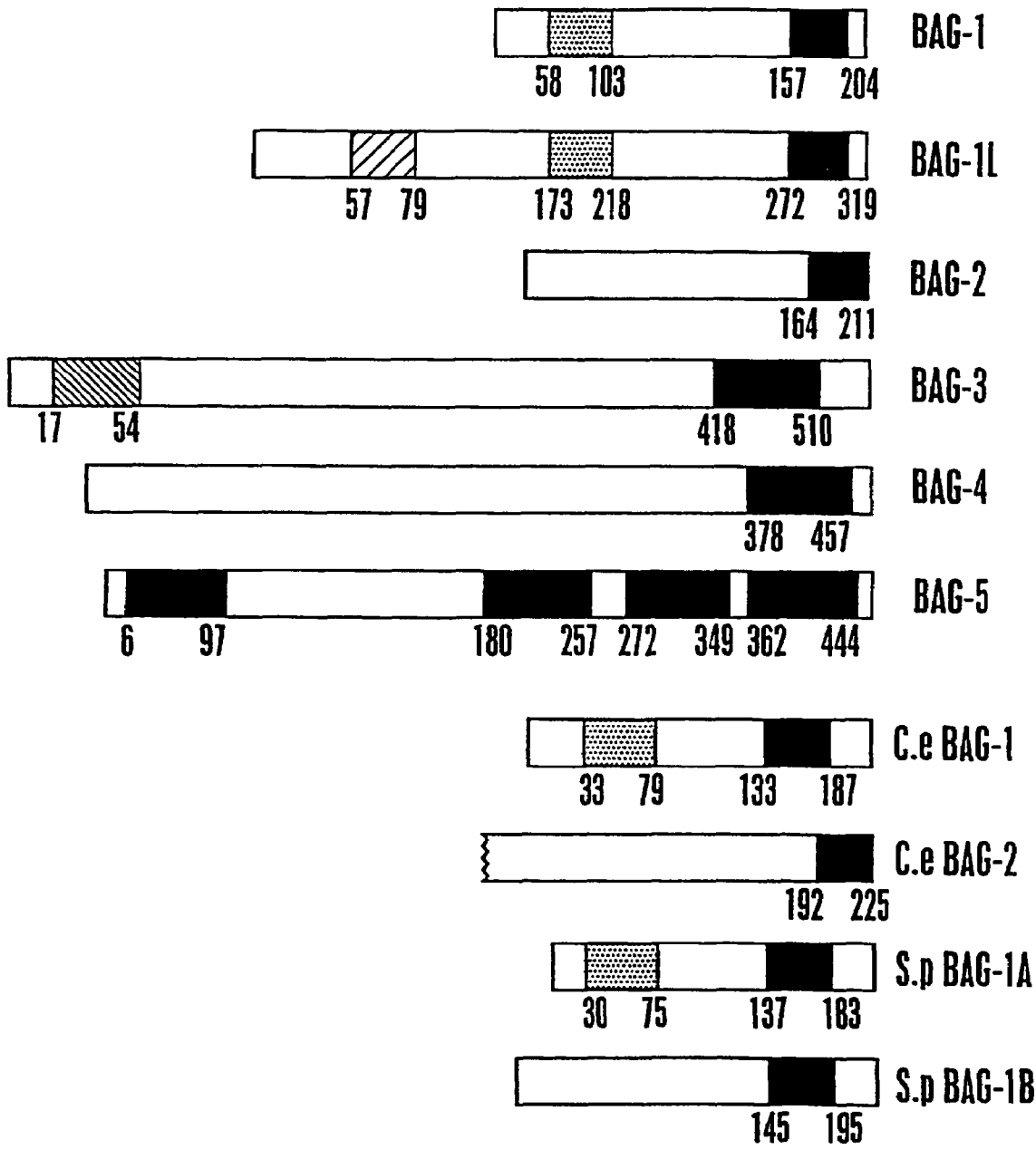
FIG. 18 shows the topologies of the BAG-family proteins; human BAG proteins, BAG-1 (SEQ ID NO:2), BAG-2 (SEQ ID NO:4), expanded BAG-3 (SEQ ID NO:20), expanded BAG-4 (SEQ ID NO:22), expanded BAG-5 (SEQ ID NO:24); *S. pombe* BAG-1A (SEQ ID NO:16) and BAG-1B (SEQ ID NO:18); and *C. elegans* BAG-1 (SEQ ID NO:12) and BAG-2 (SEQ ID NO: 14). The relative positions of the BAG domains are shown in black, ubiquitin-like regions are represented in gray, WW domain are represented in strips. Nucleoplasmin-like nuclear localization sequence are also shown.

BAG-family proteins were produced in bacteria and purified to near homogeneity as shown in FIG. 12A and described above in Example I. The purified BAG-1 (beginning at residue 116 of SEQ ID NO:2), -2 (SEQ ID NO:4), and -3 (SEQ ID NO:6) proteins were then immobilized on biosensor chips and tested for their interactions with Hsc70 in the soluble phase. Kinetic measurements were performed using a BIACORE™-II instrument with CM5 sensor chip and Amine Coupling Kit (Pharmacia Biosensor AB, Sweden). Briefly, for immobilization of proteins, the sensor chip was equilibrated with HK buffer (10 mM Hepes (pH 7.4), 150 mM KCL) at 5 µl/min, then activated by injecting 17 µl of 0.2M N-ethyl-N'-(3-diethylaminopropyl)-carbodiimide and 0.05M N-hydroxysuccinimide (NHS/EDC) followed by 35 µl of the protein of interest, in 10mM acetate, pH 3.5-4.5. Excess NHS-ester on the surface was deactivated with 17 µl 1M ethanolamine-HCL (pH8.5). After immobilization, 5 µl of regeneration buffer (50 mM phosphate (pH 6.8) and 4M GuHCl) was injected. For binding assays, Hsp70 (Sigma, H8778) was dissolved in HK buffer, and injected at 10 µl/ml across the prepared surface at various concentrations. The surface was regenerated after each injection with 5 µl of regeneration buffer. The rate constants $\kappa_{ass}$ and $\kappa_{diss}$ were generated with BIAevaluation software 3.01 (Pharmacia Biosensor AB). Addition of Hsc70 to chips containing BAG-1 (beginning at residue 116 of SEQ ID NO:2), BAG-2 (SEQ ID NO:4) or BAG-3 (SEQ ID NO:6) resulted in concentration-dependent binding, as reflected by an increase in the Response Units (RU) measured at the chip surface (shown in FIG. 3B). In contrast, Hsc70 failed to display interactions in BIACORE™ assays with a variety of control proteins as well as a mutant of BAG-1 lacking a C-terminal portion of the BAG domain which is required for Hsc70-binding (FIG. 3B). Furthermore, flowing of various control proteins such as GST, BSA and Bcl-XL over the BAG-1 (beginning at residue 116 of SEQ ID NO:2), BAG-2 (SEQ ID NO:4), or BAG-3 (SEQ ID NO:6) chips resulted in negligible interaction. These results further demonstrate the specificity with which BAG-family proteins interact with and bind to Hsc70.

The rates of Hsc70 binding to BAG-1 (beginning at residue 116 of SEQ ID NO:2), BAG-2 (SEQ ID NO:4), and BAG-3

(SEQ ID NO:6) proteins were similar, following pseudo first-order kinetics with estimated association rate constants ($\kappa_a$) of 2.1, 2.1 and $2.4 \times 10^5$ M$^{-1}$ sec$^{-1}$, respectively. After allowing binding of Hsc70 to immobilized BAG-1 (beginning at residue 116 of SEQ ID NO:2), BAG-2 (SEQ ID NO:4), or BAG-3 (SEQ ID NO:6) to reach plateau levels, the chaperone was removed from the flow solution and the dissociation rate was monitored. BAG-1 (beginning at residue 116 at SEQ ID NO:2) and BAG-2 (SEQ ID NO:4) exhibited similar dissociation rates, with relatively slow loss of Hsc70 from the chip surface, resulting in estimated dissociation rate constants ($\kappa_d$) of 3.0 and $5.0 \times 10^{-4}$ sec$^{-1}$, respectively (see FIG. 3B). In contrast, Hsc70 dissociated more rapidly from biosensor chips containing BAG-3 (see FIG. 3B), yielding an estimated $\kappa_d$ of $1.7 \times 10^{-3}$ sec$^{-1}$. From the kinetic data, the apparent affinities ($\kappa_D = \kappa_d / \kappa_a$) were calculated for binding of Hsc70 to BAG-1 (beginning at residue 116 of SEQ ID NO:2), BAG-2 (SEQ ID NO:4), and BAG-3 (SEQ ID NO:6) and were estimated to equal about $K_D = 1.4$ nM, $K_D = 2.4$ nM, and $K_D = 7.4$ nM, respectively. These results demonstrate that the interactions of BAG-family proteins with Hsc70 occur with apparent affinities sufficient for physiological relevance.

Example III

BAG-family Proteins Inhibit
Hsp70/Hsc70-dependent Protein Folding

This example demonstrates that BAG-2 (SEQ ID NO:4) and BAG-3 (SEQ ID NO:6) proteins inhibit Hsp70/Hsc70-dependent refolding of denatured proteins similarly to a BAG-1 (beginning at residue 116 of SEQ ID NO:2) protein.

The effects of BAG-2 (SEQ ID NO:4) and BAG-3 (SEQ ID NO:6) protein on Hsp70/Hsc70-dependent protein refolding was determined using in vitro protein refolding assays similar to those described previously by Takayama et al., supra, 1998; Terada et al., J. Cell Biol., 139:1089-1095, 1997, which are incorporated herein by reference. Briefly, luciferase (20 µM) was denatured in 25 mM Hepes-KOH, pH 7.2, 50 mM potassium acetate, 5 mM DTT, 6M guanidine hydrochloride at ~25° C. for 1 h. Denatured luciferase was diluted 1:40 into 25 mM Hepes-KOH, pH 7.2, 50 mM potassium acetate, 5 mM DTT. Hsc70 (1.8 µM), DnaJ (StressGen, Inc.) (0.9 µM), and various purified recombinant proteins as indicated were added to refolding buffer (30 mM Hepes-KOH, pH 7.6, 120 mM potassium acetate, 3 mM magnesium acetate, 2 mM DTT, 2.5 mM ATP) with 0.2 volume of diluted denatured luciferase to a final concentration of 0.1 µM. Luciferase activity was measured after 1.5 hr incubation at 35° C.

The combination of Hsc70 and DnaJ resulted in ATP-dependent refolding of chemically denatured firefly luciferase, with function of over half the denatured enzyme restored in a 90 minute reaction, as monitored by a chemiluminescence assay. In contrast, neither Hsc70 nor DnaJ alone were able to induce substantial refolding of denatured luciferase. Furthermore, little spontaneous restoration of luciferase activity was observed with control proteins, BSA, GST or Bcl-XL (see FIG. 4A).

Addition of recombinant purified BAG-1 (beginning at residue 116 of SEQ ID NO:2), BAG-2 (SEQ ID NO:4), or BAG-3 (SEQ ID NO:6) to the above assays in amounts equimolar to Hsc70 (1.8 µM) resulted in striking inhibition of luciferase refolding. BAG-2 (SEQ ID NO:4) and BAG-3 (SEQ ID NO:6) displayed somewhat greater inhibitory activity than BAG-1 (beginning at residue 116 of SEQ ID NO:2) as shown in FIG. 4A. In contrast, the BAG-1 (ΔC) protein, which fails to bind Hsc70 as well as several other control proteins, had no effect on luciferase refolding.

In an additional refolding assay, described previously by Minami et al., J. Biol. Chem. 271:19617-24, 1996), purified Hsc70 and human DnaJ homolog Hdj-1 (Hsp 40) were used with additional cofactors provided in reticulocyte lysates (5% v:v) to produce a system capable of refolding denatured luciferase. Briefly, additional cofactors included, recombinant Luciferase (Promega: QuantiLum™), that had been heat denatured at 42° C. for 10 min, 1.8 µM Hsc70 (Sigma; purified from bovine brain), 0.9 µM Hsp40, and various recombinant purified proteins. Luciferase activity was measured (Promega luciferase assay kit) using a luminometer (EG&G Berthold, MicroLumat luminometer, Model #LB96P). All results were normalized relative to non-denatured luciferase that had been subjected to the same conditions. Control reactions lacking ATP, Hsc70, or Hsp40 resulted in negligible luciferase refolding.

Various amounts of purified BAG-1 (beginning at residue 116 of SEQ ID NO:2), BAG-2 (SEQ ID NO:4), or BAG-3 (SEQ ID NO:6), relative to amounts of Hsc70 were used in the above-described protein refolding assay. Addition of BAG-family proteins resulted in a concentration-dependent inhibition of Hsc70 chaperone activity. Furthermore, the BAG-2 (SEQ ID NO:4) and BAG-3 (SEQ ID NO:6) inhibition of Hsc70 chaperone activity was demonstrated to be as potent as that observed for BAG-1 (beginning at residue 116 of SEQ ID NO:2). In contrast, the BAG-1 (ΔC) mutant as well as other control proteins did not suppress Hsc70-mediated refolding of denatured luciferase. These results indicate that BAG-2 (SEQ ID NO:4) and BAG-3 (SEQ ID NO:6) can inhibit Hsc70/Hsp70 dependent protein refolding activity to the same extent as BAG-1 (beginning at residue 116 of SEQ ID NO:2).

B. BAG Competes with Hip for Binding to Hsc70.

It is known that BAG-1 competes with Hip for binding to Hsc70, with these proteins exerting opposite effects on Hsc70-mediated protein refolding (Hohfeld, J., and Jentsch, S., Embo J., 16:6209-6216, 1997, which is incorporated herein by reference). In order to determine whether BAG-2 (SEQ ID NO:4) and BAG-3 (SEQ ID NO:6) also compete with Hip for binding to Hsc70, refolding assays were performed as described above in the presence of Hip protein.

Hip was purified as His$_6$-protein. The fusion protein was induced from pET28-Hip (V. Prapapanich et al., Mol Cell Biol., 18:944-952, 1998, which is incorporated herein by reference) with 0.1mM IPTG at 25° C. for 6 h in BL21 cells. Cells from 1 L of culture were resuspended into 50 ml of 50 mM Phosphate buffer (pH 6.8), 150 mM NaCl, and 1% (v/v) TWEEN™-20 and then incubated with 0.5 mg/ml lysozyme at 25° C. for 0.5 h, followed by sonication. After centrifugation at 27,500 g for 10 min, the resulting supernatant was mixed with 15 ml nickel resin (Qiagen, Inc.) at 4° C. for 3 h with 25 mM imidazol. The resin was then washed with 50 mM phosphate buffer (pH 6.8), 25 mM imidazol, 150 mM NaCl and 0.1% TWEEN™-20 until the OD280 nm reached a value of <0.01. His$_6$-Hip protein was eluted with 250 mM imidazol in washing buffer (Qiagene, Inc.) and purified on MONO Q™ (HR10/10 Pharmacia) by FPLC using a linear gradient of 0.5M NaCl at pH 8.0, followed by dialysis in chaperone assay buffer.

In the refolding assay reactions, addition of purified Hip at equimolar concentrations relative to BAG-1 (beginning at residue 116 of SEQ ID NO:2), BAG-2 (SEQ ID NO:4), or BAG-3 (SEQ ID NO:6) (1.8 µM) completely negated the inhibitory effects of the BAG-family proteins on refolding of denatured luciferase (see FIG. 4C). These results demonstrate that the suppression of Hsc70 chaperone activity by BAG-family proteins is reversible, and that Hip antagonizes the effects of not only BAG-1 (beginning at residue 116 of SEQ ID NO:2), but also of BAG-2 (SEQ ID NO:4) and BAG-3 (SEQ ID NO:6).

In summary, these results demonstrate that BAG-family proteins all contain a conserved BAG domain near their C-terminus that binds Hsc70/Hsp70, and that human BAG-family proteins can bind with high affinity to the ATPase domain of Hsc70 and inhibit its chaperone activity through a Hip-repressable mechanism.

Example IV

Expanded Nucleic Acid and Amino Acid Sequences for Human BAG-3, BAG-4 and BAG-5

Following the procedures disclosed herein, the nucleic acid and amino acids sequences to human BAG-3, BAG-4 and BAG-5 were further expanded. The expanded sequences for BAG-3, BAG-4 and BAG-5 are shown in FIGS. 15, 16 and 17, respectively, with their respective sequence identification numbers, "SEQ ID NOs".

We claim:

1. A substantially purified nucleic acid molecule encoding the amino acid sequence of SEQ ID NO:8.

2. The nucleic acid molecule of claim 1, wherein said nucleic acid molecule has the nucleotide sequence SEQ ID NO:7.

3. A substantially purified nucleic acid molecule consisting of a fragment of at least 35 nucleotides of a nucleotide sequence, or the complement thereof, encoding a polypeptide comprising the amino acid sequence of SEQ ID NO:8.

4. The nucleic acid molecule of claim 3, wherein said fragment is at least 45 nucleotides.

5. The nucleic acid molecule of claim 3, wherein said fragment is at least 55 nucleotides.

6. A substantially purified nucleic acid molecule consisting of a fragment of at least 35 nucleotides of the nucleotide sequence of SEQ ID NO:7, or the complement thereof.

7. The nucleic acid molecule of claim 6, wherein said fragment is at least 45 nucleotides.

8. The nucleic acid molecule of claim 6, wherein said fragment is at least 55 nucleotides.

* * * * *

SEQUENCE LISTING

<160> NUMBER OF SEQ ID NOS: 24

<210> SEQ ID NO 1
<211> LENGTH: 1291
<212> TYPE: DNA
<213> ORGANISM: Homo sapiens
<220> FEATURE:
<221> NAME/KEY: CDS
<222> LOCATION: (46)..(1080)

<400> SEQUENCE: 1

```
acgccgcgct cagcttccat cgctgggcgg tcaacaagtg cgggc ctg gct cag cgc      57
                                                 Leu Ala Gln Arg
                                                   1 ggg ggg gcg cgg aga ccg cga ggc gac cgg gag cgg ctg ggt tcc cgg     105
Gly Gly Ala Arg Arg Pro Arg Gly Asp Arg Glu Arg Leu Gly Ser Arg
  5                  10                  15                  20 ctg cgc gcc ctt cgg cca ggc cgg gag ccg cgc cag tcg gag ccc ccg     153
Leu Arg Ala Leu Arg Pro Gly Arg Glu Pro Arg Gln Ser Glu Pro Pro
             25                  30                  35 gcc cag cgt ggt ccg cct ccc tct cgg cgt cca cct gcc cgg agt act     201
Ala Gln Arg Gly Pro Pro Pro Ser Arg Arg Pro Pro Ala Arg Ser Thr
         40                  45                  50 gcc agc ggg cat gac cga ccc acc agg ggc gcc gcc gcc ggc gct cgc     249
Ala Ser Gly His Asp Arg Pro Thr Arg Gly Ala Ala Ala Gly Ala Arg
     55                  60                  65 agg ccg cgg atg aag aag aaa acc cgg cgc cgc tcg acc cgg agc gag     297
Arg Pro Arg Met Lys Lys Lys Thr Arg Arg Arg Ser Thr Arg Ser Glu
 70                  75                  80 gag ttg acc cgg agc gag gag ttg acc ctg agt gag gaa gcg acc tgg     345
Glu Leu Thr Arg Ser Glu Glu Leu Thr Leu Ser Glu Glu Ala Thr Trp
 85                  90                  95                 100 agt gaa gag gcg acc cag agt gag gag gcg acc cag ggc gaa gag atg     393
Ser Glu Glu Ala Thr Gln Ser Glu Glu Ala Thr Gln Gly Glu Glu Met
                105                 110                 115 aat cgg agc cag gag gtg acc cgg gac gag gag tcg acc cgg agc gag     441
Asn Arg Ser Gln Glu Val Thr Arg Asp Glu Glu Ser Thr Arg Ser Glu
            120                 125                 130 gag gtg acc agg gag gaa atg gcg gca gct ggg ctc acc gtg act gtc     489
Glu Val Thr Arg Glu Glu Met Ala Ala Ala Gly Leu Thr Val Thr Val
        135                 140                 145 acc cac agc aat gag aag cac gac ctt cat gtt acc tcc cag cag ggc     537
Thr His Ser Asn Glu Lys His Asp Leu His Val Thr Ser Gln Gln Gly
    150                 155                 160 agc agt gaa cca gtt gtc caa gac ctg gcc cag gtt gtt gaa gag gtc     585
Ser Ser Glu Pro Val Val Gln Asp Leu Ala Gln Val Val Glu Glu Val
165                 170                 175                 180
```

| | | |
|---|---|---|
| ata ggg gtt cca cag tct ttt cag aaa ctc ata ttt aag gga aaa tct<br>Ile Gly Val Pro Gln Ser Phe Gln Lys Leu Ile Phe Lys Gly Lys Ser<br>                      185                      190                    195 | 633 |
| ctg aag gaa atg gaa aca ccg ttg tca gca ctt gga ata caa gat ggt<br>Leu Lys Glu Met Glu Thr Pro Leu Ser Ala Leu Gly Ile Gln Asp Gly<br>           200                      205                      210 | 681 |
| tgc cgg gtc atg tta att ggg aaa aag aac agt cca cag gaa gag gtt<br>Cys Arg Val Met Leu Ile Gly Lys Lys Asn Ser Pro Gln Glu Glu Val<br>               215                      220                    225 | 729 |
| gaa cta aag aag ttg aaa cat ttg gag aag tct gtg gag aag ata gct<br>Glu Leu Lys Lys Leu Lys His Leu Glu Lys Ser Val Glu Lys Ile Ala<br>    230                      235                      240 | 777 |
| gac cag ctg gaa gag ttg aat aaa gag ctt act gga atc cag cag ggt<br>Asp Gln Leu Glu Glu Leu Asn Lys Glu Leu Thr Gly Ile Gln Gln Gly<br>245                      250                      255                    260 | 825 |
| ttt ctg ccc aag gat ttg caa gct gaa gct ctc tgc aaa ctt gat agg<br>Phe Leu Pro Lys Asp Leu Gln Ala Glu Ala Leu Cys Lys Leu Asp Arg<br>               265                      270                    275 | 873 |
| aga gta aaa gcc aca ata gag cag ttt atg aag atc ttg gag gag att<br>Arg Val Lys Ala Thr Ile Glu Gln Phe Met Lys Ile Leu Glu Glu Ile<br>                    280                      285                    290 | 921 |
| gac aca ctg atc ctg cca gaa aat ttc aaa gac agt aga ttg aaa agg<br>Asp Thr Leu Ile Leu Pro Glu Asn Phe Lys Asp Ser Arg Leu Lys Arg<br>           295                      300                      305 | 969 |
| aaa ggc ttg gta aaa aag gtt cag gca ttc cta gcc gag tgt gac aca<br>Lys Gly Leu Val Lys Lys Val Gln Ala Phe Leu Ala Glu Cys Asp Thr<br>    310                      315                      320 | 1017 |
| gtg gag cag aac atc tgc cag gag act gag cgg ctg cag tct aca aac<br>Val Glu Gln Asn Ile Cys Gln Glu Thr Glu Arg Leu Gln Ser Thr Asn<br>325                      330                      335                    340 | 1065 |
| ttt gcc ctg gcc gag tgaggtgtag cagaaaaagg ctgtgctgcc ctgaagaatg<br>Phe Ala Leu Ala Glu<br>               345 | 1120 |
| gcgccaccag ctctgccgtc tctggatcgg aatttacctg atttcttcag ggctgctggg | 1180 |
| ggcaactggc catttgccaa ttttcctact ctcacactgg ttctcaatga aaaatagtgt | 1240 |
| ctttgtgatt tgagtaaagc tcctattctg tttttcacaa aaaaaaaaa a | 1291 |

<210> SEQ ID NO 2
<211> LENGTH: 345
<212> TYPE: PRT
<213> ORGANISM: Homo sapiens

<400> SEQUENCE: 2

Leu Ala Gln Arg Gly Gly Ala Arg Arg Pro Arg Gly Asp Arg Glu Arg
 1               5                  10                  15

Leu Gly Ser Arg Leu Arg Ala Leu Arg Pro Gly Arg Glu Pro Arg Gln
            20                  25                  30

Ser Glu Pro Pro Ala Gln Arg Gly Pro Pro Ser Arg Arg Pro Pro
        35                  40                  45

Ala Arg Ser Thr Ala Ser Gly His Asp Arg Pro Thr Arg Gly Ala Ala
    50                  55                  60

Ala Gly Ala Arg Arg Pro Arg Met Lys Lys Lys Thr Arg Arg Arg Ser
65                  70                  75                  80

Thr Arg Ser Glu Glu Leu Thr Arg Ser Glu Glu Leu Thr Leu Ser Glu
                85                  90                  95

Glu Ala Thr Trp Ser Glu Glu Ala Thr Gln Ser Glu Glu Ala Thr Gln
            100                 105                 110

```
Gly Glu Glu Met Asn Arg Ser Gln Glu Val Thr Arg Asp Glu Glu Ser
            115                 120                 125

Thr Arg Ser Glu Glu Val Thr Arg Glu Glu Met Ala Ala Ala Gly Leu
    130                 135                 140

Thr Val Thr Val Thr His Ser Asn Glu Lys His Asp Leu His Val Thr
145                 150                 155                 160

Ser Gln Gln Gly Ser Ser Glu Pro Val Val Gln Asp Leu Ala Gln Val
                165                 170                 175

Val Glu Glu Val Ile Gly Val Pro Gln Ser Phe Gln Lys Leu Ile Phe
            180                 185                 190

Lys Gly Lys Ser Leu Lys Glu Met Glu Thr Pro Leu Ser Ala Leu Gly
            195                 200                 205

Ile Gln Asp Gly Cys Arg Val Met Leu Ile Gly Lys Lys Asn Ser Pro
            210                 215                 220

Gln Glu Glu Val Glu Leu Lys Lys Leu Lys His Leu Glu Lys Ser Val
225                 230                 235                 240

Glu Lys Ile Ala Asp Gln Leu Glu Glu Leu Asn Lys Glu Leu Thr Gly
                245                 250                 255

Ile Gln Gln Gly Phe Leu Pro Lys Asp Leu Gln Ala Glu Ala Leu Cys
            260                 265                 270

Lys Leu Asp Arg Arg Val Lys Ala Thr Ile Glu Gln Phe Met Lys Ile
            275                 280                 285

Leu Glu Glu Ile Asp Thr Leu Ile Leu Pro Glu Asn Phe Lys Asp Ser
            290                 295                 300

Arg Leu Lys Arg Lys Gly Leu Val Lys Lys Val Gln Ala Phe Leu Ala
305                 310                 315                 320

Glu Cys Asp Thr Val Glu Gln Asn Ile Cys Gln Glu Thr Glu Arg Leu
                325                 330                 335

Gln Ser Thr Asn Phe Ala Leu Ala Glu
            340                 345

<210> SEQ ID NO 3
<211> LENGTH: 1179
<212> TYPE: DNA
<213> ORGANISM: Homo sapiens
<220> FEATURE:
<221> NAME/KEY: CDS
<222> LOCATION: (160)..(792)

<400> SEQUENCE: 3
gcagccgcgg tgtcgcgaag tcctcccggg ttgcccccgc ggcgtcagag ggagggcggg      60
cgccgcgttg gtgacggcga ccctgcagcc caaggagcgc tccactcgct gccgccggag     120
ggccggtgac ctcttggcta ccccgcgtcg gaggcttag atg gct cag gcg aag        174
                                             Met Ala Gln Ala Lys
                                               1               5 atc aac gct aaa gcc aac gag ggg cgc ttc tgc cgc tcc tcc tcc atg       222
Ile Asn Ala Lys Ala Asn Glu Gly Arg Phe Cys Arg Ser Ser Ser Met
              10                  15                  20 gct gac cgc tcc agc cgc ctg ctg gag agc ctg gac cag ctg gag ctc       270
Ala Asp Arg Ser Ser Arg Leu Leu Glu Ser Leu Asp Gln Leu Glu Leu
          25                  30                  35 agg gtt gaa gct ttg aga gaa gca gca act gct gtt gag caa gag aaa       318
Arg Val Glu Ala Leu Arg Glu Ala Ala Thr Ala Val Glu Gln Glu Lys
      40                  45                  50 gaa atc ctt ctg gaa atg atc cac agt atc caa aat agc cag gac atg       366
Glu Ile Leu Leu Glu Met Ile His Ser Ile Gln Asn Ser Gln Asp Met
  55                  60                  65
```

```
agg cag atc agt gac gga gaa aga gaa gaa tta aat ctg act gca aac     414
Arg Gln Ile Ser Asp Gly Glu Arg Glu Glu Leu Asn Leu Thr Ala Asn
         70                  75                  80              85 cgt ttg atg gga aga act ctc acc gtt gaa gtg tca gta gaa aca att     462
Arg Leu Met Gly Arg Thr Leu Thr Val Glu Val Ser Val Glu Thr Ile
                 90                  95                 100 aga aac ccc cag cag caa gaa tcc cta aag cat gcc aca agg att att     510
Arg Asn Pro Gln Gln Gln Glu Ser Leu Lys His Ala Thr Arg Ile Ile
                     105                 110                 115 gat gag gtg gtc aat aag ttt ctg gat gat ttg gga aat gcc aag agt     558
Asp Glu Val Val Asn Lys Phe Leu Asp Asp Leu Gly Asn Ala Lys Ser
             120                 125                 130 cat tta atg tcg ctc tac agt gca tgt tca tct gag gtg cca cat ggg     606
His Leu Met Ser Leu Tyr Ser Ala Cys Ser Ser Glu Val Pro His Gly
         135                 140                 145 cca gtt gat cag aag ttt caa tcc ata gta att ggc tgt gct ctt gaa     654
Pro Val Asp Gln Lys Phe Gln Ser Ile Val Ile Gly Cys Ala Leu Glu
150                 155                 160                 165 gat cag aag aaa att aag aga aga tta gag act ctg ctt aga aat att     702
Asp Gln Lys Lys Ile Lys Arg Arg Leu Glu Thr Leu Leu Arg Asn Ile
                 170                 175                 180 gaa aac tct gac aag gcc atc aag cta tta gag cat tct aaa gga gct     750
Glu Asn Ser Asp Lys Ala Ile Lys Leu Leu Glu His Ser Lys Gly Ala
             185                 190                 195 ggt tcc aaa act ctg caa caa aat gct gaa agc aga ttc aat             792
Gly Ser Lys Thr Leu Gln Gln Asn Ala Glu Ser Arg Phe Asn
         200                 205                 210 tagtcttcaa acctaagagc atttacacaa tacacaaggt gtaaaatga taaaatacta    852 ttttaattga taactagttc tttgttaggt ataaccactt agttgacact gatagttgtt   912
tcagatgagg aaaatattcc atcaagtatc ttcagttttg tgaataacaa aactagcaat   972 atttttaatta tctatctaga gattttttag attgaattct tgtcttgtac taggatctag 1032 catatttcac tattctgtgg atgaatacat agtttgtggg gaaaacaaac gttcagctag  1092
gggcaaaaag catgactgct ttttcctgtc tggcatggaa tcacgcagtc accttgggca  1152
tttagtttac tagaaattct ttactgg                                      1179

<210> SEQ ID NO 4
<211> LENGTH: 211
<212> TYPE: PRT
<213> ORGANISM: Homo sapiens

<400> SEQUENCE: 4

Met Ala Gln Ala Lys Ile Asn Ala Lys Ala Asn Glu Gly Arg Phe Cys
 1               5                  10                  15

Arg Ser Ser Ser Met Ala Asp Arg Ser Ser Arg Leu Leu Glu Ser Leu
                 20                  25                  30

Asp Gln Leu Glu Leu Arg Val Glu Ala Leu Arg Glu Ala Ala Thr Ala
             35                  40                  45

Val Glu Gln Glu Lys Glu Ile Leu Leu Glu Met Ile His Ser Ile Gln
         50                  55                  60

Asn Ser Gln Asp Met Arg Gln Ile Ser Asp Gly Glu Arg Glu Glu Leu
 65                  70                  75                  80

Asn Leu Thr Ala Asn Arg Leu Met Gly Arg Thr Leu Thr Val Glu Val
                 85                  90                  95

Ser Val Glu Thr Ile Arg Asn Pro Gln Gln Gln Glu Ser Leu Lys His
            100                 105                 110
```

```
Ala Thr Arg Ile Ile Asp Glu Val Val Asn Lys Phe Leu Asp Asp Leu
        115                 120                 125

Gly Asn Ala Lys Ser His Leu Met Ser Leu Tyr Ser Ala Cys Ser Ser
    130                 135                 140

Glu Val Pro His Gly Pro Val Asp Gln Lys Phe Gln Ser Ile Val Ile
145                 150                 155                 160

Gly Cys Ala Leu Glu Asp Gln Lys Lys Ile Lys Arg Arg Leu Glu Thr
                165                 170                 175

Leu Leu Arg Asn Ile Glu Asn Ser Asp Lys Ala Ile Lys Leu Leu Glu
            180                 185                 190

His Ser Lys Gly Ala Gly Ser Lys Thr Leu Gln Gln Asn Ala Glu Ser
        195                 200                 205

Arg Phe Asn
    210

<210> SEQ ID NO 5
<211> LENGTH: 2528
<212> TYPE: DNA
<213> ORGANISM: Homo sapiens
<220> FEATURE:
<221> NAME/KEY: CDS
<222> LOCATION: (1)..(2031)
<220> FEATURE:
<221> NAME/KEY: misc_feature
<222> LOCATION: (1)..(2528)
<223> OTHER INFORMATION: n= a, c, t or g

<400> SEQUENCE: 5 gcg gag ctc cgc atc caa ccc cgg gcc gcg gcc aac ttc tct gga ctg      48
Ala Glu Leu Arg Ile Gln Pro Arg Ala Ala Ala Asn Phe Ser Gly Leu
  1               5                  10                  15 gac cag aag ttt cta gcc ggc cag ttg cta cct ccc ttt atc tcc tcc      96
Asp Gln Lys Phe Leu Ala Gly Gln Leu Leu Pro Pro Phe Ile Ser Ser
             20                  25                  30 ttc ccc tct ggc agc gag gag gct att tcc aga cac ttc cac ccc tct     144
Phe Pro Ser Gly Ser Glu Glu Ala Ile Ser Arg His Phe His Pro Ser
         35                  40                  45 ctg gcc acg tca ccc ccg cct tta att cat aaa ggt gcc cgg cgc cgg     192
Leu Ala Thr Ser Pro Pro Pro Leu Ile His Lys Gly Ala Arg Arg Arg
     50                  55                  60 ctt ccc gga cac gtc ggc ggc gga gag ggg ccc acg gcg gcg gcc cgg     240
Leu Pro Gly His Val Gly Gly Gly Glu Gly Pro Thr Ala Ala Ala Arg
 65                  70                  75                  80 cca gag act cgg cgc ccg gag cca gcg ccc cgc acc cgc gcc cca gcg     288
Pro Glu Thr Arg Arg Pro Glu Pro Ala Pro Arg Thr Arg Ala Pro Ala
                 85                  90                  95 ggc aga ccc caa ccc agc atg agc gcc gcc acc cac tcg ccc atg atg     336
Gly Arg Pro Gln Pro Ser Met Ser Ala Ala Thr His Ser Pro Met Met
            100                 105                 110 cag gtg gcg tcc ggc aac ggt gac cgc gac cct ttg ccc ccc gga tgg     384
Gln Val Ala Ser Gly Asn Gly Asp Arg Asp Pro Leu Pro Pro Gly Trp
        115                 120                 125 gag atc aag atc gac ccg cag acc ggc tgg ccc ttc ttc gtg gac cac     432
Glu Ile Lys Ile Asp Pro Gln Thr Gly Trp Pro Phe Phe Val Asp His
    130                 135                 140 aac agc cgc acc act acg tgg aac gac ccg cgc gtg ccc tct gag ggc     480
Asn Ser Arg Thr Thr Thr Trp Asn Asp Pro Arg Val Pro Ser Glu Gly
145                 150                 155                 160 ccc aag gag act cca tcc tct gcc aat ggc cct tcc cgg gag ggc tct     528
Pro Lys Glu Thr Pro Ser Ser Ala Asn Gly Pro Ser Arg Glu Gly Ser
```

```
                   -continued
          165            170            175
agg ctg ccg cct gct agg gaa ggc cac cct gtg tac ccc cag ctc cga    576
Arg Leu Pro Pro Ala Arg Glu Gly His Pro Val Tyr Pro Gln Leu Arg
            180            185            190 cca ggc tac att ccc att cct gtg ctc cat gaa ggc gct gag aac cgg    624
Pro Gly Tyr Ile Pro Ile Pro Val Leu His Glu Gly Ala Glu Asn Arg
        195            200            205 cag gtg cac cct ttc cat gtc tat ccc cag cct ggg atg cag cga ttc    672
Gln Val His Pro Phe His Val Tyr Pro Gln Pro Gly Met Gln Arg Phe
    210            215            220 cga act gag gcg gca gca gcg gct cct cag agg tcc cag tca cct ctg    720
Arg Thr Glu Ala Ala Ala Ala Ala Pro Gln Arg Ser Gln Ser Pro Leu
225            230            235            240 cgg ggc atg cca gaa acc act cag cca gat aaa cag tgt gga cag gtg    768
Arg Gly Met Pro Glu Thr Thr Gln Pro Asp Lys Gln Cys Gly Gln Val
            245            250            255 gca gcg gcg gcg gca gcc cag ccc cca gcc tcc cac gga cct gag cgg    816
Ala Ala Ala Ala Ala Ala Gln Pro Pro Ala Ser His Gly Pro Glu Arg
        260            265            270 tcc cag tct cca gct gcc tct gac tgc tca tcc tca tcc tcg gcc        864
Ser Gln Ser Pro Ala Ala Ser Asp Cys Ser Ser Ser Ser Ser Ala
    275            280            285 agc ctg cct tcc tcc ggc agg agc agc ctg ggc agt cac cag ctc ccg    912
Ser Leu Pro Ser Ser Gly Arg Ser Ser Leu Gly Ser His Gln Leu Pro
290            295            300 cgg ggg tac atc tcc att ccg gtg ata cac gag cag aac gtt acc cgg    960
Arg Gly Tyr Ile Ser Ile Pro Val Ile His Glu Gln Asn Val Thr Arg
305            310            315            320 cca gca gcc cag ccc tcc ttc cac aaa gcc cag aag acg cac tac cca    1008
Pro Ala Ala Gln Pro Ser Phe His Lys Ala Gln Lys Thr His Tyr Pro
            325            330            335 gcg cag agg ggt gag tac cag acc cac cag cct gtg tac cac aag atc    1056
Ala Gln Arg Gly Glu Tyr Gln Thr His Gln Pro Val Tyr His Lys Ile
        340            345            350 cag ggg gat gac tgg gag ccc cgg ccc ctg cgg gcg gca tcc ccg ttc    1104
Gln Gly Asp Asp Trp Glu Pro Arg Pro Leu Arg Ala Ala Ser Pro Phe
    355            360            365 agg tca tct gtc cag ggt gca tcg agc cgg gag ggc tca cca gcc agg    1152
Arg Ser Ser Val Gln Gly Ala Ser Ser Arg Glu Gly Ser Pro Ala Arg
370            375            380 agc agc acg cca ctc cac tcc ccc tcg ccc atc cgt gtg cac acc gtg    1200
Ser Ser Thr Pro Leu His Ser Pro Ser Pro Ile Arg Val His Thr Val
385            390            395            400 gtc gac agg cct cag cag ccc atg acc cat cga gaa act gca cct gtt    1248
Val Asp Arg Pro Gln Gln Pro Met Thr His Arg Glu Thr Ala Pro Val
            405            410            415 tcc cag cct gaa aac aaa cca gaa agt aag cca ggc cca gtt gga cca    1296
Ser Gln Pro Glu Asn Lys Pro Glu Ser Lys Pro Gly Pro Val Gly Pro
        420            425            430 gaa ctc cct cct gga cac atc cca att caa gtg atc cgc aaa gag gtg    1344
Glu Leu Pro Pro Gly His Ile Pro Ile Gln Val Ile Arg Lys Glu Val
    435            440            445 gat tct aaa cct gtt tcc cag aag ccc cca cct ccc tct gag aag gta    1392
Asp Ser Lys Pro Val Ser Gln Lys Pro Pro Pro Pro Ser Glu Lys Val
450            455            460 gag gtg aaa gtt ccc cct gct cca gtt cct tgt cct cct ccc agc cct    1440
Glu Val Lys Val Pro Pro Ala Pro Val Pro Cys Pro Pro Pro Ser Pro
465            470            475            480 ggc cct tct gct gtc ccc tct tcc ccc aag agt gtg gct aca gaa gag    1488
Gly Pro Ser Ala Val Pro Ser Ser Pro Lys Ser Val Ala Thr Glu Glu
```

-continued

```
Gly Pro Ser Ala Val Pro Ser Ser Pro Lys Ser Val Ala Thr Glu Glu
                485                 490                 495 agg gca gcc ccc agc act gcc cct gca gaa gct aca cct cca aaa cca       1536
Arg Ala Ala Pro Ser Thr Ala Pro Ala Glu Ala Thr Pro Pro Lys Pro
                500                 505                 510 gga gaa gcc gag gct ccc cca aaa cat cca gga gtg ctg aaa gtg gaa       1584
Gly Glu Ala Glu Ala Pro Pro Lys His Pro Gly Val Leu Lys Val Glu
                515                 520                 525 gcc atc ctg gag aag gtg cag ggg ctg gag cag gct gta gac aac ttt       1632
Ala Ile Leu Glu Lys Val Gln Gly Leu Glu Gln Ala Val Asp Asn Phe
            530                 535                 540 gaa ggc aag aag act gac aaa aag tac ctg atg atc gaa gag tat ttg       1680
Glu Gly Lys Lys Thr Asp Lys Lys Tyr Leu Met Ile Glu Glu Tyr Leu
545                 550                 555                 560 acc aaa gag ctg ctg gcc ctg gat tca gtg gac ccc gag gga cga gcc       1728
Thr Lys Glu Leu Leu Ala Leu Asp Ser Val Asp Pro Glu Gly Arg Ala
                565                 570                 575 gat gtg cgt cag gcc agg aga gac ggt gtc agg aag gtt cag acc atc       1776
Asp Val Arg Gln Ala Arg Arg Asp Gly Val Arg Lys Val Gln Thr Ile
                580                 585                 590 ttg gaa aaa ctt gaa cag aaa gcc att gat gtc cca ggt caa gtc cag       1824
Leu Glu Lys Leu Glu Gln Lys Ala Ile Asp Val Pro Gly Gln Val Gln
                595                 600                 605 gtc tat gaa ctc cag ccc agc aac ctt gaa gca gat cag cca ctg cag       1872
Val Tyr Glu Leu Gln Pro Ser Asn Leu Glu Ala Asp Gln Pro Leu Gln
            610                 615                 620 gca atc atg gag atg ggt gcc gtg gca gca gac aag ggc aag aaa aat       1920
Ala Ile Met Glu Met Gly Ala Val Ala Ala Asp Lys Gly Lys Lys Asn
625                 630                 635                 640 gct gga aat gca gaa gat ccc cac aca gaa acc cag cag cca gaa gcc       1968
Ala Gly Asn Ala Glu Asp Pro His Thr Glu Thr Gln Gln Pro Glu Ala
                645                 650                 655 aca gca gca gcg act tca aac ccc agc agc atg aca gac acc cct ggt       2016
Thr Ala Ala Ala Thr Ser Asn Pro Ser Ser Met Thr Asp Thr Pro Gly
                660                 665                 670 aac cca gca gca ccg tagcctctgc cctgtaaaag tcagactcgg aaccgatgtg       2071
Asn Pro Ala Ala Pro
            675 tgctttaggg attttagttg catgcatttc agagacttta ggtcagttgg ttttgattag    2131 ctgcttggta tgcagtactt gggtgaggca aacactataa agggctaaaa gggaaaatga    2191 tgctttcttt caatattctt actcttgtac aattaangaa gttgcttgtt gtttgagaag    2251 tttaacccg ttgcttgttc tgcagccctg tcnacttggg cacccccacc acctgttagc    2311 tgtggttgtg cactgtcttt tgtagctctg gactggaggg gtagatgggg agtcaattac    2371 ccatcacata aatatgaaac atttatcaga aatgttgcca ttttaatgag atgattttct    2431 tcatctcata attaaaatac ctgactttag agagagtaaa atgtgccagg agccatagga    2491 atatctgtat gttggatgac tttaatgcta cattth                              2528

<210> SEQ ID NO 6
<211> LENGTH: 677
<212> TYPE: PRT
<213> ORGANISM: Homo sapiens

<400> SEQUENCE: 6

Ala Glu Leu Arg Ile Gln Pro Arg Ala Ala Asn Phe Ser Gly Leu
  1               5                  10                  15

Asp Gln Lys Phe Leu Ala Gly Gln Leu Leu Pro Pro Phe Ile Ser Ser
```

```
                    20                  25                  30
Phe Pro Ser Gly Ser Glu Glu Ala Ile Ser Arg His Phe His Pro Ser
            35                  40                  45

Leu Ala Thr Ser Pro Pro Leu Ile His Lys Gly Ala Arg Arg Arg
    50                  55                  60

Leu Pro Gly His Val Gly Gly Glu Gly Pro Thr Ala Ala Ala Arg
65                  70                  75                  80

Pro Glu Thr Arg Arg Pro Glu Pro Ala Pro Arg Thr Arg Ala Pro Ala
                85                  90                  95

Gly Arg Pro Gln Pro Ser Met Ser Ala Ala Thr His Ser Pro Met Met
                100                 105                 110

Gln Val Ala Ser Gly Asn Gly Asp Arg Asp Pro Leu Pro Gly Trp
        115                 120                 125

Glu Ile Lys Ile Asp Pro Gln Thr Gly Trp Pro Phe Phe Val Asp His
        130                 135                 140

Asn Ser Arg Thr Thr Thr Trp Asn Asp Pro Arg Val Pro Ser Glu Gly
145                 150                 155                 160

Pro Lys Glu Thr Pro Ser Ser Ala Asn Gly Pro Ser Arg Glu Gly Ser
                165                 170                 175

Arg Leu Pro Pro Ala Arg Glu Gly His Pro Val Tyr Pro Gln Leu Arg
                180                 185                 190

Pro Gly Tyr Ile Pro Ile Pro Val Leu His Glu Gly Ala Glu Asn Arg
            195                 200                 205

Gln Val His Pro Phe His Val Tyr Pro Gln Pro Gly Met Gln Arg Phe
        210                 215                 220

Arg Thr Glu Ala Ala Ala Ala Ala Pro Gln Arg Ser Gln Ser Pro Leu
225                 230                 235                 240

Arg Gly Met Pro Glu Thr Thr Gln Pro Asp Lys Gln Cys Gly Gln Val
                245                 250                 255

Ala Ala Ala Ala Ala Ala Gln Pro Pro Ala Ser His Gly Pro Glu Arg
                260                 265                 270

Ser Gln Ser Pro Ala Ala Ser Asp Cys Ser Ser Ser Ser Ser Ser Ala
            275                 280                 285

Ser Leu Pro Ser Ser Gly Arg Ser Ser Leu Gly Ser His Gln Leu Pro
    290                 295                 300

Arg Gly Tyr Ile Ser Ile Pro Val Ile His Glu Gln Asn Val Thr Arg
305                 310                 315                 320

Pro Ala Ala Gln Pro Ser Phe His Lys Ala Gln Lys Thr His Tyr Pro
                325                 330                 335

Ala Gln Arg Gly Glu Tyr Gln Thr His Gln Pro Val Tyr His Lys Ile
            340                 345                 350

Gln Gly Asp Asp Trp Glu Pro Arg Pro Leu Arg Ala Ala Ser Pro Phe
        355                 360                 365

Arg Ser Ser Val Gln Gly Ala Ser Ser Arg Glu Gly Ser Pro Ala Arg
    370                 375                 380

Ser Ser Thr Pro Leu His Ser Pro Ser Pro Ile Arg Val His Thr Val
385                 390                 395                 400

Val Asp Arg Pro Gln Gln Pro Met Thr His Arg Glu Thr Ala Pro Val
                405                 410                 415

Ser Gln Pro Glu Asn Lys Pro Glu Ser Lys Pro Gly Pro Val Gly Pro
                420                 425                 430

Glu Leu Pro Pro Gly His Ile Pro Ile Gln Val Ile Arg Lys Glu Val
            435                 440                 445
```

```
Asp Ser Lys Pro Val Ser Gln Lys Pro Pro Pro Ser Glu Lys Val
    450                 455                 460
Glu Val Lys Val Pro Ala Pro Val Pro Cys Pro Pro Ser Pro
465                 470                 475                 480
Gly Pro Ser Ala Val Pro Ser Ser Pro Lys Ser Val Ala Thr Glu Glu
                485                 490                 495
Arg Ala Ala Pro Ser Thr Ala Pro Ala Glu Ala Thr Pro Pro Lys Pro
                500                 505                 510
Gly Glu Ala Glu Ala Pro Pro Lys His Pro Gly Val Leu Lys Val Glu
            515                 520                 525
Ala Ile Leu Glu Lys Val Gln Gly Leu Glu Gln Ala Val Asp Asn Phe
    530                 535                 540
Glu Gly Lys Lys Thr Asp Lys Lys Tyr Leu Met Ile Glu Glu Tyr Leu
545                 550                 555                 560
Thr Lys Glu Leu Leu Ala Leu Asp Ser Val Asp Pro Glu Gly Arg Ala
                565                 570                 575
Asp Val Arg Gln Ala Arg Arg Asp Gly Val Arg Lys Val Gln Thr Ile
                580                 585                 590
Leu Glu Lys Leu Glu Gln Lys Ala Ile Asp Val Pro Gly Gln Val Gln
            595                 600                 605
Val Tyr Glu Leu Gln Pro Ser Asn Leu Glu Ala Asp Gln Pro Leu Gln
    610                 615                 620
Ala Ile Met Glu Met Gly Ala Val Ala Ala Asp Lys Gly Lys Lys Asn
625                 630                 635                 640
Ala Gly Asn Ala Glu Asp Pro His Thr Glu Thr Gln Gln Pro Glu Ala
                645                 650                 655
Thr Ala Ala Thr Ser Asn Pro Ser Ser Met Thr Asp Thr Pro Gly
                660                 665                 670
Asn Pro Ala Ala Pro
        675

<210> SEQ ID NO 7
<211> LENGTH: 1010
<212> TYPE: DNA
<213> ORGANISM: Homo sapiens
<220> FEATURE:
<221> NAME/KEY: CDS
<222> LOCATION: (323)..(1009)

<400> SEQUENCE: 7
acgatatcct gtaagaccaa gaattgcaag gccagagttt gaattcttat acaaatggag      60
cgtatggtcc aacataccc ccaggccctg gggcaaatac tgcctcatac tcagggctt     120 attatgcacc tggttatact cagaccagtt actccacaga agttccaagt acttaccgtt    180
catctggcaa cagcccaact ccagtctctc gttggatcta tccccagcag gactgtcaag    240
actgaagcac ccctcttaa ggggcaggtt ccaggatatc cgccttcaca gaaccctgga     300
atgaccctgc ccattatcc tt atg gag atg gta atc gta gtg ttc cac aat      352
                        Met Glu Met Val Ile Val Val Phe His Asn
                         1               5                  10 cac ggc cga ctg tac gac cac aag aaa gat gcg tgg gct tct cct ggt      400
His Gly Arg Leu Tyr Asp His Lys Lys Asp Ala Trp Ala Ser Pro Gly
             15                  20                  25 gct tat gga atg ggt ggc cgt tat ccc tgg cct tca tca gcg ccc tca      448
Ala Tyr Gly Met Gly Gly Arg Tyr Pro Trp Pro Ser Ser Ala Pro Ser
         30                  35                  40
```

-continued

```
gca cca ccc ggc aat ctc tac atg act gaa agt act tca cca tgg cct     496
Ala Pro Pro Gly Asn Leu Tyr Met Thr Glu Ser Thr Ser Pro Trp Pro
         45                  50                  55 agc agt ggc tct ccc cag tca ccc cct tca ccc cca gtc cag cag ccc     544
Ser Ser Gly Ser Pro Gln Ser Pro Pro Ser Pro Pro Val Gln Gln Pro
 60                  65                  70 aag gat tct tca tac ccc tat agc caa tca gat caa agc atg aac cgg     592
Lys Asp Ser Ser Tyr Pro Tyr Ser Gln Ser Asp Gln Ser Met Asn Arg
 75                  80                  85                  90 cac aac ttt cct tgc agt gtc cat cag tac gaa tcc tcg ggg aca gtg     640
His Asn Phe Pro Cys Ser Val His Gln Tyr Glu Ser Ser Gly Thr Val
                 95                  100                 105 aac aat gat gat tca gat ctt ttg gat tcc caa gtc cag tat agt gct     688
Asn Asn Asp Asp Ser Asp Leu Leu Asp Ser Gln Val Gln Tyr Ser Ala
             110                 115                 120 gag cct cag ctg tat ggt aat gcc acc agt gac cat ccc aac aat caa     736
Glu Pro Gln Leu Tyr Gly Asn Ala Thr Ser Asp His Pro Asn Asn Gln
         125                 130                 135 gat caa agt agc agt ctt cct gaa gaa tgt gta cct tca gat gaa agt     784
Asp Gln Ser Ser Ser Leu Pro Glu Glu Cys Val Pro Ser Asp Glu Ser
 140                 145                 150 act cct ccg agt att aaa aaa atc ata cat gtg ctg gag aag gtc cag     832
Thr Pro Pro Ser Ile Lys Lys Ile Ile His Val Leu Glu Lys Val Gln
155                 160                 165                 170 tat ctt gaa caa gaa gta gaa gaa ttt gta gga aaa aag aca gac aaa     880
Tyr Leu Glu Gln Glu Val Glu Glu Phe Val Gly Lys Lys Thr Asp Lys
                 175                 180                 185 gca tac tgg ctt ctg gaa gaa atg cta acc aag gaa ctt ttg gaa ctg     928
Ala Tyr Trp Leu Leu Glu Glu Met Leu Thr Lys Glu Leu Leu Glu Leu
             190                 195                 200 gat tca gtt gaa act ggg ggc cag gac tct gta cgg cag gcc aga aaa     976
Asp Ser Val Glu Thr Gly Gly Gln Asp Ser Val Arg Gln Ala Arg Lys
         205                 210                 215 gag gct gtt tgt aag att cag gcc ata ttg gaa a                      1010
Glu Ala Val Cys Lys Ile Gln Ala Ile Leu Glu
 220                 225
```

<210> SEQ ID NO 8
<211> LENGTH: 229
<212> TYPE: PRT
<213> ORGANISM: Homo sapiens

<400> SEQUENCE: 8

```
Met Glu Met Val Ile Val Val Phe His Asn His Gly Arg Leu Tyr Asp
 1               5                  10                  15

His Lys Lys Asp Ala Trp Ala Ser Pro Gly Ala Tyr Gly Met Gly Gly
             20                  25                  30

Arg Tyr Pro Trp Pro Ser Ser Ala Pro Ser Ala Pro Pro Gly Asn Leu
         35                  40                  45

Tyr Met Thr Glu Ser Thr Ser Pro Trp Pro Ser Ser Gly Ser Pro Gln
 50                  55                  60

Ser Pro Pro Ser Pro Pro Val Gln Gln Pro Lys Asp Ser Ser Tyr Pro
 65                  70                  75                  80

Tyr Ser Gln Ser Asp Gln Ser Met Asn Arg His Asn Phe Pro Cys Ser
                 85                  90                  95

Val His Gln Tyr Glu Ser Ser Gly Thr Val Asn Asn Asp Asp Ser Asp
             100                 105                 110

Leu Leu Asp Ser Gln Val Gln Tyr Ser Ala Glu Pro Gln Leu Tyr Gly
         115                 120                 125
```

```
Asn Ala Thr Ser Asp His Pro Asn Asn Gln Asp Gln Ser Ser Ser Leu
        130                 135                 140

Pro Glu Glu Cys Val Pro Ser Asp Glu Ser Thr Pro Pro Ser Ile Lys
145                 150                 155                 160

Lys Ile Ile His Val Leu Glu Lys Val Gln Tyr Leu Glu Gln Glu Val
                165                 170                 175

Glu Glu Phe Val Gly Lys Lys Thr Asp Lys Ala Tyr Trp Leu Leu Glu
            180                 185                 190

Glu Met Leu Thr Lys Glu Leu Leu Glu Leu Asp Ser Val Glu Thr Gly
        195                 200                 205

Gly Gln Asp Ser Val Arg Gln Ala Arg Lys Glu Ala Val Cys Lys Ile
    210                 215                 220

Gln Ala Ile Leu Glu
225

<210> SEQ ID NO 9
<211> LENGTH: 689
<212> TYPE: DNA
<213> ORGANISM: Homo sapiens
<220> FEATURE:
<221> NAME/KEY: CDS
<222> LOCATION: (3)..(482)
<220> FEATURE:
<221> NAME/KEY: unsure
<222> LOCATION: (105)
<223> OTHER INFORMATION: any amino acid
<220> FEATURE:
<221> NAME/KEY: misc_feature
<222> LOCATION: (1)..(659)
<223> OTHER INFORMATION: n= a, c, to or g

<400> SEQUENCE: 9 ga gaa ata aaa aat gaa ctt ctc caa gca caa aac cct tct gaa ttg         47
   Glu Ile Lys Asn Glu Leu Leu Gln Ala Gln Asn Pro Ser Glu Leu
   1               5                  10                  15 tac ctg agc tcc aaa aca gaa ttg cag ggt tta att gga cag ttg gat        95
Tyr Leu Ser Ser Lys Thr Glu Leu Gln Gly Leu Ile Gly Gln Leu Asp
                20                  25                  30 gag gta agt ntt gaa aaa aac ccc tgc atc cgg gaa gcc agg aga aga       143
Glu Val Ser Xaa Glu Lys Asn Pro Cys Ile Arg Glu Ala Arg Arg Arg
            35                  40                  45 gca gtg atc gag gtg caa act ctg atc aca tat att gac ttg aag gag       191
Ala Val Ile Glu Val Gln Thr Leu Ile Thr Tyr Ile Asp Leu Lys Glu
        50                  55                  60 gcc ctt gag aaa aga aag ctg ttt gct tgt gag gag cac cca tcc cat       239
Ala Leu Glu Lys Arg Lys Leu Phe Ala Cys Glu Glu His Pro Ser His
65                  70                  75 aaa gcc gtc tgg aac gtc ctt gga aac ttg tct gag atc cag gga gaa       287
Lys Ala Val Trp Asn Val Leu Gly Asn Leu Ser Glu Ile Gln Gly Glu
80                  85                  90                  95 gtt ctt tca ttt gat gga aat cga acc gat aag aac tac atc cgg ctg       335
Val Leu Ser Phe Asp Gly Asn Arg Thr Asp Lys Asn Tyr Ile Arg Leu
                100                 105                 110 gaa gag ctg ctc acc aag cag ctg cta gcc ctg gat gct gtt gat ccg       383
Glu Glu Leu Leu Thr Lys Gln Leu Leu Ala Leu Asp Ala Val Asp Pro
            115                 120                 125 cag gga gaa gag aag tgt aag gct gcc agg aaa caa gct gtg agg ctt       431
Gln Gly Glu Glu Lys Cys Lys Ala Ala Arg Lys Gln Ala Val Arg Leu
        130                 135                 140 gcg cag aat att ctc agc tat ctc gac ctg aaa tct gat gaa tgg gag       479
Ala Gln Asn Ile Leu Ser Tyr Leu Asp Leu Lys Ser Asp Glu Trp Glu
```

-continued

```
               145                 150                 155
tac tgaaatacca gagatctcac ttttgatact gttttgcact tcatatgtgc         532
Tyr
160 ttctatgtat agagagcttt cagttcattg atttatacgt gcatatttca gtctcagtat    592 ttatgattga agcaaattct attcagtatc tgctgctttt gatgttgcaa gacaaatatc   652 attacagcac gttaactttt ccattcggat caaaaaa                            689

<210> SEQ ID NO 10
<211> LENGTH: 160
<212> TYPE: PRT
<213> ORGANISM: Homo sapiens
<220> FEATURE:
<221> NAME/KEY: unsure
<222> LOCATION: 1..160
<223> OTHER INFORMATION: Xaa=any amino acid

<400> SEQUENCE: 10

Glu Ile Lys Asn Glu Leu Leu Gln Ala Gln Asn Pro Ser Glu Leu Tyr
 1               5                  10                  15

Leu Ser Ser Lys Thr Glu Leu Gln Gly Leu Ile Gly Gln Leu Asp Glu
             20                  25                  30

Val Ser Xaa Glu Lys Asn Pro Cys Ile Arg Glu Ala Arg Arg Arg Ala
         35                  40                  45

Val Ile Glu Val Gln Thr Leu Ile Thr Tyr Ile Asp Leu Lys Glu Ala
     50                  55                  60

Leu Glu Lys Arg Lys Leu Phe Ala Cys Glu Glu His Pro Ser His Lys
 65                  70                  75                  80

Ala Val Trp Asn Val Leu Gly Asn Leu Ser Glu Ile Gln Gly Glu Val
                 85                  90                  95

Leu Ser Phe Asp Gly Asn Arg Thr Asp Lys Asn Tyr Ile Arg Leu Glu
            100                 105                 110

Glu Leu Leu Thr Lys Gln Leu Leu Ala Leu Asp Ala Val Asp Pro Gln
        115                 120                 125

Gly Glu Glu Lys Cys Lys Ala Ala Arg Lys Gln Ala Val Arg Leu Ala
    130                 135                 140

Gln Asn Ile Leu Ser Tyr Leu Asp Leu Lys Ser Asp Glu Trp Glu Tyr
145                 150                 155                 160

<210> SEQ ID NO 11
<211> LENGTH: 246
<212> TYPE: DNA
<213> ORGANISM: Caenorhabditis elegans

<400> SEQUENCE: 11
atgtctttcc gcctcttcgt tgaaatattt cactttcttt tccagctttt tccccatctc    60
gacctgcttt ggttttcga gaaaccacg ttccaaatca gcgacatctc tcaaattgag    120
atcataggct ttttgaagat tgctcaaatt atgcttctca tattgcatga gcattttgaa    180
gcccgcgtca tcaaccaaag cattttttcc acccatcaca atgatttat catttctttt    240 aaaatt                                                             246

<210> SEQ ID NO 12
<211> LENGTH: 210
<212> TYPE: PRT
<213> ORGANISM: Caenorhabditis elegans

<400> SEQUENCE: 12
```

```
Met Lys Val Asn Val Ser Cys Ser Ser Val Gln Thr Thr Ile Asp Ile
  1               5                  10                  15

Leu Glu Glu Asn Gln Gly Glu Asp Glu Ser Ile Leu Thr Leu Gly Gln
             20                  25                  30

Leu Arg Asp Arg Ile Ala Thr Asp Asn Asp Val Asp Val Glu Thr Met
         35                  40                  45

Lys Leu Leu His Arg Gly Lys Phe Leu Gln Gly Ala Asp Asp Val Ser
 50                  55                  60

Leu Ser Thr Leu Asn Phe Lys Glu Asn Asp Lys Ile Ile Val Met Gly
 65                  70                  75                  80

Gly Lys Asn Ala Leu Val Asp Asp Ala Gly Phe Lys Met Leu Met Gln
             85                  90                  95

Tyr Glu Lys His Asn Leu Ser Asn Leu Gln Lys Ala Tyr Asp Leu Asn
            100                 105                 110

Leu Arg Asp Val Ala Asp Leu Glu Arg Gly Phe Leu Glu Lys Pro Lys
        115                 120                 125

Gln Val Glu Met Gly Lys Lys Leu Glu Lys Lys Val Lys Tyr Phe Asn
    130                 135                 140

Glu Glu Ala Glu Arg His Leu Glu Thr Leu Asp Gly Met Asn Ile Ile
145                 150                 155                 160

Thr Glu Thr Thr Pro Glu Asn Gln Ala Lys Arg Asn Arg Glu Lys Arg
                165                 170                 175

Lys Thr Leu Val Asn Gly Ile Gln Thr Leu Leu Asn Gln Asn Asp Ala
            180                 185                 190

Leu Leu Arg Arg Leu Gln Glu Tyr Gln Ser Val Leu Asn Gly Asp Ile
        195                 200                 205

Pro Glu
    210

<210> SEQ ID NO 13
<211> LENGTH: 1377
<212> TYPE: DNA
<213> ORGANISM: Caenorhabditis elegans
<220> FEATURE:
<221> NAME/KEY: CDS
<222> LOCATION: (1)..(1377)

<400> SEQUENCE: 13 atg cca gtc gtg aac ata cca atc aaa ata ctt ggt cag aat caa tca        48
Met Pro Val Val Asn Ile Pro Ile Lys Ile Leu Gly Gln Asn Gln Ser
  1               5                  10                  15 cat agt cga agt aac tcc tcg tct tct gtt gac aac gat cga aat caa        96
His Ser Arg Ser Asn Ser Ser Ser Ser Val Asp Asn Asp Arg Asn Gln
             20                  25                  30 cca cca cag cag cca cct caa ccg caa cca caa cag caa tct cag caa       144
Pro Pro Gln Gln Pro Pro Gln Pro Gln Pro Gln Gln Gln Ser Gln Gln
         35                  40                  45 caa tac cag cag gct cca aac gtg aat acc aat atg cat cat tcc aac       192
Gln Tyr Gln Gln Ala Pro Asn Val Asn Thr Asn Met His His Ser Asn
 50                  55                  60 gga ttc tca cct aac ttc cca tct cgt agt cct att ccg gac ttt ccc       240
Gly Phe Ser Pro Asn Phe Pro Ser Arg Ser Pro Ile Pro Asp Phe Pro
 65                  70                  75                  80 agt ttt tca tct ggg ttc cca aac gat tct gaa tgg tct tcg aat ttc       288
Ser Phe Ser Ser Gly Phe Pro Asn Asp Ser Glu Trp Ser Ser Asn Phe
             85                  90                  95 ccg tcg ttt cca aat ttc cca agt gga ttc tca aat gga agt tct aat       336
```

```
               Pro Ser Phe Pro Asn Phe Pro Ser Gly Phe Ser Asn Gly Ser Ser Asn
                           100                 105                 110 ttc cct gat ttt cca aga ttc gga aga gat gga gga cta tcg cca aac        384
Phe Pro Asp Phe Pro Arg Phe Gly Arg Asp Gly Gly Leu Ser Pro Asn
            115                 120                 125 cca ccg atg caa gga tac agg aga agt cca aca cca aca tca act caa        432
Pro Pro Met Gln Gly Tyr Arg Arg Ser Pro Thr Pro Thr Ser Thr Gln
130                 135                 140 tct cca act tct aca tta aga cgc aac tct cag cag aat caa gct cct        480
Ser Pro Thr Ser Thr Leu Arg Arg Asn Ser Gln Gln Asn Gln Ala Pro
145                 150                 155                 160 cca caa tat tct cag caa caa cca caa caa gct caa caa cgt cag aca        528
Pro Gln Tyr Ser Gln Gln Gln Pro Gln Gln Ala Gln Gln Arg Gln Thr
                165                 170                 175 act cct ccg tca aca aaa gct tca tct cga cca cca tct cgt act cgt        576
Thr Pro Pro Ser Thr Lys Ala Ser Ser Arg Pro Pro Ser Arg Thr Arg
                180                 185                 190 gaa cca aag gaa cct gag gta ccc gag aga cca gca gtt att cca ttg        624
Glu Pro Lys Glu Pro Glu Val Pro Glu Arg Pro Ala Val Ile Pro Leu
            195                 200                 205 cca tat gag aag aag gag aaa cca ctg gag aag aaa ggt agt cgt gat        672
Pro Tyr Glu Lys Lys Glu Lys Pro Leu Glu Lys Lys Gly Ser Arg Asp
210                 215                 220 tct gga aag ggt gat gag aac ctt gaa gag aac att gcc aag atc acg        720
Ser Gly Lys Gly Asp Glu Asn Leu Glu Glu Asn Ile Ala Lys Ile Thr
225                 230                 235                 240 atc gga aag aat aat tgc gag tta tgt ccg gaa caa gaa acg gac ggc        768
Ile Gly Lys Asn Asn Cys Glu Leu Cys Pro Glu Gln Glu Thr Asp Gly
                245                 250                 255 gac cca tct cca cta acc tcc cca atc acc gaa gga aag cca aag aga        816
Asp Pro Ser Pro Leu Thr Ser Pro Ile Thr Glu Gly Lys Pro Lys Arg
                260                 265                 270 gga aag aaa ctt caa cgt aat caa agt gtt gtt gat ttc aat gcc aag        864
Gly Lys Lys Leu Gln Arg Asn Gln Ser Val Val Asp Phe Asn Ala Lys
            275                 280                 285 aca att gtt act ttg gat aaa att gaa tta caa gtt gag cag ttg aga        912
Thr Ile Val Thr Leu Asp Lys Ile Glu Leu Gln Val Glu Gln Leu Arg
290                 295                 300 aaa aaa gct gct gaa ctc gaa atg gaa aaa gag caa att ctt cgt tct        960
Lys Lys Ala Ala Glu Leu Glu Met Glu Lys Glu Gln Ile Leu Arg Ser
305                 310                 315                 320 cta gga gaa atc agt gtt cat aac tgc atg ttc aaa ctg gaa gaa tgt       1008
Leu Gly Glu Ile Ser Val His Asn Cys Met Phe Lys Leu Glu Glu Cys
                325                 330                 335 gat cgt gaa gag att gaa gca atc act gac cga ttg aca aaa aga aca       1056
Asp Arg Glu Glu Ile Glu Ala Ile Thr Asp Arg Leu Thr Lys Arg Thr
                340                 345                 350 aag aca gtt caa gtt gtt gtc gaa act cca cga aat gaa gaa cag aaa       1104
Lys Thr Val Gln Val Val Val Glu Thr Pro Arg Asn Glu Glu Gln Lys
            355                 360                 365 aaa gca ctg gaa gat gca act ttg atg atc gat gaa gtc gga gaa atg       1152
Lys Ala Leu Glu Asp Ala Thr Leu Met Ile Asp Glu Val Gly Glu Met
370                 375                 380 atg cat tcg aat att gaa aag gct aag ctg tgc cta caa acc tac atg       1200
Met His Ser Asn Ile Glu Lys Ala Lys Leu Cys Leu Gln Thr Tyr Met
385                 390                 395                 400 aac gcc tgt tcg tac gaa gaa act gct gga gcc acc tgc caa aac ttc       1248
Asn Ala Cys Ser Tyr Glu Glu Thr Ala Gly Ala Thr Cys Gln Asn Phe
                405                 410                 415
```

```
ttg aag atc ata att cag tgc gct gct gat gat cag aaa cgc atc aag    1296
Leu Lys Ile Ile Ile Gln Cys Ala Ala Asp Asp Gln Lys Arg Ile Lys
        420                 425                 430 cgt cgt ctg gaa aat ctg atg tct caa att gag aat gct gag aga acg    1344
Arg Arg Leu Glu Asn Leu Met Ser Gln Ile Glu Asn Ala Glu Arg Thr
            435                 440                 445 aaa gca gat ttg atg gat gat caa agc gaa tag                        1377
Lys Ala Asp Leu Met Asp Asp Gln Ser Glu
450                 455
```

<210> SEQ ID NO 14
<211> LENGTH: 458
<212> TYPE: PRT
<213> ORGANISM: Caenorhabditis elegans

<400> SEQUENCE: 14

```
Met Pro Val Val Asn Ile Pro Ile Lys Ile Leu Gly Gln Asn Gln Ser
 1               5                  10                  15

His Ser Arg Ser Asn Ser Ser Ser Val Asp Asn Asp Arg Asn Gln
            20                  25                  30

Pro Pro Gln Gln Pro Gln Pro Gln Pro Gln Gln Gln Ser Gln Gln
        35                  40                  45

Gln Tyr Gln Gln Ala Pro Asn Val Asn Thr Asn Met His His Ser Asn
    50                  55                  60

Gly Phe Ser Pro Asn Phe Pro Ser Arg Ser Pro Ile Pro Asp Phe Pro
65                  70                  75                  80

Ser Phe Ser Ser Gly Phe Pro Asn Asp Ser Glu Trp Ser Ser Asn Phe
                85                  90                  95

Pro Ser Phe Pro Asn Phe Pro Ser Gly Phe Ser Asn Gly Ser Ser Asn
            100                 105                 110

Phe Pro Asp Phe Pro Arg Phe Gly Arg Asp Gly Gly Leu Ser Pro Asn
        115                 120                 125

Pro Pro Met Gln Gly Tyr Arg Arg Ser Pro Thr Pro Thr Ser Thr Gln
    130                 135                 140

Ser Pro Thr Ser Thr Leu Arg Arg Asn Ser Gln Gln Asn Gln Ala Pro
145                 150                 155                 160

Pro Gln Tyr Ser Gln Gln Pro Gln Gln Ala Gln Gln Arg Gln Thr
                165                 170                 175

Thr Pro Pro Ser Thr Lys Ala Ser Ser Arg Pro Pro Ser Arg Thr Arg
            180                 185                 190

Glu Pro Lys Glu Pro Glu Val Pro Glu Arg Pro Ala Val Ile Pro Leu
        195                 200                 205

Pro Tyr Glu Lys Lys Glu Lys Pro Leu Glu Lys Lys Gly Ser Arg Asp
    210                 215                 220

Ser Gly Lys Gly Asp Glu Asn Leu Glu Glu Asn Ile Ala Lys Ile Thr
225                 230                 235                 240

Ile Gly Lys Asn Asn Cys Glu Leu Cys Pro Glu Gln Glu Thr Asp Gly
                245                 250                 255

Asp Pro Ser Pro Leu Thr Ser Pro Ile Thr Glu Gly Lys Pro Lys Arg
            260                 265                 270

Gly Lys Lys Leu Gln Arg Asn Gln Ser Val Val Asp Phe Asn Ala Lys
        275                 280                 285

Thr Ile Val Thr Leu Asp Lys Ile Glu Leu Gln Val Glu Gln Leu Arg
    290                 295                 300

Lys Lys Ala Ala Glu Leu Glu Met Glu Lys Glu Gln Ile Leu Arg Ser
305                 310                 315                 320
```

```
Leu Gly Glu Ile Ser Val His Asn Cys Met Phe Lys Leu Glu Cys
                325                 330                 335

Asp Arg Glu Glu Ile Glu Ala Ile Thr Asp Arg Leu Thr Lys Arg Thr
            340                 345                 350

Lys Thr Val Gln Val Val Glu Thr Pro Arg Asn Glu Glu Gln Lys
            355                 360                 365

Lys Ala Leu Glu Asp Ala Thr Leu Met Ile Asp Glu Val Gly Glu Met
    370                 375                 380

Met His Ser Asn Ile Glu Lys Ala Lys Leu Cys Leu Gln Thr Tyr Met
385                 390                 395                 400

Asn Ala Cys Ser Tyr Glu Glu Thr Ala Gly Ala Thr Cys Gln Asn Phe
                405                 410                 415

Leu Lys Ile Ile Ile Gln Cys Ala Ala Asp Asp Gln Lys Arg Ile Lys
            420                 425                 430

Arg Arg Leu Glu Asn Leu Met Ser Gln Ile Glu Asn Ala Glu Arg Thr
            435                 440                 445

Lys Ala Asp Leu Met Asp Asp Gln Ser Glu
    450                 455
```

```
<210> SEQ ID NO 15
<211> LENGTH: 588
<212> TYPE: DNA
<213> ORGANISM: Schizosaccharomyces pombe
<220> FEATURE:
<221> NAME/KEY: CDS
<222> LOCATION: (1)..(588)

<400> SEQUENCE: 15
```

```
atg tca gaa aag act agc aca gtt aca ata cac tat gga aat cag cga        48
Met Ser Glu Lys Thr Ser Thr Val Thr Ile His Tyr Gly Asn Gln Arg
  1               5                  10                  15 ttt ccg gta gca gtc aat cta aat gag acg tta agt gaa ctg att gat        96
Phe Pro Val Ala Val Asn Leu Asn Glu Thr Leu Ser Glu Leu Ile Asp
                 20                  25                  30 gat tta ctt gaa acg act gag att tct gag aag aaa gtc aag ctt ttt       144
Asp Leu Leu Glu Thr Thr Glu Ile Ser Glu Lys Lys Val Lys Leu Phe
             35                  40                  45 tac gct ggc aag cgt tta aaa gac aaa aaa gcc tcg tta tca aaa ttg       192
Tyr Ala Gly Lys Arg Leu Lys Asp Lys Lys Ala Ser Leu Ser Lys Leu
         50                  55                  60 ggt tta aaa aat cat agt aaa att cta tgt ata aga cca cat aag caa       240
Gly Leu Lys Asn His Ser Lys Ile Leu Cys Ile Arg Pro His Lys Gln
 65                  70                  75                  80 caa cga ggt tcc aag gaa aaa gac acg gtt gag ccc gct ccg aaa gcg       288
Gln Arg Gly Ser Lys Glu Lys Asp Thr Val Glu Pro Ala Pro Lys Ala
                 85                  90                  95 gaa gcg gag aat cct gta ttt tcg cgt att tct gga gaa ata aaa gcc       336
Glu Ala Glu Asn Pro Val Phe Ser Arg Ile Ser Gly Glu Ile Lys Ala
            100                 105                 110 atc gat cag tat gtt gac aaa gaa ctt tcc ccc atg tac gac aat tac       384
Ile Asp Gln Tyr Val Asp Lys Glu Leu Ser Pro Met Tyr Asp Asn Tyr
        115                 120                 125 gta aat aaa ccg tcg aac gat cca aag cag aaa aac aaa cag aaa cta       432
Val Asn Lys Pro Ser Asn Asp Pro Lys Gln Lys Asn Lys Gln Lys Leu
    130                 135                 140 atg ata agt gaa cta ctt tta caa cag ctt tta aaa ttg gat gga gtt       480
Met Ile Ser Glu Leu Leu Leu Gln Gln Leu Leu Lys Leu Asp Gly Val
145                 150                 155                 160
```

```
gac gta ctg ggc agc gag aaa ttg cgt ttt gaa cgg aag caa ctt gtt      528
Asp Val Leu Gly Ser Glu Lys Leu Arg Phe Glu Arg Lys Gln Leu Val
                165                 170                 175 tct aag atc caa aaa atg ttg gat cac gtt gac caa aca agc caa gaa      576
Ser Lys Ile Gln Lys Met Leu Asp His Val Asp Gln Thr Ser Gln Glu
            180                 185                 190 gtg gcc gca tag                                                      588
Val Ala Ala
        195
```

<210> SEQ ID NO 16
<211> LENGTH: 195
<212> TYPE: PRT
<213> ORGANISM: Schizosaccharomyces pombe

<400> SEQUENCE: 16

```
Met Ser Glu Lys Thr Ser Thr Val Thr Ile His Tyr Gly Asn Gln Arg
 1               5                  10                  15

Phe Pro Val Ala Val Asn Leu Asn Glu Thr Leu Ser Glu Leu Ile Asp
                20                  25                  30

Asp Leu Leu Glu Thr Thr Glu Ile Ser Glu Lys Lys Val Lys Leu Phe
            35                  40                  45

Tyr Ala Gly Lys Arg Leu Lys Asp Lys Ala Ser Leu Ser Lys Leu
        50                  55                  60

Gly Leu Lys Asn His Ser Lys Ile Leu Cys Ile Arg Pro His Lys Gln
 65                  70                  75                  80

Gln Arg Gly Ser Lys Glu Lys Asp Thr Val Glu Pro Ala Pro Lys Ala
                85                  90                  95

Glu Ala Glu Asn Pro Val Phe Ser Arg Ile Ser Gly Glu Ile Lys Ala
            100                 105                 110

Ile Asp Gln Tyr Val Asp Lys Glu Leu Ser Pro Met Tyr Asp Asn Tyr
        115                 120                 125

Val Asn Lys Pro Ser Asn Asp Pro Lys Gln Lys Asn Lys Gln Lys Leu
    130                 135                 140

Met Ile Ser Glu Leu Leu Leu Gln Gln Leu Leu Lys Leu Asp Gly Val
145                 150                 155                 160

Asp Val Leu Gly Ser Glu Lys Leu Arg Phe Glu Arg Lys Gln Leu Val
                165                 170                 175

Ser Lys Ile Gln Lys Met Leu Asp His Val Asp Gln Thr Ser Gln Glu
            180                 185                 190

Val Ala Ala
        195
```

<210> SEQ ID NO 17
<211> LENGTH: 621
<212> TYPE: DNA
<213> ORGANISM: Schizosaccharomyces pombe
<220> FEATURE:
<221> NAME/KEY: CDS
<222> LOCATION: (1)..(621)

<400> SEQUENCE: 17

```
atg tct ttt ttt acc cag ttg tgt tct atg gat aaa aaa tat tgg atc       48
Met Ser Phe Phe Thr Gln Leu Cys Ser Met Asp Lys Lys Tyr Trp Ile
 1               5                  10                  15 tct cta gct gta ttg tca gtt act gtt ttg att agc gca tta tgt aaa      96
Ser Leu Ala Val Leu Ser Val Thr Val Leu Ile Ser Ala Leu Leu Lys
                20                  25                  30 aag aga gct act gaa acc gaa gat att gtc gtt gtt cat tac gat ggc     144
```

```
Lys Arg Ala Thr Glu Thr Glu Asp Ile Val Val His Tyr Asp Gly
         35                  40                  45 gaa aag ttg aat ttt gtg ttg cga caa cca agg ctg aat atg gtt tct      192
Glu Lys Leu Asn Phe Val Leu Arg Gln Pro Arg Leu Asn Met Val Ser
         50                  55                  60 tac act agt ttt ctt cgt cgc gtg tgc aac gca ttt tca gta atg ccc      240
Tyr Thr Ser Phe Leu Arg Arg Val Cys Asn Ala Phe Ser Val Met Pro
 65                  70                  75                  80 gac aaa gcg tct ctc aag tta aac ggg gtg acc ctc aag gat ggt tca      288
Asp Lys Ala Ser Leu Lys Leu Asn Gly Val Thr Leu Lys Asp Gly Ser
                 85                  90                  95 ctt tcc gac caa aat gtg caa aat gga agt gaa tta gag ctc gaa tta      336
Leu Ser Asp Gln Asn Val Gln Asn Gly Ser Glu Leu Glu Leu Glu Leu
                100                 105                 110 ccc aaa ctg agc ccg gca atg caa caa att gaa gca tat ata gat gag      384
Pro Lys Leu Ser Pro Ala Met Gln Gln Ile Glu Ala Tyr Ile Asp Glu
            115                 120                 125 ctt caa cag gat ctc gtc cct aaa att gaa gcc ttc tgc caa tcg tct      432
Leu Gln Gln Asp Leu Val Pro Lys Ile Glu Ala Phe Cys Gln Ser Ser
    130                 135                 140 ccc gct tcg gca caa gat gtt caa gat ttg cat aca cgc ctt agt gaa      480
Pro Ala Ser Ala Gln Asp Val Gln Asp Leu His Thr Arg Leu Ser Glu
145                 150                 155                 160 aca ttg ttg gct agg atg ata aaa tta gat gct gtt aat gtt gaa gac      528
Thr Leu Leu Ala Arg Met Ile Lys Leu Asp Ala Val Asn Val Glu Asp
                165                 170                 175 gac cca gaa gct cgt ctt aaa aga aaa gaa gct att cgt tta tct caa      576
Asp Pro Glu Ala Arg Leu Lys Arg Lys Glu Ala Ile Arg Leu Ser Gln
            180                 185                 190 caa tat ttg agt aaa cta gat tcc acc aag aat caa aac aaa tga          621
Gln Tyr Leu Ser Lys Leu Asp Ser Thr Lys Asn Gln Asn Lys
        195                 200                 205

<210> SEQ ID NO 18
<211> LENGTH: 206
<212> TYPE: PRT
<213> ORGANISM: Schizosaccharomyces pombe

<400> SEQUENCE: 18

Met Ser Phe Phe Thr Gln Leu Cys Ser Met Asp Lys Lys Tyr Trp Ile
 1               5                  10                  15

Ser Leu Ala Val Leu Ser Val Thr Val Leu Ile Ser Ala Leu Leu Lys
                20                  25                  30

Lys Arg Ala Thr Glu Thr Glu Asp Ile Val Val His Tyr Asp Gly
         35                  40                  45

Glu Lys Leu Asn Phe Val Leu Arg Gln Pro Arg Leu Asn Met Val Ser
         50                  55                  60

Tyr Thr Ser Phe Leu Arg Arg Val Cys Asn Ala Phe Ser Val Met Pro
 65                  70                  75                  80

Asp Lys Ala Ser Leu Lys Leu Asn Gly Val Thr Leu Lys Asp Gly Ser
                 85                  90                  95

Leu Ser Asp Gln Asn Val Gln Asn Gly Ser Glu Leu Glu Leu Glu Leu
                100                 105                 110

Pro Lys Leu Ser Pro Ala Met Gln Gln Ile Glu Ala Tyr Ile Asp Glu
            115                 120                 125

Leu Gln Gln Asp Leu Val Pro Lys Ile Glu Ala Phe Cys Gln Ser Ser
    130                 135                 140

Pro Ala Ser Ala Gln Asp Val Gln Asp Leu His Thr Arg Leu Ser Glu
```

-continued

```
                145                 150                 155                 160
Thr Leu Leu Ala Arg Met Ile Lys Leu Asp Ala Val Asn Val Glu Asp
                    165                 170                 175

Asp Pro Glu Ala Arg Leu Lys Arg Lys Glu Ala Ile Arg Leu Ser Gln
                180                 185                 190

Gln Tyr Leu Ser Lys Leu Asp Ser Thr Lys Asn Gln Asn Lys
            195                 200                 205

<210> SEQ ID NO 19
<211> LENGTH: 2534
<212> TYPE: DNA
<213> ORGANISM: Homo sapiens
<220> FEATURE:
<221> NAME/KEY: CDS
<222> LOCATION: (307)..(2034)

<400> SEQUENCE: 19
gcggagctcc gcatccaacc ccgggccgcg gccaacttct ctggactgga ccagaagttt      60
ctagccggcc agttgctacc tccctttatc tcctccttcc cctctggcag cgaggaggct     120
atttccagac acttccaccc ctctctggcc acgtcacccc cgcctttaat tcataaaggt     180
gcccggcgcc ggcttccgg  acacgtcggc ggcggagagg ggcccacggc ggcggcccgg     240
ccagagactc ggcgcccgga gccagcgccc cgcacccgcg ccccagcggg cagacccccaa    300 cccagc atg agc gcc gcc acc cac tcg ccc atg atg cag gtg gcg tcc        348
       Met Ser Ala Ala Thr His Ser Pro Met Met Gln Val Ala Ser
         1               5                  10 ggc aac ggt gac cgc gac cct ttg ccc ccc gga tgg gag atc aag atc       396
Gly Asn Gly Asp Arg Asp Pro Leu Pro Pro Gly Trp Glu Ile Lys Ile
 15                  20                  25                  30 gac ccg cag acc ggc tgg ccc ttc ttc gtg gac cac aac agc cgc acc       444
Asp Pro Gln Thr Gly Trp Pro Phe Phe Val Asp His Asn Ser Arg Thr
                 35                  40                  45 act acg tgg aac gac ccg cgc gtg ccc tct gag ggc ccc aag gag act       492
Thr Thr Trp Asn Asp Pro Arg Val Pro Ser Glu Gly Pro Lys Glu Thr
             50                  55                  60 cca tcc tct gcc aat ggc cct tcc cgg gag ggc tct agg ctg ccg cct       540
Pro Ser Ser Ala Asn Gly Pro Ser Arg Glu Gly Ser Arg Leu Pro Pro
         65                  70                  75 gct agg gaa ggc cac cct gtg tac ccc cag ctc cga cca ggc tac att       588
Ala Arg Glu Gly His Pro Val Tyr Pro Gln Leu Arg Pro Gly Tyr Ile
     80                  85                  90 ccc att cct gtg ctc cat gaa ggc gct gag aac cgg cag gtg cac cct       636
Pro Ile Pro Val Leu His Glu Gly Ala Glu Asn Arg Gln Val His Pro
 95                 100                 105                 110 ttc cat gtc tat ccc cag cct ggg atg cag cga ttc cga act gag gcg       684
Phe His Val Tyr Pro Gln Pro Gly Met Gln Arg Phe Arg Thr Glu Ala
                115                 120                 125 gca gca gcg gct cct cag agg tcc cag tca cct ctg cgg ggc atg cca       732
Ala Ala Ala Ala Pro Gln Arg Ser Gln Ser Pro Leu Arg Gly Met Pro
            130                 135                 140 gaa acc act cag cca gat aaa cag tgt gga cag gtg gca gcg gcg gcg       780
Glu Thr Thr Gln Pro Asp Lys Gln Cys Gly Gln Val Ala Ala Ala Ala
        145                 150                 155 gca gcc cag ccc cca gcc tcc cac gga cct gag cgg tcc cag tct cca       828
Ala Ala Gln Pro Pro Ala Ser His Gly Pro Glu Arg Ser Gln Ser Pro
    160                 165                 170 gct gcc tct gac tgc tca tcc tca tcc tcc tcg gcc agc ctg cct tcc       876
Ala Ala Ser Asp Cys Ser Ser Ser Ser Ser Ala Ser Leu Pro Ser
175                 180                 185                 190
```

```
tcc ggc agg agc agc ctg ggc agt cac cag ctc ccg cgg ggg tac atc    924
Ser Gly Arg Ser Ser Leu Gly Ser His Gln Leu Pro Arg Gly Tyr Ile
            195                 200                 205 tcc att ccg gtg ata cac gag cag aac gtt acc cgg cca gca gcc cag    972
Ser Ile Pro Val Ile His Glu Gln Asn Val Thr Arg Pro Ala Ala Gln
            210                 215                 220 ccc tcc ttc cac aaa gcc cag aag acg cac tac cca gcg cag agg ggt   1020
Pro Ser Phe His Lys Ala Gln Lys Thr His Tyr Pro Ala Gln Arg Gly
            225                 230                 235 gag tac cag acc cac cag cct gtg tac cac aag atc cag ggg gat gac   1068
Glu Tyr Gln Thr His Gln Pro Val Tyr His Lys Ile Gln Gly Asp Asp
        240                 245                 250 tgg gag ccc cgg ccc ctg cgg gcg gca tcc ccg ttc agg tca tct gtc   1116
Trp Glu Pro Arg Pro Leu Arg Ala Ala Ser Pro Phe Arg Ser Ser Val
255                 260                 265                 270 cag ggt gca tcg agc cgg gag ggc tca cca gcc agg agc agc acg cca   1164
Gln Gly Ala Ser Ser Arg Glu Gly Ser Pro Ala Arg Ser Ser Thr Pro
                275                 280                 285 ctc cac tcc ccc tcg ccc atc cgt gtg cac acc gtg gtc gac agg cct   1212
Leu His Ser Pro Ser Pro Ile Arg Val His Thr Val Val Asp Arg Pro
                290                 295                 300 cag cag ccc atg acc cat cga gaa act gca cct gtt tcc cag cct gaa   1260
Gln Gln Pro Met Thr His Arg Glu Thr Ala Pro Val Ser Gln Pro Glu
            305                 310                 315 aac aaa cca gaa agt aag cca ggc cca gtt gga cca gaa ctc cct cct   1308
Asn Lys Pro Glu Ser Lys Pro Gly Pro Val Gly Pro Glu Leu Pro Pro
        320                 325                 330 gga cac atc cca att caa gtg atc cgc aaa gag gtg gat tct aaa cct   1356
Gly His Ile Pro Ile Gln Val Ile Arg Lys Glu Val Asp Ser Lys Pro
335                 340                 345                 350 gtt tcc cag aag ccc cca cct ccc tct gag aag gta gag gtg aaa gtt   1404
Val Ser Gln Lys Pro Pro Pro Pro Ser Glu Lys Val Glu Val Lys Val
                355                 360                 365 ccc cct gct cca gtt cct tgt cct cct ccc agc cct ggc cct tct gct   1452
Pro Pro Ala Pro Val Pro Cys Pro Pro Pro Ser Pro Gly Pro Ser Ala
                370                 375                 380 gtc ccc tct tcc ccc aag agt gtg gct aca gaa gag agg gca gcc ccc   1500
Val Pro Ser Ser Pro Lys Ser Val Ala Thr Glu Glu Arg Ala Ala Pro
            385                 390                 395 agc act gcc cct gca gaa gct aca cct cca aaa cca gga gaa gcc gag   1548
Ser Thr Ala Pro Ala Glu Ala Thr Pro Pro Lys Pro Gly Glu Ala Glu
        400                 405                 410 gct ccc cca aaa cat cca gga gtg ctg aaa gtg gaa gcc atc ctg gag   1596
Ala Pro Pro Lys His Pro Gly Val Leu Lys Val Glu Ala Ile Leu Glu
415                 420                 425                 430 aag gtg cag ggg ctg gag cag gct gta gac aac ttt gaa ggc aag aag   1644
Lys Val Gln Gly Leu Glu Gln Ala Val Asp Asn Phe Glu Gly Lys Lys
                435                 440                 445 act gac aaa aag tac ctg atg atc gaa gag tat ttg acc aaa gag ctg   1692
Thr Asp Lys Lys Tyr Leu Met Ile Glu Glu Tyr Leu Thr Lys Glu Leu
            450                 455                 460 ctg gcc ctg gat tca gtg gac ccc gag gga cga gcc gat gtg cgt cag   1740
Leu Ala Leu Asp Ser Val Asp Pro Glu Gly Arg Ala Asp Val Arg Gln
        465                 470                 475 gcc agg aga gac ggt gtc agg aag gtt cag acc atc ttg gaa aaa ctt   1788
Ala Arg Arg Asp Gly Val Arg Lys Val Gln Thr Ile Leu Glu Lys Leu
480                 485                 490 gaa cag aaa gcc att gat gtc cca ggt caa gtc cag gtc tat gaa ctc   1836
Glu Gln Lys Ala Ile Asp Val Pro Gly Gln Val Gln Val Tyr Glu Leu
```

```
                495                 500                 505                 510
cag ccc agc aac ctt gaa gca gat cag cca ctg cag gca atc atg gag        1884
Gln Pro Ser Asn Leu Glu Ala Asp Gln Pro Leu Gln Ala Ile Met Glu
            515                 520                 525 atg ggt gcc gtg gca gca gac aag ggc aag aaa aat gct gga aat gca        1932
Met Gly Ala Val Ala Ala Asp Lys Gly Lys Lys Asn Ala Gly Asn Ala
            530                 535                 540 gaa gat ccc cac aca gaa acc cag cag cca gaa gcc aca gca gca gcg        1980
Glu Asp Pro His Thr Glu Thr Gln Gln Pro Glu Ala Thr Ala Ala Ala
            545                 550                 555 act tca aac ccc agc agc atg aca gac acc cct ggt aac cca gca gca        2028
Thr Ser Asn Pro Ser Ser Met Thr Asp Thr Pro Gly Asn Pro Ala Ala
            560                 565                 570 ccg tag cctctgccct gtaaaaatca gactcggaac cgatgtgtgc tttagggaat         2084
Pro
575 tttaagttgc atgcatttca gagactttaa gtcagttggt ttttattagc tgcttggtat     2144 gcagtaactt gggtggaggc aaaacactaa taaagggct aaaaaggaaa atgatgcttt      2204 tcttctatat tcttactctg tacaaataaa gaagttgctt gttgtttgag aagtttaacc    2264 ccgttgcttg ttctgcagcc ctgtctactt gggcacccc accacctgtt agctgtggtt     2324 gtgcactgtc ttttgtagct ctggactgga ggggtagatg gggagtcaat tacccatcac    2384 ataaatatga acatttatc agaaatgttg ccattttaat gagatgattt tcttcatctc     2444 ataattaaaa tacctgactt tagagagagt aaaatgtgcc aggagccata ggaatatctg    2504 tatgttggat gactttaatg ctacattttc                                      2534

<210> SEQ ID NO 20
<211> LENGTH: 575
<212> TYPE: PRT
<213> ORGANISM: Homo sapiens

<400> SEQUENCE: 20

Met Ser Ala Ala Thr His Ser Pro Met Met Gln Val Ala Ser Gly Asn
 1               5                  10                  15

Gly Asp Arg Asp Pro Leu Pro Pro Gly Trp Glu Ile Lys Ile Asp Pro
                20                  25                  30

Gln Thr Gly Trp Pro Phe Phe Val Asp His Asn Ser Arg Thr Thr Thr
            35                  40                  45

Trp Asn Asp Pro Arg Val Pro Ser Glu Gly Pro Lys Glu Thr Pro Ser
        50                  55                  60

Ser Ala Asn Gly Pro Ser Arg Glu Gly Ser Arg Leu Pro Pro Ala Arg
65                  70                  75                  80

Glu Gly His Pro Val Tyr Pro Gln Leu Arg Pro Gly Tyr Ile Pro Ile
                85                  90                  95

Pro Val Leu His Glu Gly Ala Glu Asn Arg Gln Val His Pro Phe His
            100                 105                 110

Val Tyr Pro Gln Pro Gly Met Gln Arg Phe Arg Thr Glu Ala Ala Ala
        115                 120                 125

Ala Ala Pro Gln Arg Ser Gln Ser Pro Leu Arg Gly Met Pro Glu Thr
    130                 135                 140

Thr Gln Pro Asp Lys Gln Cys Gly Gln Val Ala Ala Ala Ala Ala Ala
145                 150                 155                 160

Gln Pro Pro Ala Ser His Gly Pro Glu Arg Ser Gln Ser Pro Ala Ala
                165                 170                 175
```

```
Ser Asp Cys Ser Ser Ser Ser Ser Ala Ser Leu Pro Ser Ser Gly
            180                 185                 190

Arg Ser Ser Leu Gly Ser His Gln Leu Pro Arg Gly Tyr Ile Ser Ile
    195                 200                 205

Pro Val Ile His Glu Gln Asn Val Thr Arg Pro Ala Ala Gln Pro Ser
210                 215                 220

Phe His Lys Ala Gln Lys Thr His Tyr Pro Ala Gln Arg Gly Glu Tyr
225                 230                 235                 240

Gln Thr His Gln Pro Val Tyr His Lys Ile Gln Gly Asp Asp Trp Glu
                245                 250                 255

Pro Arg Pro Leu Arg Ala Ala Ser Pro Phe Arg Ser Ser Val Gln Gly
            260                 265                 270

Ala Ser Ser Arg Glu Gly Ser Pro Ala Arg Ser Ser Thr Pro Leu His
    275                 280                 285

Ser Pro Ser Pro Ile Arg Val His Thr Val Val Asp Arg Pro Gln Gln
290                 295                 300

Pro Met Thr His Arg Glu Thr Ala Pro Val Ser Gln Pro Glu Asn Lys
305                 310                 315                 320

Pro Glu Ser Lys Pro Gly Pro Val Gly Pro Glu Leu Pro Pro Gly His
                325                 330                 335

Ile Pro Ile Gln Val Ile Arg Lys Glu Val Asp Ser Lys Pro Val Ser
            340                 345                 350

Gln Lys Pro Pro Pro Ser Glu Lys Val Glu Val Lys Val Pro Pro
    355                 360                 365

Ala Pro Val Pro Cys Pro Pro Ser Pro Gly Pro Ser Ala Val Pro
370                 375                 380

Ser Ser Pro Lys Ser Val Ala Thr Glu Glu Arg Ala Ala Pro Ser Thr
385                 390                 395                 400

Ala Pro Ala Glu Ala Thr Pro Lys Pro Gly Glu Ala Glu Ala Pro
                405                 410                 415

Pro Lys His Pro Gly Val Leu Lys Val Glu Ala Ile Leu Glu Lys Val
            420                 425                 430

Gln Gly Leu Glu Gln Ala Val Asp Asn Phe Glu Gly Lys Lys Thr Asp
    435                 440                 445

Lys Lys Tyr Leu Met Ile Glu Glu Tyr Leu Thr Lys Glu Leu Leu Ala
450                 455                 460

Leu Asp Ser Val Asp Pro Glu Gly Arg Ala Asp Val Arg Gln Ala Arg
465                 470                 475                 480

Arg Asp Gly Val Arg Lys Val Gln Thr Ile Leu Glu Lys Leu Glu Gln
                485                 490                 495

Lys Ala Ile Asp Val Pro Gly Gln Val Gln Val Tyr Glu Leu Gln Pro
            500                 505                 510

Ser Asn Leu Glu Ala Asp Gln Pro Leu Gln Ala Ile Met Glu Met Gly
    515                 520                 525

Ala Val Ala Ala Asp Lys Gly Lys Lys Asn Ala Gly Asn Ala Glu Asp
530                 535                 540

Pro His Thr Glu Thr Gln Gln Pro Glu Ala Thr Ala Ala Thr Ser
545                 550                 555                 560

Asn Pro Ser Ser Met Thr Asp Thr Pro Gly Asn Pro Ala Ala Pro
                565                 570                 575

<210> SEQ ID NO 21
<211> LENGTH: 1966
<212> TYPE: DNA
```

-continued

```
<213> ORGANISM: Homo sapiens
<220> FEATURE:
<221> NAME/KEY: CDS
<222> LOCATION: (43)..(1416)

<400> SEQUENCE: 21
cggtgggagc ggggcgggaa gcgcttcagg gcagcggatc cc atg tcg gcc ctg         54
                                                Met Ser Ala Leu
                                                 1 agg cgc tcg ggc tac ggc ccc agt gac ggt ccg tcc tac ggc cgc tac       102
Arg Arg Ser Gly Tyr Gly Pro Ser Asp Gly Pro Ser Tyr Gly Arg Tyr
  5              10                  15                  20 tac ggg cct ggg ggt gga gat gtg ccg gta cac cca cct cca ccc tta       150
Tyr Gly Pro Gly Gly Gly Asp Val Pro Val His Pro Pro Pro Pro Leu
             25                  30                  35 tat cct ctt cgc cct gaa cct ccc cag cct ccc att tcc tgg cgg gtg       198
Tyr Pro Leu Arg Pro Glu Pro Pro Gln Pro Pro Ile Ser Trp Arg Val
         40                  45                  50 cgc ggg ggc ggc ccg gcg gag acc acc tgg ctg gga gaa ggc gga gga       246
Arg Gly Gly Gly Pro Ala Glu Thr Thr Trp Leu Gly Glu Gly Gly Gly
     55                  60                  65 ggc gat ggc tac tat ccc tcg gga ggc gcc tgg cca gag cct ggt cga       294
Gly Asp Gly Tyr Tyr Pro Ser Gly Gly Ala Trp Pro Glu Pro Gly Arg
 70                  75                  80 gcc gga gga agc cac cag gag cag cca cca tat cct agc tac aat tct       342
Ala Gly Gly Ser His Gln Glu Gln Pro Pro Tyr Pro Ser Tyr Asn Ser
 85                  90                  95                 100 aac tat tgg aat tct act gcg aga tct agg gct cct tac cca agt aca       390
Asn Tyr Trp Asn Ser Thr Ala Arg Ser Arg Ala Pro Tyr Pro Ser Thr
                 105                 110                 115 tat cct gta aga cca gaa ttg caa ggc cag agt ttg aat tct tat aca       438
Tyr Pro Val Arg Pro Glu Leu Gln Gly Gln Ser Leu Asn Ser Tyr Thr
             120                 125                 130 aat gga gcg tat ggt cca aca tac ccc cca ggc cct ggg gca aat act       486
Asn Gly Ala Tyr Gly Pro Thr Tyr Pro Pro Gly Pro Gly Ala Asn Thr
         135                 140                 145 gcc tca tac tca ggg gct tat tat gca cct ggt tat act cag acc agt       534
Ala Ser Tyr Ser Gly Ala Tyr Tyr Ala Pro Gly Tyr Thr Gln Thr Ser
     150                 155                 160 tac tcc aca gaa gtt cca agt act tac cgt tca tct ggc aac agc cca       582
Tyr Ser Thr Glu Val Pro Ser Thr Tyr Arg Ser Ser Gly Asn Ser Pro
165                 170                 175                 180 act cca gtc tct cgt tgg atc tat ccc cag cag gac tgt cag act gaa       630
Thr Pro Val Ser Arg Trp Ile Tyr Pro Gln Gln Asp Cys Gln Thr Glu
                 185                 190                 195 gca ccc cct ctt agg ggg cag gtt cca gga tat ccg cct tca cag aac       678
Ala Pro Pro Leu Arg Gly Gln Val Pro Gly Tyr Pro Pro Ser Gln Asn
             200                 205                 210 cct gga atg acc ctg ccc cat tat cct tat gga gat ggt aat cgt agt       726
Pro Gly Met Thr Leu Pro His Tyr Pro Tyr Gly Asp Gly Asn Arg Ser
         215                 220                 225 gtt cca caa tca gga ccg act gta cga cca caa gaa gat gcg tgg gct       774
Val Pro Gln Ser Gly Pro Thr Val Arg Pro Gln Glu Asp Ala Trp Ala
     230                 235                 240 tct cct ggt gct tat gga atg ggt ggc cgt tat ccc tgg cct tca tca       822
Ser Pro Gly Ala Tyr Gly Met Gly Gly Arg Tyr Pro Trp Pro Ser Ser
245                 250                 255                 260 gcg ccc tca gca cca ccc ggc aat ctc tac atg act gaa agt act tca       870
Ala Pro Ser Ala Pro Pro Gly Asn Leu Tyr Met Thr Glu Ser Thr Ser
                 265                 270                 275
```

```
cca tgg cct agc agt ggc tct ccc cag tca ccc cct tca ccc cca gtc    918
Pro Trp Pro Ser Ser Gly Ser Pro Gln Ser Pro Pro Ser Pro Pro Val
        280                 285                 290 cag cag ccc aag gat tct tca tac ccc tat agc caa tca gat caa agc    966
Gln Gln Pro Lys Asp Ser Ser Tyr Pro Tyr Ser Gln Ser Asp Gln Ser
295                 300                 305 atg aac cgg cac aac ttt cct tgc agt gtc cat cag tac gaa tcc tcg   1014
Met Asn Arg His Asn Phe Pro Cys Ser Val His Gln Tyr Glu Ser Ser
        310                 315                 320 ggg aca gtg atc aat gaa gat tca gat ctt ttg gat tcc caa gtc cag   1062
Gly Thr Val Ile Asn Glu Asp Ser Asp Leu Leu Asp Ser Gln Val Gln
325                 330                 335                 340 tat agt gct gag cct cag ctg tat ggt aat gcc acc agt gac cat ccc   1110
Tyr Ser Ala Glu Pro Gln Leu Tyr Gly Asn Ala Thr Ser Asp His Pro
            345                 350                 355 aac aat caa gat caa agt agc agt ctt cct gaa gaa tgt gta cct tca   1158
Asn Asn Gln Asp Gln Ser Ser Ser Leu Pro Glu Glu Cys Val Pro Ser
        360                 365                 370 gat gaa agt act cct ccg agt att aaa aaa atc ata cat gtg ctg gag   1206
Asp Glu Ser Thr Pro Pro Ser Ile Lys Lys Ile Ile His Val Leu Glu
            375                 380                 385 aag gtc cag tat ctt gaa caa gaa gta gaa gaa ttt gta gga aaa aag   1254
Lys Val Gln Tyr Leu Glu Gln Glu Val Glu Glu Phe Val Gly Lys Lys
        390                 395                 400 aca gac aaa gca tac tgg ctt ctg gaa gaa atg cta acc aag gaa ctt   1302
Thr Asp Lys Ala Tyr Trp Leu Leu Glu Glu Met Leu Thr Lys Glu Leu
405                 410                 415                 420 ttg gaa ctg gat tca gtt gaa act ggg ggc cag gac tct gta cgg cag   1350
Leu Glu Leu Asp Ser Val Glu Thr Gly Gly Gln Asp Ser Val Arg Gln
            425                 430                 435 gcc aga aaa gag gct gtt tgt aag att cag gcc ata ctg gaa aaa tta   1398
Ala Arg Lys Glu Ala Val Cys Lys Ile Gln Ala Ile Leu Glu Lys Leu
        440                 445                 450 gaa aaa aaa gga tta tga aaggatttag aacaaagtgg aagcctgtta          1446
Glu Lys Lys Gly Leu
            455 ctaacttgac caaagaacac ttgattaggt taattaccct cttttttgaaa tgcctgttga  1506 tgacaagaag caatacattc cagcttttcc tttgatttta tacttgaaaa actggcaaag  1566 gaatggaaga atattttagt catgaagttg ttttcagttt tcagacgaat gaatgtaata  1626 ggaaactatg gagttaccaa tattgccaag tagactcact ccttaaaaaa tttatggata  1686 tctacaagct gcttattacc agcaggaggg aaacacactt cacacaacag gcttatcaga  1746 aacctaccag atgaaactgg atataatttg agacaaacag gatgtgtttt tttaaacatc  1806 tggatatctt gtcacatttt tgtacattgt gactgctttc aacatatact tcatgtgtaa  1866 ttatagctta gactttagcc ttcttggact tctgttttgt tttgttattt gcagtttaca  1926 aatatagtat tattctctaa aaaaaaaaaa aaaaaaaaa                         1966

<210> SEQ ID NO 22
<211> LENGTH: 457
<212> TYPE: PRT
<213> ORGANISM: Homo sapiens

<400> SEQUENCE: 22

Met Ser Ala Leu Arg Arg Ser Gly Tyr Gly Pro Ser Asp Gly Pro Ser
1               5                   10                  15

Tyr Gly Arg Tyr Tyr Gly Pro Gly Gly Asp Val Pro Val His Pro
            20                  25                  30
```

```
Pro Pro Pro Leu Tyr Pro Leu Arg Pro Glu Pro Pro Gln Pro Pro Ile
         35                  40                  45

Ser Trp Arg Val Arg Gly Gly Gly Pro Ala Glu Thr Thr Trp Leu Gly
 50                  55                  60

Glu Gly Gly Gly Gly Asp Gly Tyr Tyr Pro Ser Gly Gly Ala Trp Pro
 65                  70                  75                  80

Glu Pro Gly Arg Ala Gly Gly Ser His Gln Glu Gln Pro Pro Tyr Pro
                 85                  90                  95

Ser Tyr Asn Ser Asn Tyr Trp Asn Ser Thr Ala Arg Ser Arg Ala Pro
             100                 105                 110

Tyr Pro Ser Thr Tyr Pro Val Arg Pro Glu Leu Gln Gly Gln Ser Leu
         115                 120                 125

Asn Ser Tyr Thr Asn Gly Ala Tyr Gly Pro Thr Tyr Pro Pro Gly Pro
         130                 135                 140

Gly Ala Asn Thr Ala Ser Tyr Ser Gly Ala Tyr Tyr Ala Pro Gly Tyr
145                 150                 155                 160

Thr Gln Thr Ser Tyr Ser Thr Glu Val Pro Ser Thr Tyr Arg Ser Ser
                 165                 170                 175

Gly Asn Ser Pro Thr Pro Val Ser Arg Trp Ile Tyr Pro Gln Gln Asp
             180                 185                 190

Cys Gln Thr Glu Ala Pro Leu Arg Gly Gln Val Pro Gly Tyr Pro
         195                 200                 205

Pro Ser Gln Asn Pro Gly Met Thr Leu Pro His Tyr Pro Tyr Gly Asp
     210                 215                 220

Gly Asn Arg Ser Val Pro Gln Ser Gly Pro Thr Val Arg Pro Gln Glu
225                 230                 235                 240

Asp Ala Trp Ala Ser Pro Gly Ala Tyr Gly Met Gly Gly Arg Tyr Pro
                 245                 250                 255

Trp Pro Ser Ser Ala Pro Ser Ala Pro Pro Gly Asn Leu Tyr Met Thr
             260                 265                 270

Glu Ser Thr Ser Pro Trp Pro Ser Ser Gly Ser Pro Gln Ser Pro Pro
         275                 280                 285

Ser Pro Pro Val Gln Gln Pro Lys Asp Ser Ser Tyr Pro Tyr Ser Gln
         290                 295                 300

Ser Asp Gln Ser Met Asn Arg His Asn Phe Pro Cys Ser Val His Gln
305                 310                 315                 320

Tyr Glu Ser Ser Gly Thr Val Ile Asn Glu Asp Ser Asp Leu Leu Asp
                 325                 330                 335

Ser Gln Val Gln Tyr Ser Ala Glu Pro Gln Leu Tyr Gly Asn Ala Thr
             340                 345                 350

Ser Asp His Pro Asn Asn Gln Asp Gln Ser Ser Ser Leu Pro Glu Glu
         355                 360                 365

Cys Val Pro Ser Asp Glu Ser Thr Pro Pro Ser Ile Lys Lys Ile Ile
         370                 375                 380

His Val Leu Glu Lys Val Gln Tyr Leu Glu Gln Glu Val Glu Glu Phe
385                 390                 395                 400

Val Gly Lys Lys Thr Asp Lys Ala Tyr Trp Leu Leu Glu Glu Met Leu
                 405                 410                 415

Thr Lys Glu Leu Leu Glu Leu Asp Ser Val Glu Thr Gly Gly Gln Asp
             420                 425                 430

Ser Val Arg Gln Ala Arg Lys Glu Ala Val Cys Lys Ile Gln Ala Ile
         435                 440                 445
```

-continued

```
Leu Glu Lys Leu Glu Lys Lys Gly Leu
    450                 455

<210> SEQ ID NO 23
<211> LENGTH: 4308
<212> TYPE: DNA
<213> ORGANISM: Homo sapiens
<220> FEATURE:
<221> NAME/KEY: CDS
<222> LOCATION: (247)..(1590)
<220> FEATURE:
<221> NAME/KEY: misc_feature
<222> LOCATION: (1)..(4308)
<223> OTHER INFORMATION: n=a,c,t or g

<400> SEQUENCE: 23 ccccccccccc cccccccccc ccngaagacg cccggagcgg ctgctgcagc cagtagcggc      60
cccttcaccg gctgccccgc tcagacctag tcgggagggg tgcgaggcat gcagctgggg     120
gcccagctcc ggtgccgcac cccgtaaagg gctgatcttc cacctcgcca cctcagccac     180
gggacgccaa gaccgcatcc aattcagact tcttttggtg cttgtgaaac tgaacacaac     240 aaaagt atg gat atg gga aac caa cat cct tct att agt agg ctt cag        288
       Met Asp Met Gly Asn Gln His Pro Ser Ile Ser Arg Leu Gln
        1               5                  10 gaa atc caa aag gaa gta aaa agt gta gaa cag caa gtt atc ggc ttc        336
Glu Ile Gln Lys Glu Val Lys Ser Val Glu Gln Gln Val Ile Gly Phe
 15                  20                  25                  30 agt ggt ctg tca gat gac aag aat tac aag aaa ctg gag agg att cta        384
Ser Gly Leu Ser Asp Asp Lys Asn Tyr Lys Lys Leu Glu Arg Ile Leu
                 35                  40                  45 aca aaa cag ctt ttt gaa ata gac tct gta gat act gaa gga aaa gga        432
Thr Lys Gln Leu Phe Glu Ile Asp Ser Val Asp Thr Glu Gly Lys Gly
             50                  55                  60 gat att cag caa gct agg aag cgg gca gca cag gag aca gaa cgt ctt        480
Asp Ile Gln Gln Ala Arg Lys Arg Ala Ala Gln Glu Thr Glu Arg Leu
         65                  70                  75 ctc aaa gag ttg gag cag aat gca aac cac cca cac cgg att gaa ata        528
Leu Lys Glu Leu Glu Gln Asn Ala Asn His Pro His Arg Ile Glu Ile
     80                  85                  90 cag aac att ttt gag gaa gcc cag tcc ctc gtg aga gag aaa att gtg        576
Gln Asn Ile Phe Glu Glu Ala Gln Ser Leu Val Arg Glu Lys Ile Val
 95                 100                 105                 110 cca ttt tat aat gga ggc aac tgc gta act gat gag ttt gaa gaa ggc        624
Pro Phe Tyr Asn Gly Gly Asn Cys Val Thr Asp Glu Phe Glu Glu Gly
                115                 120                 125 atc caa gat atc att ctg agg ctg aca cat gtt aaa act gga gga aaa        672
Ile Gln Asp Ile Ile Leu Arg Leu Thr His Val Lys Thr Gly Gly Lys
            130                 135                 140 atc tcc ttg cgg aaa gca agg tat cac act tta acc aaa atc tgt gcg        720
Ile Ser Leu Arg Lys Ala Arg Tyr His Thr Leu Thr Lys Ile Cys Ala
        145                 150                 155 gtg caa gag ata atc gaa gac tgc atg aaa aag cag cct tcc ctg ccg        768
Val Gln Glu Ile Ile Glu Asp Cys Met Lys Lys Gln Pro Ser Leu Pro
    160                 165                 170 ctt tcc gag gat gca cat cct tcc gtt gcc aaa atc aac ttc gtg atg        816
Leu Ser Glu Asp Ala His Pro Ser Val Ala Lys Ile Asn Phe Val Met
175                 180                 185                 190 tgt gag gtg aac aag gcc cga ggg gtc ctg att gca ctt ctg atg ggt        864
Cys Glu Val Asn Lys Ala Arg Gly Val Leu Ile Ala Leu Leu Met Gly
                195                 200                 205 gtg aac aac aat gag acc tgc agg cac tta tcc tgt gtg ctc tcg ggg        912
```

```
Val Asn Asn Asn Glu Thr Cys Arg His Leu Ser Cys Val Leu Ser Gly
            210                 215                 220 ctg atc gct gac ctg gat gct cta gat gtg tgc ggc cgg aca gaa atc     960
Leu Ile Ala Asp Leu Asp Ala Leu Asp Val Cys Gly Arg Thr Glu Ile
            225                 230                 235 aga aat tat cgg agg gag gta gta gaa gat atc aac aaa tta ttg aaa    1008
Arg Asn Tyr Arg Arg Glu Val Val Glu Asp Ile Asn Lys Leu Leu Lys
            240                 245                 250 tat ctg gat ttg gaa gag gaa gca gac aca act aaa gca ttt gac ctg    1056
Tyr Leu Asp Leu Glu Glu Glu Ala Asp Thr Thr Lys Ala Phe Asp Leu
255                 260                 265                 270 aga cag aat cat tcc att tta aaa ata gaa aag gtc ctc aag aga atg    1104
Arg Gln Asn His Ser Ile Leu Lys Ile Glu Lys Val Leu Lys Arg Met
                275                 280                 285 aga gaa ata aaa aat gaa ctt ctc caa gca caa aac cct tct gaa ttg    1152
Arg Glu Ile Lys Asn Glu Leu Leu Gln Ala Gln Asn Pro Ser Glu Leu
            290                 295                 300 tac ctg agc tcc aaa aca gaa ttg cag ggt tta att gga cag ttg gat    1200
Tyr Leu Ser Ser Lys Thr Glu Leu Gln Gly Leu Ile Gly Gln Leu Asp
            305                 310                 315 gag gta agt ctt gaa aaa aac ccc tgc atc cgg gaa gcc agg aga aga    1248
Glu Val Ser Leu Glu Lys Asn Pro Cys Ile Arg Glu Ala Arg Arg Arg
320                 325                 330 gca gtg atc gag gtg caa act ctg atc aca tat att gac ttg aag gag    1296
Ala Val Ile Glu Val Gln Thr Leu Ile Thr Tyr Ile Asp Leu Lys Glu
335                 340                 345                 350 gcc ctt gag aaa aga aag ctg ttt gct tgt gag gag cac cca tcc cat    1344
Ala Leu Glu Lys Arg Lys Leu Phe Ala Cys Glu Glu His Pro Ser His
                355                 360                 365 aaa gcc gtc tgg aac gtc ctt gga aac ttg tct gag atc cag gga gaa    1392
Lys Ala Val Trp Asn Val Leu Gly Asn Leu Ser Glu Ile Gln Gly Glu
            370                 375                 380 gtt ctt tca ttt gat gga aat cga acc gat aag aac tac atc cgg ctg    1440
Val Leu Ser Phe Asp Gly Asn Arg Thr Asp Lys Asn Tyr Ile Arg Leu
            385                 390                 395 gaa gag ctg ctc acc aag cag ctg cta gcc ctg gat gct gtt gat ccg    1488
Glu Glu Leu Leu Thr Lys Gln Leu Leu Ala Leu Asp Ala Val Asp Pro
            400                 405                 410 cag gga gaa gag aag tgt aag gct gcc agg aaa caa gct gtg agg ctt    1536
Gln Gly Glu Glu Lys Cys Lys Ala Ala Arg Lys Gln Ala Val Arg Leu
415                 420                 425                 430 gcg cag aat att ctc agc tat ctc gac ctg aaa tct gat gaa tgg gag    1584
Ala Gln Asn Ile Leu Ser Tyr Leu Asp Leu Lys Ser Asp Glu Trp Glu
                435                 440                 445 tac tga aataccagag atctcacttt tgatactgtt ttgcacttca tatgtcttc     1640
Tyr tatgtataga gagctttcag ttcattgatt tatacgtgca tatttcagtc tcagtattta   1700
tgattgaagc aaattctatt cagtatctgc tgcttttgat gttgcaagac aaatatcatt   1760
acagcacgtt aacttttcca ttcggatcat tatctgtatg atgtggtgtg gtttgtttgg   1820
tttgtccttt tttttgcgtt tttaatcaga aaacaaaata gaggcagctt ttgtagattt   1880
taaatgggtt gtgcaagcat taaaatgcag gtctttcaga atctagaact aggcataacc   1940
ttacataata ctaggaaaat tatgagaaag gggaattttt tggttaaata agagtaaggt   2000
tcaaacacaa gcagtacatg ttctgtttca ttatgctcga tagaaggctt ttttttcact   2060
tataaggcct gattggtcct acccagctta acggggtggg gttttttttgt ttgttcagac   2120 agtctgttct tttgtaaaca ttttagttg gaaaaacagc atctgcattt tccccatcct   2180
```

```
ctacgtttta gagaggaatc ttgttttgt gtgcaacata agaaaattat gaaaactaat    2240
agccaaaaaa cctttgagat tgcattaaag agaagggata aaggaccagc aataatacct    2300
tgtaagttgc ttttgtttgt aaaatctgag cttatagttt tccttagtga gtaaattcat    2360
aaggatggga acatttaaat taagttaatg ggccttttaaa aaaaaaaaag gaaacactca    2420
tacctgtagt tggaggatga atactggaga cgggttacca atgtcaggtt atactaaaac    2480
taaatcagaa agtctgaatg tagcacataa tggttctctt ctgttgtcca aggctgtaaa    2540
atggacagcc ttgtcacacc tccccggtgc tgttttacaa cgtgagggta gacgctgtca    2600
gtaacccaga gggaccaggc cttcctaggt tttctaggca gtcagctgtt aaccactcac    2660
ttagtaaatg tcataactac acctgctcca ggaccaatca gtgaacctg ctcggaatta    2720 aaggcttcct ctgggtgcct gctgaacaac tgagctcatg tcatgggcat gtggtggttt    2780
ctctgttgcc tgaaagagcc attaaagtca gtcgtgcgtg aagcatctct cttctaaagg    2840
atgtgtattt ccataaatgc tttctgagga tccggtacaa aatgatttcc caaagttctg    2900
aagtgccttg agaacatgtg ggtccgagtg ttataacaga ctcctccccc gggtcacctt    2960
ttgcctggtc atcctgttag agtacatctt tggaaatcca gggtaatatt ctctttcaga    3020
gatgctcatt gtgtaactct gtgtagggag atagtcactt taaacagctc aaagtagcta    3080
gctaaaggag tagccttaaa tacctaaaag atgacagaag catagcccctt aacaaatctt    3140 cagcttgtct ctcagtattt cccaatcatg aaaatccctt gctatgtctt tcctactaga    3200
aatgttctag aatcgctgga cggtggggtc agagggcagt cggtatttag gccgtgagct    3260
tcccatacta ctgcaggtcc aactcctggc aaccgcgggc tcaaggcagg tcattggaat    3320
ccacgttttg gccacagtag ttgtaggatt gcttttctgt atcataattt tagaatgctc    3380
ttaaaatctt gaggaagagt ttttatttt tatttatttt tgagatggag tctctgttgc    3440
ccaggctgca gtgcagtggt gccatctcag ctcactgcaa cctccacctc ccaggttcaa    3500
gcgattctcc tgcctcagcc acctgagtag ctgggagtac aggcatgtgg caccatgcct    3560
ggctaatttt tgtattttta atagagttga gatttcacca tgatggtcag gctggtctcg    3620
aactcctgac ctcgtgatcc gcccgcctcg gcccccaaaa gtgctgggat taacgggtgt    3680
gagccacggc gcccagccca ggaagagttt ttaaattaga gctctgttta attataccac    3740
tgggaaatca tggttacgct tcaggcatat tcttccccag agtactactt acatttttaaa   3800 tttcattttg taaagttaaa tgtcagcatt ccctttaaaa gtgtccattg ttcttttgaaa   3860 gtagacgttt cagtcattct tttcaaacaa gtgtttgtgt accttttgcc aagctgtggg    3920
catcgtgtgt gagtacaggg tgctcagctc ttccaccgtc attttgaatt gttcacatgg    3980
gtaattggtc atggaaatga tcagattgac cttgattgac tgtcaggcat ggctttgttt    4040
ctagtttcaa tctgttctcg ttccttgtac cggattattc tactcctgca atgaaccctg    4100
ttgacaccgg atttagctct tgtcggcctt cgtggggagc tgtttgtgtt aatatgagct    4160
actgcatgta attcttaaac tgggcttgtc acattgtatt gtattttgt gatctgtaat    4220 gaaaagaatc tgtactgcaa gtaaaaccta ctcccaaaa atgtgtggct ttgggtctgc    4280
attaaacgct gtagtccatg ttcatgcc                                       4308
```

<210> SEQ ID NO 24
<211> LENGTH: 447
<212> TYPE: PRT
<213> ORGANISM: Homo sapiens

<400> SEQUENCE: 24

Met Asp Met Gly Asn Gln His Pro Ser Ile Ser Arg Leu Gln Glu Ile
1               5                   10                  15

Gln Lys Glu Val Lys Ser Val Glu Gln Gln Val Ile Gly Phe Ser Gly
            20                  25                  30

Leu Ser Asp Asp Lys Asn Tyr Lys Lys Leu Glu Arg Ile Leu Thr Lys
        35                  40                  45

Gln Leu Phe Glu Ile Asp Ser Val Asp Thr Glu Gly Lys Gly Asp Ile
    50                  55                  60

Gln Gln Ala Arg Lys Arg Ala Ala Gln Glu Thr Glu Arg Leu Leu Lys
65                  70                  75                  80

Glu Leu Glu Gln Asn Ala Asn His Pro His Arg Ile Glu Ile Gln Asn
                85                  90                  95

Ile Phe Glu Glu Ala Gln Ser Leu Val Arg Glu Lys Ile Val Pro Phe
            100                 105                 110

Tyr Asn Gly Gly Asn Cys Val Thr Asp Glu Phe Glu Glu Gly Ile Gln
        115                 120                 125

Asp Ile Ile Leu Arg Leu Thr His Val Lys Thr Gly Gly Lys Ile Ser
    130                 135                 140

Leu Arg Lys Ala Arg Tyr His Thr Leu Thr Lys Ile Cys Ala Val Gln
145                 150                 155                 160

Glu Ile Ile Glu Asp Cys Met Lys Lys Gln Pro Ser Leu Pro Leu Ser
                165                 170                 175

Glu Asp Ala His Pro Ser Val Ala Lys Ile Asn Phe Val Met Cys Glu
            180                 185                 190

Val Asn Lys Ala Arg Gly Val Leu Ile Ala Leu Leu Met Gly Val Asn
        195                 200                 205

Asn Asn Glu Thr Cys Arg His Leu Ser Cys Val Leu Ser Gly Leu Ile
    210                 215                 220

Ala Asp Leu Asp Ala Leu Asp Val Cys Gly Arg Thr Glu Ile Arg Asn
225                 230                 235                 240

Tyr Arg Arg Glu Val Val Glu Asp Ile Asn Lys Leu Leu Lys Tyr Leu
                245                 250                 255

Asp Leu Glu Glu Glu Ala Asp Thr Thr Lys Ala Phe Asp Leu Arg Gln
            260                 265                 270

Asn His Ser Ile Leu Lys Ile Glu Lys Val Leu Lys Arg Met Arg Glu
        275                 280                 285

Ile Lys Asn Glu Leu Leu Gln Ala Gln Asn Pro Ser Glu Leu Tyr Leu
    290                 295                 300

Ser Ser Lys Thr Glu Leu Gln Gly Leu Ile Gly Gln Leu Asp Glu Val
305                 310                 315                 320

Ser Leu Glu Lys Asn Pro Cys Ile Arg Glu Ala Arg Arg Ala Val
                325                 330                 335

Ile Glu Val Gln Thr Leu Ile Thr Tyr Ile Asp Leu Lys Glu Ala Leu
            340                 345                 350

Glu Lys Arg Lys Leu Phe Ala Cys Glu Glu His Pro Ser His Lys Ala
        355                 360                 365

Val Trp Asn Val Leu Gly Asn Leu Ser Glu Ile Gln Gly Glu Val Leu
    370                 375                 380

```
-continued

Ser Phe Asp Gly Asn Arg Thr Asp Lys Asn Tyr Ile Arg Leu Glu Glu
385                 390                 395                 400

Leu Leu Thr Lys Gln Leu Leu Ala Leu Asp Ala Val Asp Pro Gln Gly
                405                 410                 415

Glu Glu Lys Cys Lys Ala Ala Arg Lys Gln Ala Val Arg Leu Ala Gln
            420                 425                 430

Asn Ile Leu Ser Tyr Leu Asp Leu Lys Ser Asp Glu Trp Glu Tyr
        435                 440                 445
```